US 8,617,112 B2

(12) United States Patent
Tanabe et al.

(10) Patent No.: US 8,617,112 B2
(45) Date of Patent: Dec. 31, 2013

(54) INDWELLING NEEDLE ASSEMBLY

(75) Inventors: Hidenori Tanabe, Nakakoma-gun (JP);
Ryoji Kobayashi, Nakakoma-gun (JP);
Kazuhiro Hashimoto, Nakakoma-gun
(JP); Takato Murashita, Nakakoma-gun
(JP)

(73) Assignee: Terumo Kabushiki Kaisha,
Shibuya-Ku, Tokyo (JP)

( * ) Notice: Subject to any disclaimer, the term of this
patent is extended or adjusted under 35
U.S.C. 154(b) by 45 days.

(21) Appl. No.: 12/593,430

(22) PCT Filed: Mar. 26, 2008

(86) PCT No.: PCT/JP2008/055697
§ 371 (c)(1),
(2), (4) Date: Sep. 28, 2009

(87) PCT Pub. No.: WO2008/123297
PCT Pub. Date: Oct. 16, 2008

(65) Prior Publication Data
US 2010/0106092 A1    Apr. 29, 2010

(30) Foreign Application Priority Data

Mar. 30, 2007  (JP) ................................. 2007-092262
Mar. 30, 2007  (JP) ................................. 2007-092263

(51) Int. Cl.
*A61M 5/178* (2006.01)
(52) U.S. Cl.
USPC ................................. 604/164.08; 604/164.01
(58) Field of Classification Search
USPC ............... 604/164.08, 264, 164.01, 171, 157,
604/533, 158, 110, 164.12, 164.07, 177,
604/162, 512
See application file for complete search history.

(56) References Cited

U.S. PATENT DOCUMENTS 5,356,389 A    10/1994  Willing
6,638,252 B2   10/2003  Moulton et al.
(Continued)

FOREIGN PATENT DOCUMENTS

JP         6-7441 A    1/1994
JP      10-179734 A    7/1998
(Continued)

OTHER PUBLICATIONS

International Search Report (PCT/ISA/210) for PCT/JP2008/055697 completed Jun. 12, 2008.
Written Opinion (PCT/ISA/237) for PCT/JP2008/055697 completed Jun. 12, 2008.

*Primary Examiner* — Nicholas Lucchesi
*Assistant Examiner* — Brooke Matney
(74) *Attorney, Agent, or Firm* — Buchanan Ingersoll & Rooney PC

(57) ABSTRACT

An indwelling needle assembly has a hollow outer needle, an outer-needle hub fixed to the base end of the outer needle, an inner needle inserted into the outer needle, an inner-needle hub fixed to the base end of the inner needle, a tube connected to the base end (or a side section) of the outer-needle hub so that the inner cavity of the tube is communicated with the inner cavity of the outer needle, and a protector that, when the inner needle is removed from the outer needle, covers at least the point of the inner needle and disconnectably connected to the outer-needle hub. A finger hold is formed in a projecting manner on a protector cover of the protector, and the finger hold is pressed by a finger to move the outer needle in the direction of its tip relative to the inner needle. The finger hold is formed in a shape that, when the outer needle is moved in the direction of its tip relative to the inner needle, causes force applied in the direction in which the finger hold projects relative to the center axis of the outer needle to act on the finger hold.

11 Claims, 31 Drawing Sheets

(56) References Cited

U.S. PATENT DOCUMENTS

| | | |
|---|---|---|
| 6,749,588 B1 * | 6/2004 | Howell et al. ............ 604/164.08 |
| 6,953,448 B2 | 10/2005 | Moulton et al. |
| 7,060,060 B1 * | 6/2006 | Simpson et al. .............. 604/537 |
| 7,226,431 B1 * | 6/2007 | Bell-Greenstreet ........... 604/110 |
| 2004/0204691 A1 | 10/2004 | Yashiro et al. |

FOREIGN PATENT DOCUMENTS

| | | |
|---|---|---|
| JP | 2002-126080 A | 5/2002 |
| JP | 2004-305467 A | 11/2004 |
| JP | 2005-261931 A | 9/2005 |

\* cited by examiner

INDWELLING NEEDLE ASSEMBLY

TECHNICAL FIELD

The present invention relates to an indwelling needle assembly, which is made to puncture a blood vessel and indwell there, for example, when an infusion is performed.

BACKGROUND ART

At the time of carrying out an infusion on a patient, or in other similar situations, an indwelling needle connected to an infusion line is made to puncture a blood vessel and indwell there, thereby performing the infusion operation.

Such an indwelling needle is composed of a hollow outer needle, an outer-needle hub firmly attached to a proximal end (base end) of the outer needle, an inner needle inserted into the outer needle and having a sharp point at a distal end (tip) thereof, and an inner-needle hub firmly attached to a proximal end (base end) of the inner needle (see, for example, Patent Document 1).

When the indwelling needle is made to puncture a patient's blood vessel, a puncturing operation is performed in an assembled condition, where the inner needle is inserted into the outer needle and the point of the inner needle protrudes from the distal end of the outer needle. In such an assembled condition, generally, a connector of an infusion line is connected with the outer-needle hub.

Then, when the point of the inner needle has reached the inside of the blood vessel, blood having flowed in through the opening at the point passes through the inner cavity (lumen) of the inner needle, and flows into the inside of the transparent inner-needle hub (flashback). This makes it possible to confirm (visually recognize) that the inner needle has securely punctured the blood vessel.

Upon confirmation of flashback, the outer needle is advanced, with the inner needle as a guide, so as to become inserted into (puncture) the blood vessel.

Next, while gripping the outer needle by hand, the inner needle is pulled out of the outer needle. Then, an infusion agent is administered through the connected infusion line and the outer needle.

Meanwhile, the outer-needle hub is formed with a finger hold (tab), which is pressed by a finger (index finger) in order to move the outer needle in the distal direction. The finger hold is formed perpendicular to the axis of the outer needle, and a surface thereof on the proximal side is pressed by the finger.

In the aforementioned existing indwelling needle assembly, however, the finger hold is oriented vertically to the axis of the outer needle, and hence, the following problem has occurred. When the outer needle is moved in the distal direction, an attempt to press the finger hold straight along the axis of the outer needle, namely, in a direction parallel to the axis may result in a force, which acts in a downward direction relative to the axis (in a direction opposite to the direction of projection of the finger hold), thus causing an inconvenience such as bending of the outer needle, and making it difficult to move (advance) the outer needle smoothly. In short, the indwelling needle assembly has been poor in operability at the time of performing a puncturing operation.

Further, in the existing indwelling needle assembly, an attempt to move the outer needle in parallel with the axis thereof when the outer needle is moved in the distal direction may result in a force being exerted in a downward direction relative to the axis, thus causing an inconvenience in that a distal-side portion of the axis of the outer needle becomes inclined downwardly (downward deviation), or the outer needle becomes bent. Thus, it has sometimes been difficult to move (advance) the outer needle smoothly. In short, in this case as well, the indwelling needle assembly has been poor in operability at the time of performing a puncturing operation.

Patent Document 1: Japanese Laid-Open Patent Publication No. 10-179734

DISCLOSURE OF INVENTION

An object of the present invention is to provide an indwelling needle assembly, which is excellent in operability at the time of performing a puncturing operation.

In order to attain the above object, according to the present invention, there is provided an indwelling needle assembly, including:

an inner needle having a sharp point at a distal end;

an inner-needle hub fixed to a proximal portion of the inner needle;

a hollow outer needle in which the inner needle is inserted;

an outer-needle hub fixed to a proximal portion of the outer needle;

a protector detachably connected to the outer-needle hub; and a finger hold provided on the outer-needle hub or the protector, the finger hold being pressed by a finger to move the outer needle in the distal direction relative to the inner needle, wherein the finger hold has a shape such that, when the outer needle is moved in the distal direction relative to the inner needle, a force in an upward direction relative to an axis of the outer needle can act on the finger hold.

This ensures that, when the outer needle is moved in the distal direction relative to the inner needle during a puncturing operation, the finger hold can be pressed by a finger in the distal direction, while lifting up (in the manner of lifting up) the finger hold in a projecting direction thereof. This makes it possible to move the outer needle straightly along its axis, namely, to move the outer needle along the direction of its axis without bending the outer needle, thereby moving (advancing) the outer needle smoothly. As a result, excellent operability can be ensured, and securing of a line, such as an infusion line or the like, can be performed easily and assuredly.

In the indwelling needle assembly according to the present invention, preferably, the finger hold is disposed so as to project in an upward direction.

This makes it possible to smoothly move the outer needle in the distal direction relative to the inner needle.

In the indwelling needle assembly according to the present invention, preferably, upon pulling of the inner needle out of the outer needle, the protector covers at least the point of the inner needle.

This ensures that, when the inner needle is disposed of or the like, the operator can be prevented from piercing his or her finger with the point by mistake.

In the indwelling needle assembly according to the present invention, preferably, the finger hold has on the proximal side a finger hold surface on which to place a finger, and the finger hold surface has a portion the normal of which is directed toward the side of the axis of the outer needle.

This permits the outer needle to be moved more smoothly in the distal direction relative to the inner needle.

In the indwelling needle assembly according to the present invention, preferably, the finger hold has on the proximal side a finger hold surface on which to place a finger, and the finger hold surface has a surface, which is oriented at an angle of less than 90° with respect to the axis of the outer needle.

This ensures that the outer needle can be moved more smoothly in the distal direction relative to the inner needle.

In the indwelling needle assembly according to the present invention, preferably, the finger hold has on the proximal side a finger hold surface on which to place a finger, and the finger hold surface is provided with an anti-slipping means for the finger.

This ensures that the finger can be prevented from slipping, and the outer needle can be moved assuredly.

In the indwelling needle assembly according to the present invention, preferably, the anti-slipping means comprises a rugged pattern formed on the finger hold surface.

This ensures that the finger can be prevented from slipping, and the outer needle can be moved assuredly.

In the indwelling needle assembly according to the present invention, preferably, the finger hold has a reinforcement section for suppressing bending when the finger hold is pressed by a finger.

This ensures that operability of the finger hold can be prevented from becoming degraded, when the outer needle is moved in the distal direction relative to the inner needle.

In the indwelling needle assembly according to the present invention, preferably, the finger hold has on the proximal side a finger hold surface on which to place a finger; and the reinforcement section comprises a rib, which is formed on an opposite side from the finger hold surface.

This makes it possible to prevent operability of the finger hold from becoming degraded, when the outer needle is moved in the distal direction relative to the inner needle.

The indwelling needle assembly according to the present invention, preferably, has a seal member, which is provided in the outer-needle hub and is formed with a hole or slit for permitting the inner needle to be passed therethrough, with the hole or slit becoming closed when the inner needle having passed therethrough is pulled out.

This makes it possible to prevent leakage of liquid from the outer-needle hub, and to maintain sterility inside the outer-needle hub, upon pulling out the inner needle.

The indwelling needle assembly according to the present invention, preferably, has an opening, which is provided in a proximal portion or a side section of the outer-needle hub, and which communicates with the inner cavity of the outer needle.

This makes it possible to supply the outer needle with a liquid, such as a liquid drug.

In the indwelling needle assembly according to the present invention, preferably, a tube is connected to the opening.

This ensures that the outer needle can be supplied with a liquid, such as a liquid drug, through the tube.

In the indwelling needle assembly according to the present invention, preferably, the tube is passed through the inner-needle hub.

This makes it possible to prevent the tube from obstructing operations of the indwelling needle assembly.

Further, in order to attain the above object, according to the present invention, there is provided an indwelling needle assembly including:

an inner needle having a sharp point at a distal end;

an inner-needle hub fixed to a proximal portion of the inner needle;

a hollow outer needle in which the inner needle is inserted;

an outer-needle hub fixed to a proximal portion of the outer needle; and a protector detachably connected to the outer-needle hub and which, upon pulling of the inner needle out of the outer needle, covers at least the point of the inner needle, wherein the inner-needle hub has a support section configured to support a supported section formed in the protector and/or the outer-needle hub, and wherein, when the outer needle is moved in the distal direction relative to the inner needle, the support section supports the supported section so as to inhibit the axis of the outer needle from becoming inclined.

This ensures that when moving the outer needle in the distal direction relative to the inner needle during a puncturing operation, the outer needle can be moved straightly along its axis, namely, the outer needle is moved along the direction of its axis without being bent. This enables the outer needle to be moved (advanced) smoothly. As a result, excellent operability can be ensured, and securing of a line, such as an infusion line, can be performed easily and assuredly.

In the indwelling needle assembly according to the present invention, preferably, the assembly includes a finger hold provided on the outer-needle hub or the protector, and which is pressed by a finger so as to move the outer needle in the distal direction relative to the inner needle, and the support section inhibits a distal-side portion of the axis of the outer needle from being slanted toward the opposite side of the finger hold, relative to the axis of the outer needle, in a condition before the finger hold is pressed.

This makes it possible to move the outer needle more smoothly in the distal direction relative to the inner needle.

In the indwelling needle assembly according to the present invention, preferably, the assembly includes a finger hold provided on the outer-needle hub or the protector, and which is pressed by a finger to move the outer needle in the distal direction relative to the inner needle, and the support section includes a first wall portion configured to make contact with an outer surface on a finger hold side of the supported section, and a second wall portion configured to make contact with an outer surface on an opposite side from the finger hold of the supported section.

This permits the outer needle to be moved more smoothly in the distal direction relative to the inner needle.

In the indwelling needle assembly according to the present invention, preferably, the second wall section is provided at a distal portion of the inner-needle hub.

This ensures that, from a condition in which the inner needle is inserted into the outer needle and the point of the inner needle protrudes from a distal opening of the outer needle, the supported section remains in contact with the second wall portion until the supported section becomes disengaged from the protector. This, in turn, ensures that the outer needle can be moved more smoothly in the distal direction relative to the inner needle.

In the indwelling needle assembly according to the present invention, preferably, a length of the second wall portion in the axial direction of the outer needle is not less than 1 mm.

This ensures that sufficient strength can be obtained.

In the indwelling needle assembly according to the present invention, preferably, the first wall portion ranges from a distal portion of the inner-needle hub to a portion corresponding to a proximal portion of the supported section, in a condition where the inner needle is inserted into the outer needle and the point protrudes from a distal opening of the outer needle.

This ensures that, from a condition in which the inner needle is inserted into the outer needle and the point of the inner needle protrudes from a distal opening of the outer needle, the proximal portion of the supported section remains in contact with the first wall portion until the supported section is disengaged from the protector. This in turn enables the outer needle to be moved more smoothly in the distal direction relative to the inner needle.

In the indwelling needle assembly according to the present invention, preferably, the first wall portion and the second wall portion are each in contact with the supported section, in a condition where the inner needle is inserted into the outer needle and the point protrudes from a distal opening of the outer needle.

This makes it possible to move the outer needle more smoothly in the distal direction relative to the inner needle.

In the indwelling needle assembly according to the present invention, preferably, the finger hold is formed so as to project on the outer-needle hub and the protector.

This ensures that an operation for moving the outer needle relative to the inner needle can be performed more easily.

In the indwelling needle assembly according to the present invention, preferably, the support section supports the supported section until the outer needle is moved by a distance of at least half the length of the outer needle, starting from a condition in which the inner needle is inserted into the outer needle and the point protrudes from a distal opening of the outer needle.

This makes it possible to more assuredly prevent the axis of the outer needle from becoming inclined, when the outer needle is moved in the distal direction relative to the inner needle.

In the indwelling needle assembly according to the present invention, preferably, the supported section is located inside the inner-needle hub, in a condition where the inner needle is inserted into the outer needle and the point protrudes from a distal opening of the outer needle, and an outer surface of the supported section and an inner surface of the support section each comprises an arcuate portion.

This makes it possible for the supported section to be supported more securely by the support section, and to more assuredly prevent the axis of the outer needle from becoming inclined when the outer needle is moved in the distal direction relative to the inner needle.

The indwelling needle assembly according to the present invention, preferably, has a seal member, which is provided in the outer-needle hub, and is formed with a hole or slit for permitting the inner needle to be passed therethrough, with the hole or slit becoming closed when the inner needle is pulled out.

This makes it possible to prevent leakage of liquid from the outer-needle hub, and to maintain sterility inside of the outer-needle hub when the inner needle is pulled out.

The indwelling needle assembly according to the present invention, preferably, has an opening, which is provided in a proximal portion or a side section of the outer-needle hub, and which communicates with the inner cavity of the outer needle.

This makes it possible to supply the outer needle with a liquid, such as a liquid drug.

In the indwelling needle assembly according to the present invention, preferably, a tube is connected to the opening.

This ensures that the outer needle can be supplied with a liquid, such as a liquid drug, through the tube.

In the indwelling needle assembly according to the present invention, preferably, the tube is passed through the inner-needle hub.

This makes it possible to prevent the tube from obstructing operations of the indwelling needle assembly.

BEST MODE FOR CARRYING OUT THE INVENTION

The indwelling needle assembly according to the present invention will be described in detail below, based on preferred embodiments of the invention, as shown in the accompanying drawings.

<First Embodiment>

Figure 1:
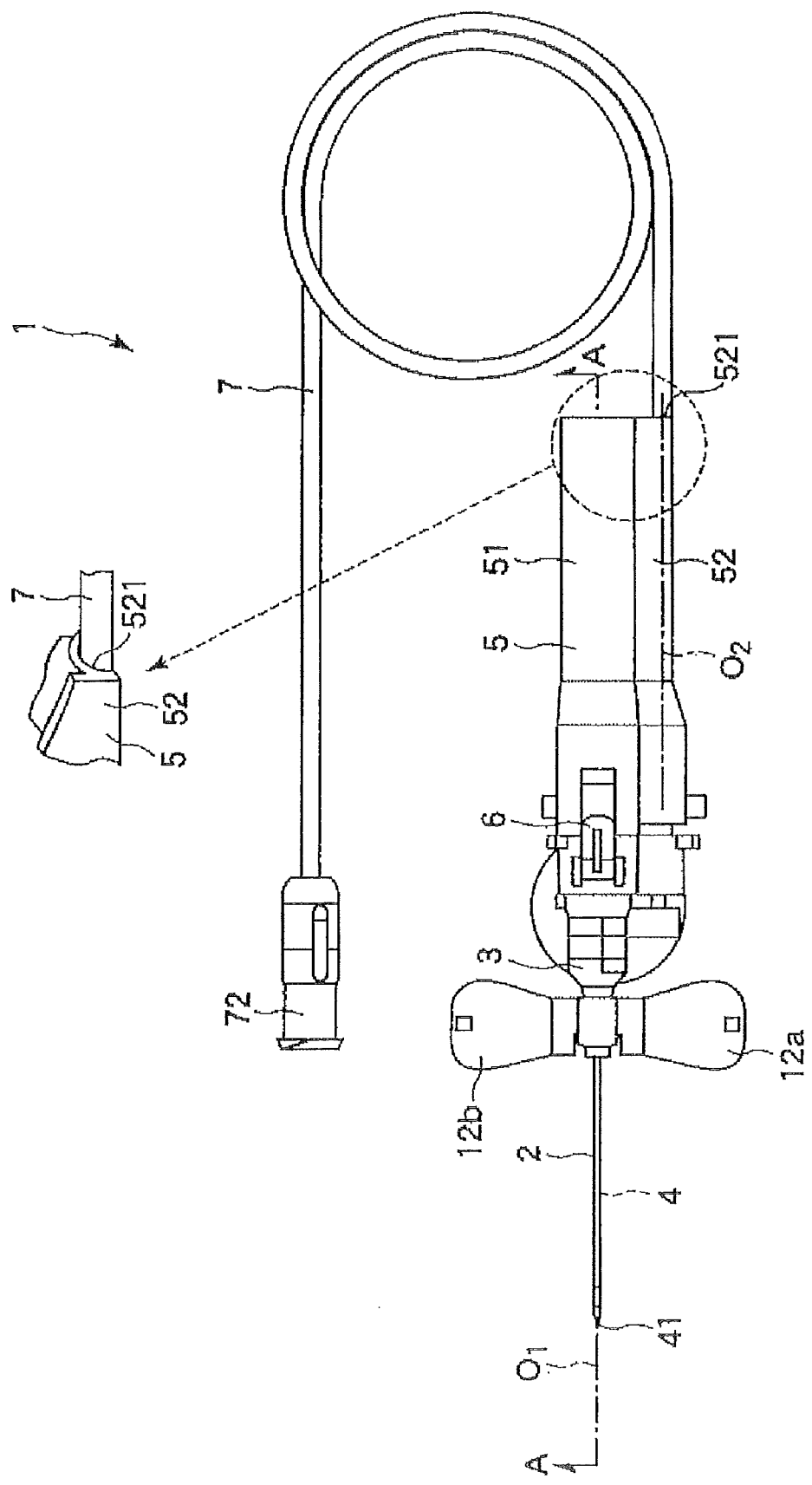
FIG. 1 is a perspective view of a first embodiment of an indwelling needle assembly according to the present invention.
Figure 2:
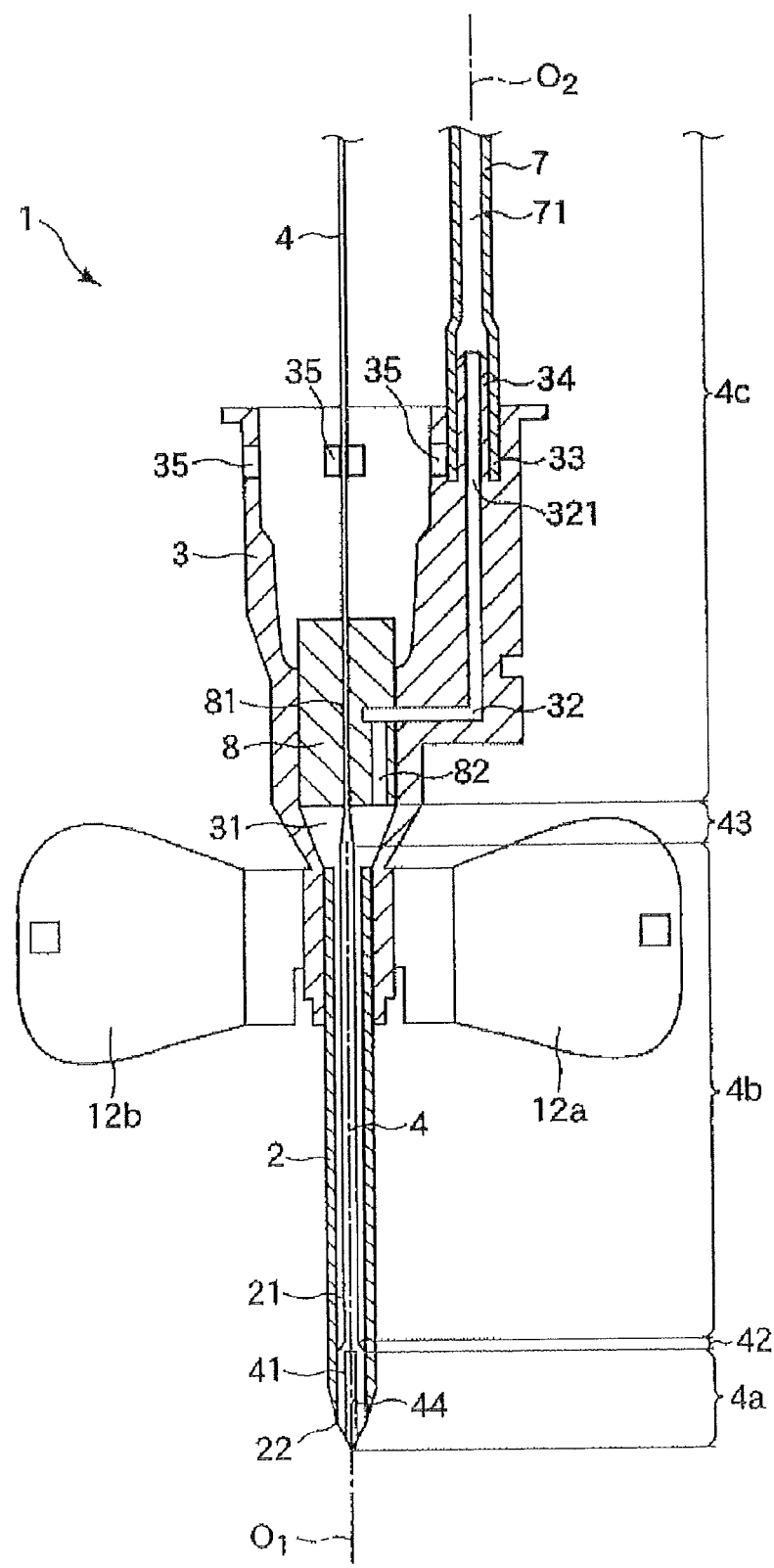
FIG. 2 is a sectional view showing an outer needle, an outer-needle hub, an inner needle, and a tube of the indwelling needle assembly shown in FIG. 1.
Figure 3:
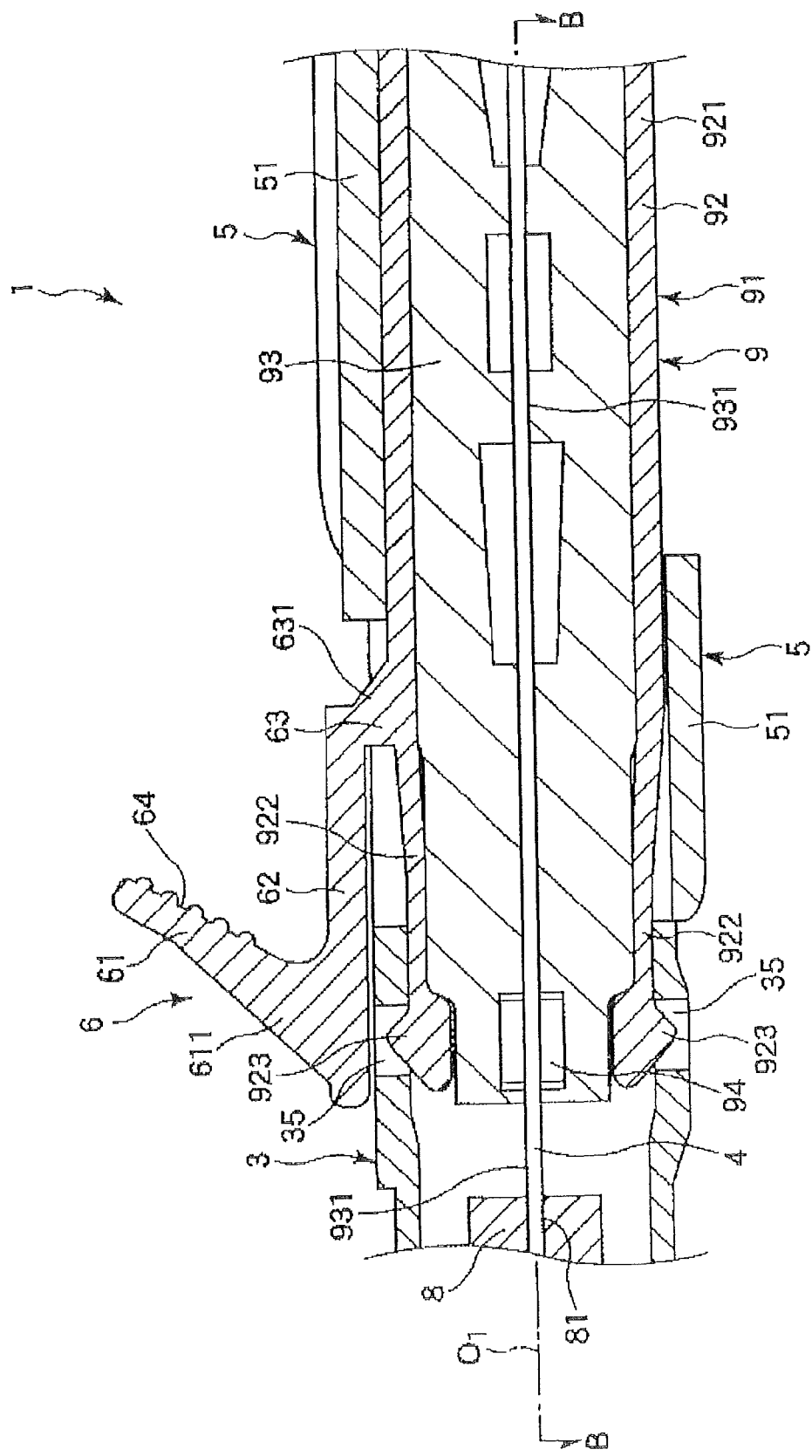
FIG. 3 is a sectional view taken along line A-A of FIG. 1.
Figure 4:
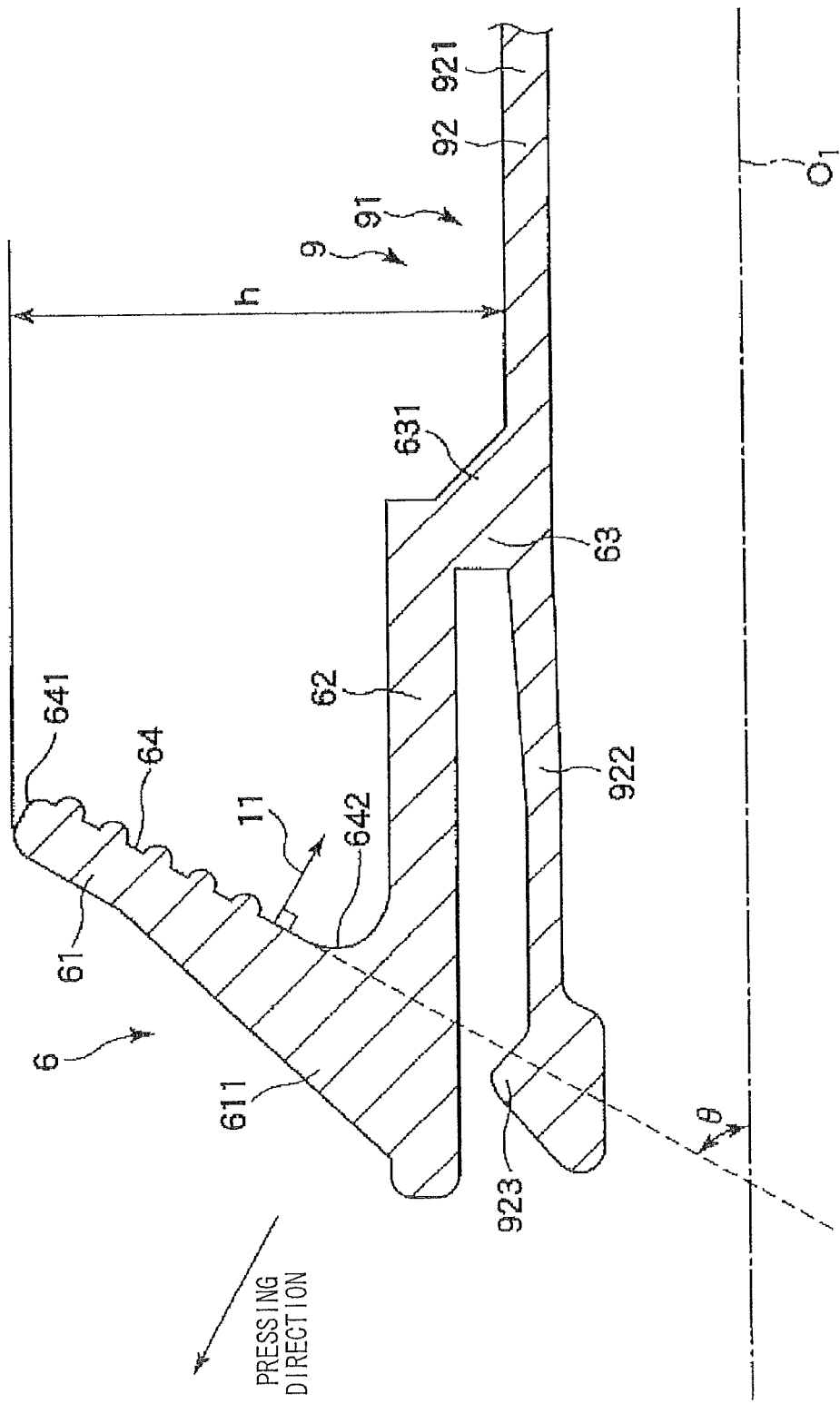
FIG. 4 is a sectional view (i.e., a sectional view taken along line A-A) of a finger hold of the indwelling needle assembly shown in FIG. 1.
Figure 5:
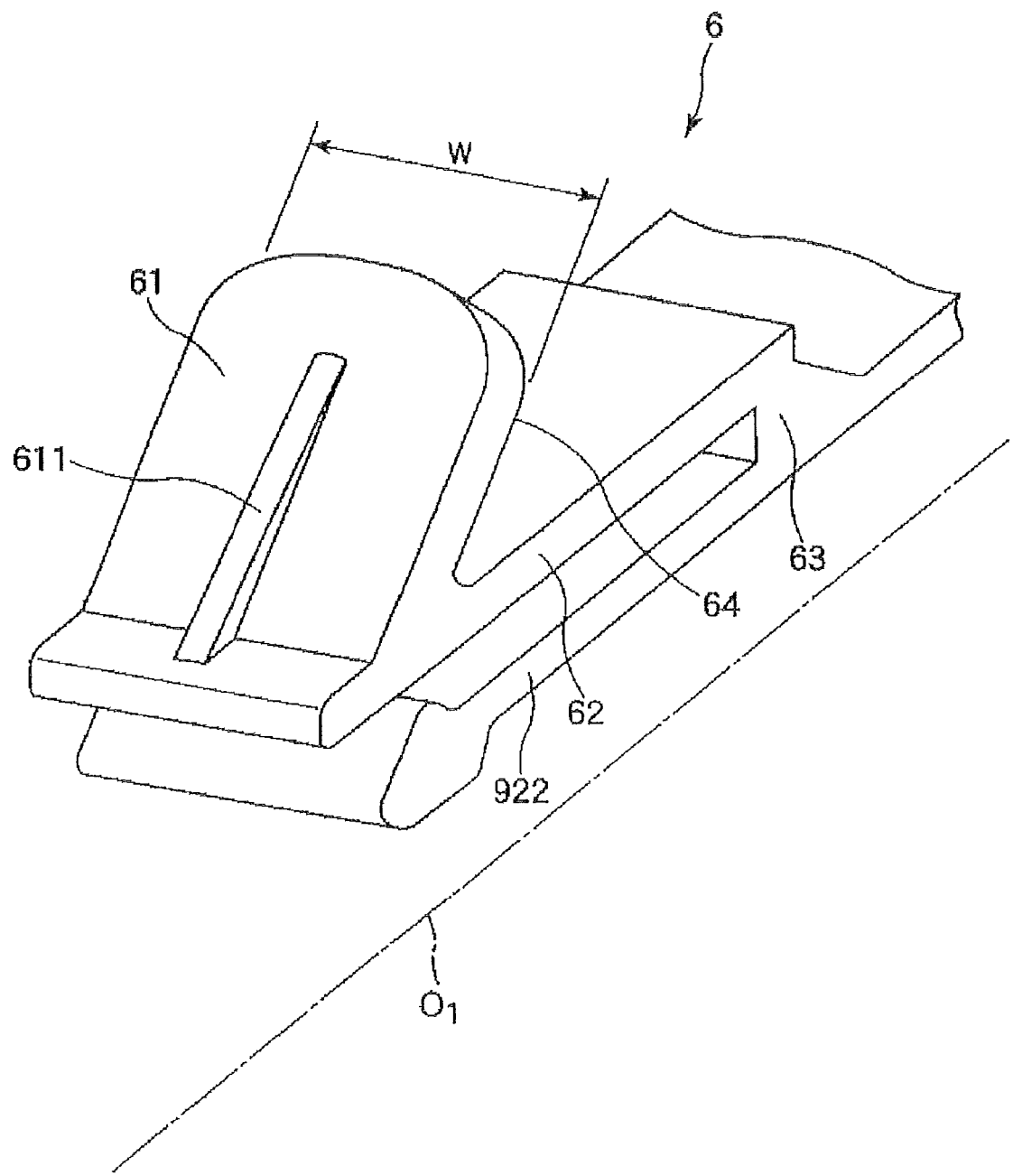
FIG. 5 is a perspective view of the finger hold of the indwelling needle assembly shown in FIG. 1.
Figure 6:
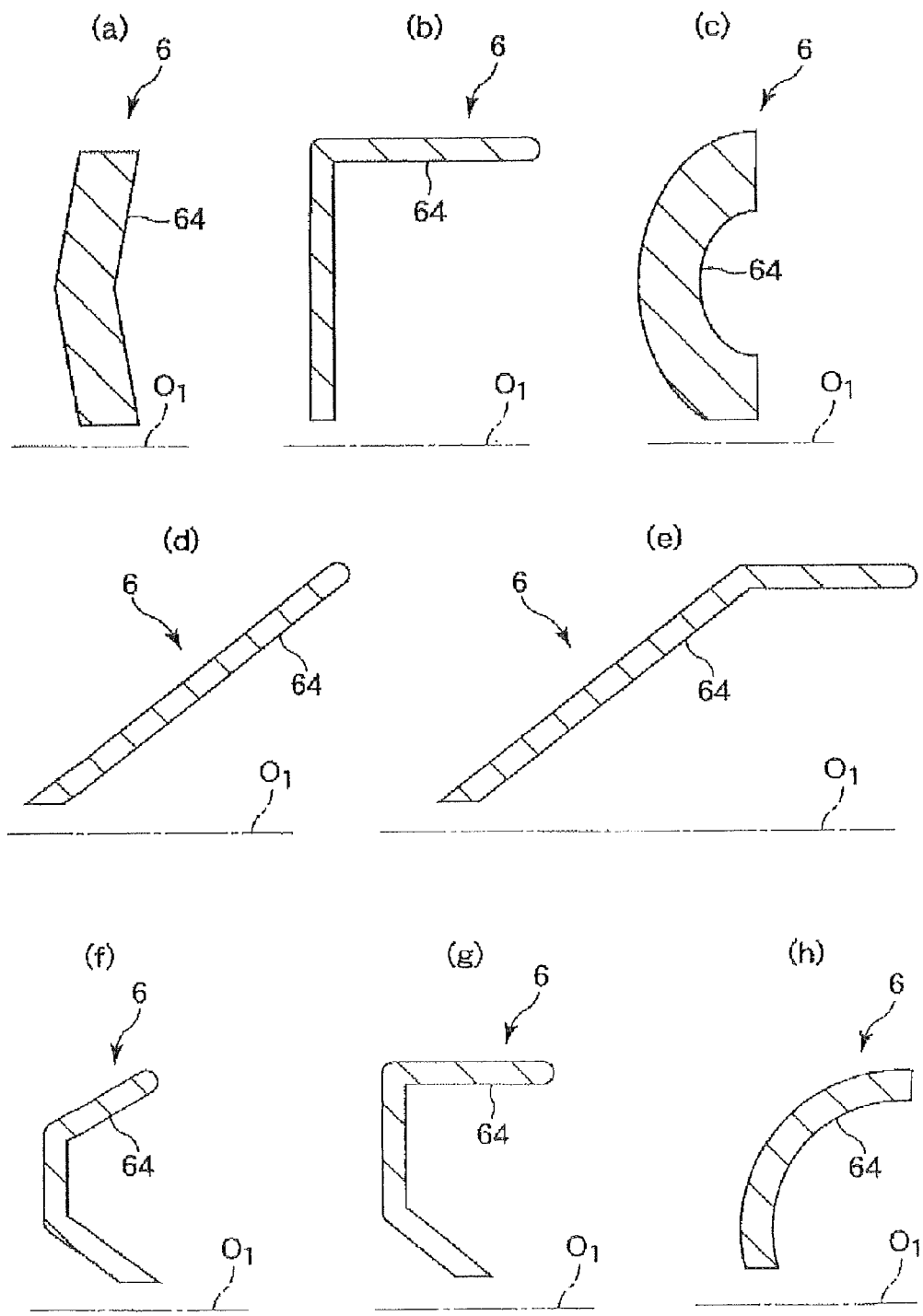
FIG. 6 shows sectional views illustrating other configuration examples of the finger hold of the indwelling needle assembly shown in FIG. 1.

FIG. 1 is a plan view showing a first embodiment of the indwelling needle assembly according to the present invention; FIG. 2 is a sectional view showing an outer needle, an outer-needle hub, an inner needle, and a tube in the indwelling needle assembly shown in FIG. 1; FIG. 3 is a sectional view taken along line A-A of FIG. 1; FIG. 4 is a sectional view (i.e., a sectional view taken along line A-A) of a finger hold of the indwelling needle assembly shown in FIG. 1; FIG. 5 is a perspective view of the finger hold of the indwelling needle assembly shown in FIG. 1; FIG. 6 shows sectional views illustrating other configuration examples of the finger hold of the indwelling needle assembly shown in FIG. 1; FIGS. 7 to 11 each are sectional views taken along line B-B of FIG. 3; and FIG. 12 is a perspective view of a link member of the indwelling needle assembly shown in FIG. 1.

Incidentally, hereinafter, descriptions shall be made while referring to the right side in FIG. 1 and FIGS. 3 to 12 as "proximal," the left side as "distal," the upper side in FIG. 2 as "proximal," and the lower side as "distal." In addition, in FIGS. 7 to 11, the inner-needle hub is omitted from the drawings. Further, the inner needle also is shown to be constant in outside diameter, in figures other than FIG. 2.

The indwelling needle assembly 1 shown in each of the figures composes a hollow outer needle 2, an outer-needle hub 3 fixed to a proximal portion of the outer needle 2, an inner needle 4, which is inserted into the outer needle 2, an inner-needle hub 5 fixed to a proximal portion of the inner needle 4, and a tube 7 connected to a proximal portion (or a side section) of the outer-needle hub 3, so that an inner cavity 71 thereof communicates with an inner cavity 21 of the outer needle 2. Configurations of each of these components will be described in detail below.

As the outer needle 2, a needle that has a certain degree of bendability preferably is used. The material constituting the outer needle 2 is preferably a resin material, particularly a soft resin material. Examples of such soft resin materials include fluororesins such as PTFE, ETFE, PFA, etc., olefin reins such as polyethylene, polypropylene, etc., mixtures of olefin resins, polyurethane, polyesters, polyamides, polyether nylon resins, mixtures of the olefin resin with ethylene-vinyl acetate copolymer, etc.

A portion or the entirety of the outer needle 2 may enable the inside thereof to be visible. Further, the material constituting the outer needle 2 may have blended therein a radiopaque agent such as, for example, barium sulfate, barium carbonate, bismuth carbonate or tungstic acid, so as to have a radiopaque property.

To a proximal portion of the outer needle 2, the outer-needle hub 3 is firmly attached (fixed) in a liquid-tight fashion, for example, by a method such as caulking, fusing (heat fusing, ultrasonic fusing, or the like), adhesion with an adhesive, etc.

The outer-needle hub 3 is composed of a substantially tubular member, the interior 31 of which communicates with the inner cavity 21 of the outer needle 2.

The outer-needle hub 3 is formed, in a portion on the right side in FIG. 2, with a channel 32, which opens at one end thereof into the interior 31 of the outer-needle hub 3. The channel 32 is substantially L-shaped, and the other end thereof opens into a recess 33, which is formed in a hollow or recessed fashion at the proximal end of the outer-needle hub 3, thereby forming an opening 321. In addition, at a distal surface (bottom surface) of the recess 33, a ring-shaped projected portion (connecting portion) 34 is formed, so as to surround the opening 321 and project in the proximal direction.

The projected portion 34 is inserted into the inner cavity 71 of a distal portion of the tube 7, and one end portion (distal portion) of the tube 7 is connected to the outer-needle hub 3. This makes it possible to supply the outer needle 2 (outer-needle hub 3) with a liquid, such as a liquid drug, via the tube 7.

In addition, on the left and right sides of the outer-needle hub 3, as shown in FIG. 2, a pair of wings 12a and 12b are formed integrally with the outer-needle hub 3. The wings 12a and 12b are each bendable, and can be opened and closed through bending or curving of the portions near the joints of the wings 12a and 12b with the outer-needle hub 3.

When the outer needle 2 and the inner needle 4 are made to puncture a blood vessel or the like, the wings 12a and 12b are pinched with fingers into a closed state, whereby the puncturing operation can be performed. Alternately, a method can be adopted in which puncturing is conducted by pinching the inner-needle hub 5 by a thumb and a middle finger, instead of pinching the wings 12a and 12b, and after the distal end of the outer needle 2 enters the blood vessel, a finger hold 6 (described later) is pressed by an index finger so as to push the outer-needle hub 3 forward, thereby advancing only the outer needle 2 into the blood vessel. When the outer needle 2 is left to indwell, the wings 12a and 12b are set into an opened state, and the wings 12a and 12b in the opened state are fixed to the skin by a pressure sensitive adhesive tape or the like.

In addition, in a proximal portion of the outer-needle hub 3, four holes (recesses) 35 are formed at regular angular intervals, into which projections 923 of four projected sections 922 of a protector cover 92 of a protector 9 (to be described later) may be inserted.

The inner needle 4 provided with a sharp point 41 at its distal end is inserted into the outer needle 2. The indwelling needle assembly 1 is used in a condition whereby the inner needle 4 is inserted into the outer needle 2, and where the inner-needle hub 5 (described later) and the outer-needle hub 3 are maintained in contact with each other (i.e., a condition where the point 41 protrudes from the distal opening 22 of the outer needle 2), namely, the condition shown in FIGS. 1 and 2. Hereinafter, such a condition will be referred to as an "assembled condition."

The length of the inner needle 4 is set to a given length, so that at least the point 41 thereof protrudes from the distal opening 22 of the outer needle 2 in the assembled condition.

The inner needle 4 may be a hollow needle or a solid needle. When the inner needle 4 is a solid needle, sufficient strength can be secured while keeping the outside diameter of the needle small. Further, if the inner needle 4 is a solid needle, when the inner needle 4 is disposed of after completion of an operation thereof, there is no danger of blood remaining inside the inner needle 4, or that blood might flow out therefrom, and high safety is therefore secured.

When the inner needle 4 is a hollow needle, puncturing of a blood vessel by the inner needle 4 results in blood flowing into the hollow section of the inner needle 4, whereby flashback of the blood can be confirmed. In this connection, when the inner needle 4 is a solid needle, blood flows into a gap formed between the inner needle 4 and the outer needle 2, which enables flashback of the blood to be confirmed earlier.

Incidentally, the inner needle 4 may have a configuration in which the inner needle 4 has both a hollow section and a solid section (for example, a configuration in which the needle is hollow on the distal side and solid on the proximal side, the configuration being obtained by filling a portion of the inner cavity of a hollow needle). In this connection, when the inner needle 4 is entirely composed of a single member, the inner needle 4 can be reduced in cost.

In addition, although the inner needle 4 may have a constant outside diameter, in the configuration shown in the figures, the inner needle 4 has a plurality of (in this embodiment, three) sections, which differ in outside diameter. More specifically, the inner needle 4 has a maximum outside diameter section 4a having a maximum outside diameter provided on the distal side (distal-portion side), a minimum outside diameter section 4c having a minimum outside diameter provided on the proximal side, and an intermediate outside diameter section 4b having an intermediate outside diameter, between the maximum diameter and the minimum diameter, provided between the maximum diameter section 4a and the minimum outside diameter section 4c.

Further, the inner needle 4 has a first varying outside diameter section 42, provided at a joint between the maximum outside diameter section 4a and the intermediate outside diameter section 4b, and having a continuously varying outside diameter. The inner needle 4 also has a second varying outside diameter section 43, provided between the intermediate outside diameter section 4b and the minimum outside diameter section 4c, and having a continuously varying outside diameter.

At each of the varying outside diameter sections 42 and 43, the outside diameter of the inner needle 4 may vary in a stepwise manner. However, preferably, the outside diameter varies continuously (in a tapered fashion). The latter configuration ensures that when the inner needle 4 is pulled out of the outer needle 2, each of the varying outside diameter sections 42 and 43 can be prevented from becoming caught on a distal edge portion of a slit 81 in a seal member 8 (described later), or on a protector 9 (described later) or the like. Therefore, the operation of pulling the inner needle 4 out of the outer needle 2 can be carried out more smoothly and assuredly.

Incidentally, the varying outside diameter sections 42 and 43 each may be formed simultaneously with manufacturing of the inner needle 4. Alternatively, each may be formed by utilizing a step, which necessarily is carried out at the time of forming a groove 44 (described later).

In addition, the maximum outside diameter section 4a has an outside diameter set nearly equal to the inside diameter of the outer needle 2, so that the maximum outside diameter section 4a makes close contact with an inner surface of the outer needle 2 in a condition in which the inner needle 4 is inserted into the outer needle 2. The maximum outside diameter section 4a (distal portion) is provided on an outer peripheral portion thereof with the groove (channel) 44, in a recessed or hollowed form, provided along the longitudinal direction of the inner needle 4. The groove 44 ensures that the distal opening 22 of the outer needle 2 and the inner cavity 31 of the outer-needle hub 3 communicate with each other in a condition where the inner needle 4 is inserted into the outer needle 2. The groove 44 functions as a channel (flow passage) for blood (body fluid) upon puncturing of a blood vessel, for example. Consequently, flashback of the blood can be confirmed assuredly.

Examples of the material constituting the inner needle 4, as described above, include metallic materials such as stainless steel, aluminum, aluminum alloys, titanium, titanium alloys, etc.

The inner-needle hub 5 is firmly attached (fixed) to a proximal portion of the inner needle 4. The inner-needle hub 5 has a protector accommodating section (link member accommodating section) 51, in which the inner needle 4 is inserted, and in which the protector 9 and a link member 20, to be described later, are accommodated (disposed) in the assembled condition, and a tube accommodating section 52, which is provided on a lateral side (the lower side in FIG. 1) of the protector accommodating section 51, and in which the distal side of the tube 7 is accommodated (disposed) in the assembled condition.

The protector 9 and the link member 20 can each be moved relative to the protector accommodating section 51.

Further, in the assembled condition, the tube 7 is inserted into the inner-needle hub 5, whereby the tube 7 can be prevented from obstructing operations of the indwelling needle assembly 1.

The tube accommodating section 52 is formed with a groove 521, and the tube 7 is disposed in the groove 521.

A part defining (constituting) the groove 521 functions as a guide means for guiding the tube 7. The guide means, or the part defining the groove 521, guides the tube 7, so that a center axis (axis) $O_2$ at a distal portion of the tube 7 will be substantially parallel to the longitudinal direction of the inner-needle hub 5 (the center axis $O_1$ of the outer needle 2).

Thus, the tube 7 is connected to a proximal portion of the outer-needle hub 3 so that, in the assembled condition, the center axis $O_1$ of the outer needle 2 and the center axis $O_2$ at the proximal portion of the tube 7 are arranged substantially parallel to each other. In other words, the tube 7 protrudes in the proximal direction from the proximal end of the outer-needle hub 3.

In addition, upon removing the tube 7 from the inner-needle hub 5 when the inner needle 4 is pulled out from the outer needle 2, the tube 7 can be removed easily and speedily due to the presence of the groove 521 (through the groove 521).

Examples of methods for fixing the inner needle 4 to the inner-needle hub 5 include fitting, caulking, fusing, adhesion with an adhesive, etc., and combinations thereof. Moreover, when the inner needle 4 is a hollow needle, it is necessary to provide sealing, so that blood flowing backward upon puncturing a blood vessel, for example, is prevented from flying out from the proximal end of the inner needle 4.

Each of the inner-needle hub 5 and the outer-needle hub 3 as described above preferably is formed from a transparent (colorless transparent), colored transparent, or semi-transparent resin, whereby visibility of the interiors thereof is secured. This ensures that upon securely puncturing a blood vessel by the outer needle 2, flashback of blood flowing in through the groove 44 in the aforementioned inner needle 4 can be visually confirmed. Further, when the inner needle 4 is solid, flashback of the blood due to pressure inside the blood vessel, for example, flows backward through the groove 44, which enables better visibility of the flashback.

The materials constituting the outer-needle hub 3, the inner-needle hub 5, and the wings 12a and 12b are not particularly limited. Examples of such materials include various resin materials such as polyolefins such as polyethylene, polypropylene, ethylene-vinyl acetate copolymer, etc., polyurethane, polyamides, polyesters, polycarbonate, polybutadiene, polyvinyl chloride, and polyacetal.

The tube 7 is bendable, and is connected at one end portion thereof to a proximal portion of the outer-needle hub 3, as mentioned above. The other end portion (proximal portion) of the tube 7 is connected to a connector 72. The connector 72 is connected, for example, to another connector provided at an end portion of an infusion line for supplying an infusion (liquid drug) to be administered, or to a mouth portion (distal portion) of a syringe filled with a liquid drug, or the like.

Incidentally, the materials constituting the tube 7 are not particularly limited. Examples of such materials include polyolefins such as polyethylene, polypropylene, ethylene-vinyl acetate copolymer, etc., polyvinyl chloride, polybutadiene, polyamides, and polyesters, among which particularly preferred is polybutadiene. When polybutadiene is used as the material constituting the tube 7, appropriate bendability and chemical resistance can be obtained, together with excellent anti-adsorption effects on chemicals.

Further, the indwelling needle assembly 1 has a cylindrical (block-like) seal member 8 provided at the inside 31 of the outer-needle hub 3. The seal member 8 is formed with a hole or slit through which the inner needle 4 can be passed, and which becomes closed when the thus passed inner needle 4 is pulled out. In the present embodiment, the seal member 8 is formed substantially in its center with a slit 81, which pierces the seal member 8 along the longitudinal direction of the seal member 8.

The slit 81 is formed as a straight line in shape. This permits the slit 81 to remain in a closed state and to be easily placed in an open state. Therefore, the inner needle 4 can be passed smoothly through the seal member 8 (the slit 81). In other words, as will be described later, when the outer needle 2 is advanced using the inner needle 4 as a guide, frictional resistance between the outer surface of the inner needle 4 (the minimum outside diameter section 4*c*) and the inner surface of the slit 81 can be reduced. Consequently, operability of the indwelling needle assembly 1 when performing a puncturing operation can be enhanced.

The seal member 8 has a self-closing property, such that the inner needle 4 passes through the slit 81 in the assembled condition, and further, upon pulling out of the inner needle 4 thus passed, the slit 81 becomes closed by the elastic force (restoring force) of the seal member 8. This ensures that, upon pulling out of the inner needle 4, leakage of liquid from the proximal end of the outer-needle hub 3 can be prevented, and sterility inside the outer-needle hub 3 can be maintained.

Further, as shown in FIG. 2, in the assembled condition, the minimum outside diameter section 4*c* of the inner needle 4 is located within the slit 81. This ensures a reduced area of contact between the outer surface of the minimum outside diameter section 4*c* and the inner surface of the slit 81, whereby the frictional resistance therebetween can be reduced. In addition, it is possible to prevent the seal member 8 (slit 81) from acquiring a certain (deformed) shape, which tends to lower the sealing performance thereof.

Examples of the materials constituting the seal member 8 include a variety of elastic materials, such as various rubber materials (particularly those which have undergone a vulcanizing treatment) such as natural rubber, isoprene rubber, butyl rubber, butadiene rubber, styrene-butadiene rubber, urethane rubber, nitrile rubber, acrylic rubber, fluoro-rubber, silicone rubber, etc., various thermoplastic elastomers based on urethane, polyester, polyamide, olefin, styrene or the like, and mixtures thereof.

In addition, the seal member 8 is formed with a channel 82 therein, at a location different from that of the slit 81. The channel 82 is substantially L-shaped, and opens at a distal surface and a side surface of the seal member 8.

When the seal member 8 is inserted into the outer-needle hub 3 and the opening of the channel 82, which opens on the side surface of the seal member 8, is matched with the opening of the aforementioned channel 32, which opens on the inside 31 of the outer-needle hub 3, a crank-shaped relay channel is formed (completed). The inner cavity 21 of the outer needle 2 and the inner cavity 71 of the tube 7 communicate with each other through the relay channel. This configuration makes it possible for the length of the relay channel to be comparatively small, and prevents the outer-needle hub 3 from becoming enlarged in size.

Incidentally, in the present invention, a configuration may be adopted in which the seal member 8 is not formed with the channel 82, but instead, wherein the opening of the channel 32, which opens at the inside 31 of the outer-needle hub 3, is located on the distal side relative to the seal member 8.

In addition, the indwelling needle assembly 1 is preferably subjected to a friction-reducing treatment, for thereby reducing frictional resistance between the inner surface of the slit 81 and the outer surface of the inner needle 4.

Examples of such a friction-reducing treatment include a treatment in which a lubricant is applied to at least one of the inner surface of the slit 81 and the outer surface (outer peripheral surface) of the inner needle 4, and a treatment in which a layer of a low-friction material (low-friction layer) is formed on the inner surface of the slit 81.

Such a friction-reducing treatment enables a reduction in frictional resistance between the inner needle 4 and the seal member 8, when the outer needle 2 is advanced using the inner needle 4 as a guide. Consequently, the outer needle 2 can be moved smoothly, and the indwelling needle assembly 1 is rendered excellent in operability when a puncturing operation is carried out.

Further, the indwelling needle assembly 1 includes the protector 9, which covers at least the point 41 of the inner needle 4 when the inner needle 4 is pulled out of the outer needle 2. The protector 9 will be described below.

Figure 7:
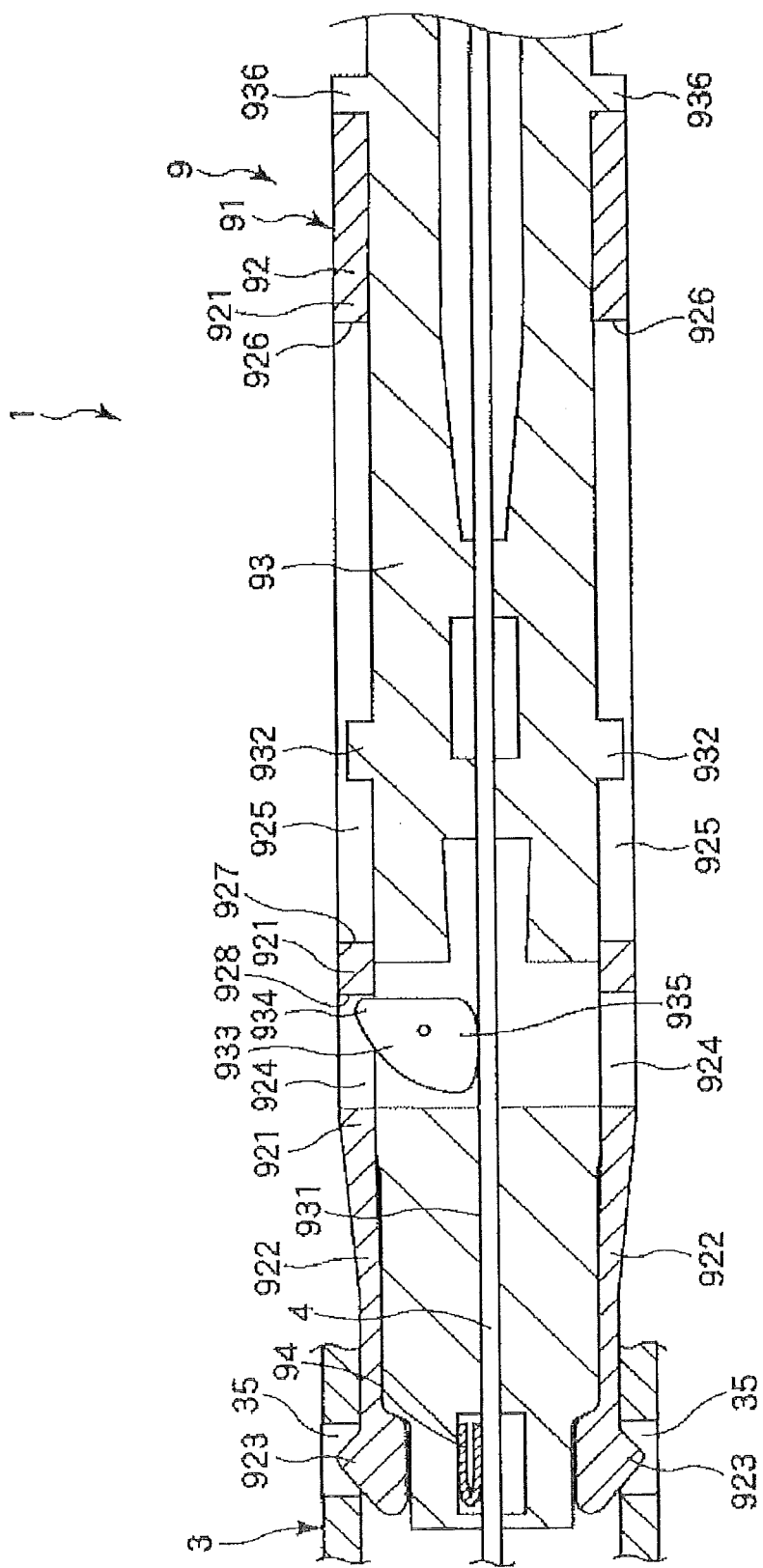
FIG. 7 is a sectional view taken along line B-B of FIG. 3.

The protector 9 is detachably connected to the outer-needle hub 3. As shown in FIGS. 3 and 7, the protector 9 includes a protector body 91, and a shutter member (shutter means) 94 provided inside the protector body 91.

The protector body 91 has a protector cover 92, and an internal member 93 inserted in the protector cover 92. The protector cover 92 and the internal member 93 are configured so that they can be moved relative to each other and can assume an unmovable state (a state in which they are inhibited from moving relative to each other) as well as a movable state.

The protector cover 92 has a tubular (hollow cylindrical) cover body section 921, and four projected sections 922, which are formed at a distal portion of the cover body section 921, and which project in the distal direction. On distal sides thereof, the projected sections 922 are inserted into a proximal portion of the outer-needle hub 3. Each of the projected sections 922 is formed at the distal portion thereof with a projection 923, which is inserted into a hole 35 formed in the proximal portion of the outer-needle hub 3, and which becomes caught on an edge portion confronting the hole 35.

When the internal member 93 is inserted in the protector cover 92 so that a distal portion of the internal member 93 is located at a portion (position) of the projections 923 of the projected sections 922 of the protector cover 92, as shown in FIGS. 3 and 7, the internal member 93 inhibits the projections 923 from moving (deforming) toward the center axis (axis) of the inner needle 4, whereby the projections 923 on the edge portions confronting on the holes 35 (a condition in which the projections 923 are caught on the edge portions confronting on the holes 35) is held (maintained). As a result, the connected condition between the protector 9 and the outer-needle hub 3 is maintained.

Figure 10:
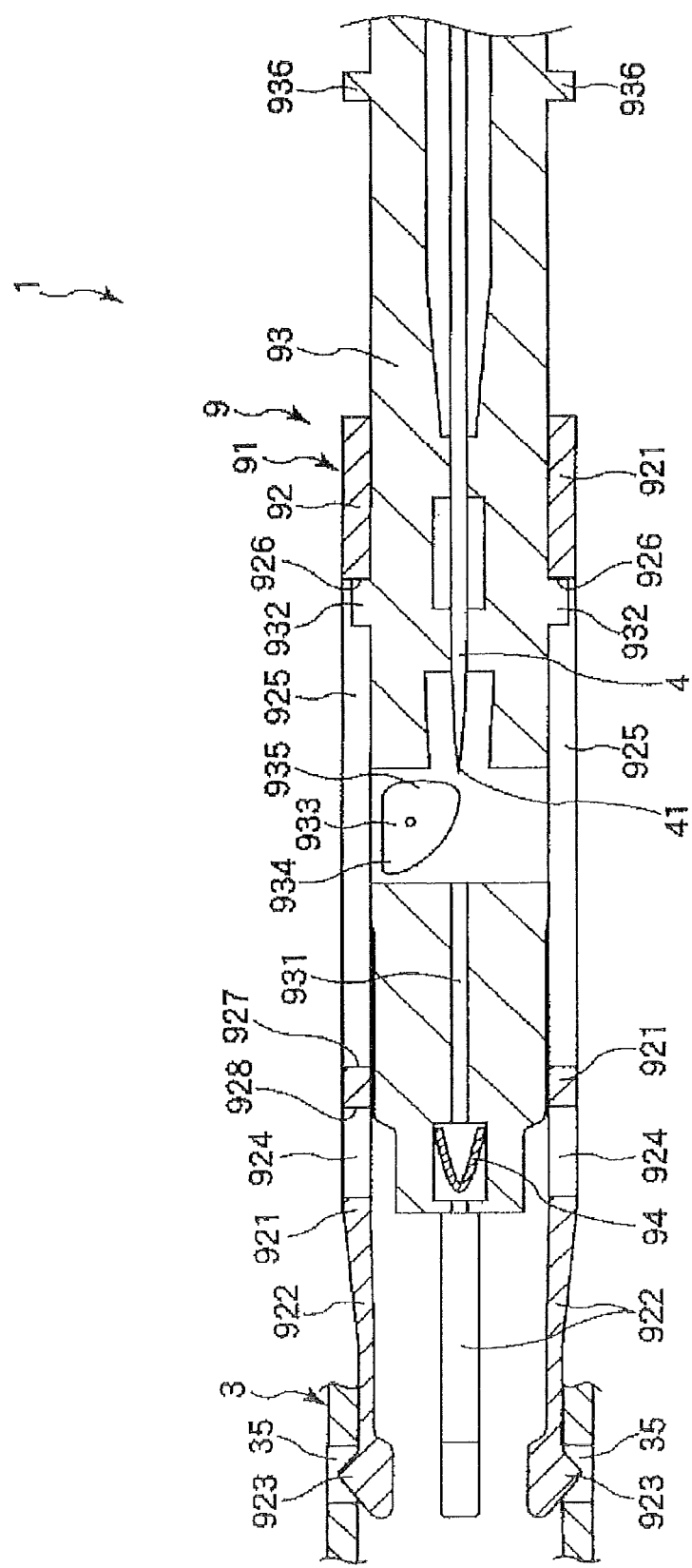
FIG. 10 is a sectional view taken along line B-B of FIG. 3.

Starting from this condition, when the internal member 93 is moved in the proximal direction relative to the protector cover 92, and a distal portion of the internal member 93 reaches the proximal side of the projections 923 of the protector cover 92, the projections 923 are able to move toward the center axis of the inner needle 4, as shown in FIG. 10. In this condition, when the protector cover 92 is moved in the proximal direction relative to the outer-needle hub 3, the projected sections 922 become deformed (deflected) toward the center axis of the inner needle 4, whereby latching of the projections 923 on the edge portions confronting on the holes 35 is released, and the protector 9 becomes disengaged from the outer-needle hub 3.

In addition, the cover body section 921 is formed on both lateral sides thereof with slots 924 and 925 formed along the longitudinal direction (the longitudinal direction of the inner needle 4). The slots 924 are formed in a distal portion of the cover body section 921. The slots 925 are formed on the proximal side relative to the slots 924, and the length of the slots 925 in the longitudinal direction is greater than the length of the slots 924 in the longitudinal direction.

The material constituting the protector cover 92 is not particularly limited. For example, the same materials as mentioned above for the outer-needle hub 3 and the inner-needle hub 5 can be used as the material for the protector cover 92.

The internal member 93 is inserted into the protector cover 92, and is tubular (hollow cylindrical) in shape. Specifically, the internal member 93 is formed in a central portion thereof with an inner-needle passage 931 through which the inner needle 4 is passed, and which pierces the internal member 93 from the proximal end to the distal end of the internal member 93. The shutter member 94 is accommodated in a distal portion of the internal member 93, at an intermediate position of the inner-needle passage 931.

The material constituting the internal member 93 is not particularly limited. For example, the same materials as those mentioned above for the outer-needle hub 3 and the inner-needle hub 5 can be used as the material for the internal member 93.

Figure 8:
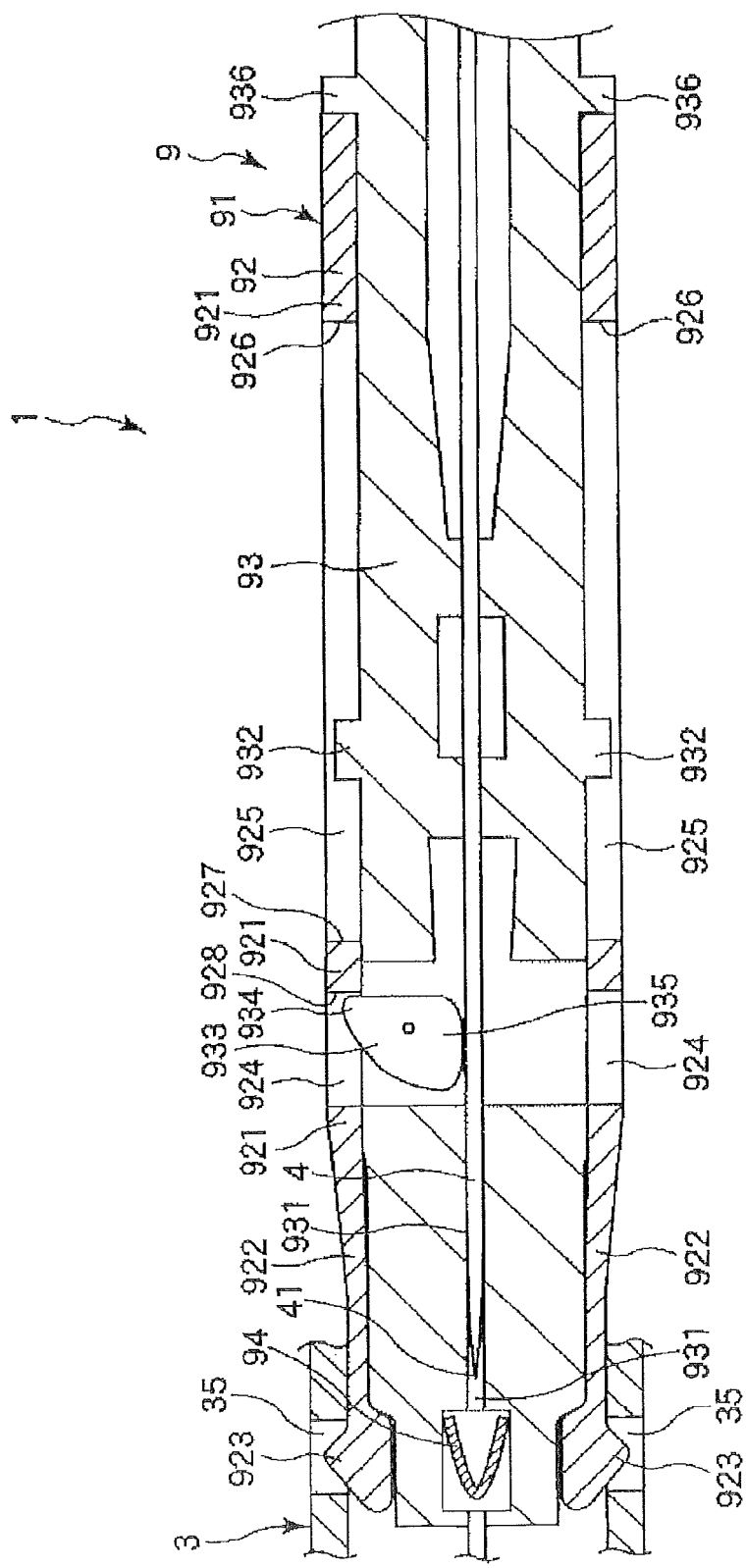
FIG. 8 is a sectional view taken along line B-B of FIG. 3.

The shutter member 94 is formed by bending an elastic (elastically deformable) belt-like plate member into a substantially V-shaped form, the opening angle of which can be varied (opened and closed), thus permitting the shutter member 94 to assume (be deformed into) a first posture, in which the inner needle 4 can be inserted in (passed through) the inner-needle passage 931 (i.e., the posture shown in FIGS. 3 and 7), and a second posture in which the passage of the point 41 of the inner needle 4 is inhibited (i.e., the posture shown in FIG. 8).

When the inner needle 4 is inserted entirely into (passed through) the inner-needle passage 931, as shown in FIGS. 3 and 7, the shutter member 94 is accommodated in a folded state, so that the opening angle is reduced, and hence the shutter member 94 is in the first posture. In this condition, the protector 9 can be moved in the longitudinal direction of the inner needle 4 (along the direction of the center axis $O_1$ of the outer needle 2) relative to the inner needle 4 and the inner-needle hub 5.

When the inner-needle hub 5 is moved in the proximal direction relative to the protector 9, starting from this condition, and as shown in FIG. 8, the point 41 of the inner needle 4 reaches the proximal side of the shutter member 94, the shutter member 94 opens under its own elastic force (restoring force) into the second posture, thereby cutting off the inner-needle passage 931. In this condition, the shutter member 94 inhibits the point 41 from moving (passing) in the distal direction beyond the shutter member 94.

The material constituting the shutter member 94 is not particularly limited, insofar as it can inhibit the passage of the point 42 therethrough. Examples of such a material include the same various resin materials as those mentioned above for the outer-needle hub 3 and the inner-needle hub 5, as well as various metallic materials such as stainless steel, aluminum alloys, copper, titanium, etc.

In addition, the thickness of the shutter member 94 is not particularly limited. For instance, the thickness is preferably about 0.03 to 0.2 mm, and more preferably, about 0.04 to 0.1 mm.

Further, a lubricant preferably is applied to a surface of the shutter member 94. This reduces frictional resistance (sliding resistance) between the outer peripheral surface of the inner needle 4 and the shutter member 94, in a condition where the shutter member 94 is in the first posture, thus enabling smoother movement of the inner needle 4 relative to the protector 9.

Incidentally, part of the shutter member 94 may be fixed to the internal member 93 by methods, for example, such as embedding, fusing, adhesion with an adhesive, etc. Further, in the present invention, the shutter member 94 is not limited to the configuration shown in the figures, and the shutter member 94 may be formed in any shape or configuration.

In addition, the internal member 93 is formed, on both lateral sides at a central portion thereof, with projected portions 932, which are inserted into corresponding slots 925 in the protector cover 92.

As a result, the internal member 93 can be prevented from rotating (turning) relative to the protector cover 92.

Further, when the internal member 93 is moved in the proximal direction relative to the protector cover 92, as shown in FIG. 10, the projected portions 932 of the internal member 93 abut on proximal-side edge portions 926 of the slots 925 in the protector cover 92. This inhibits the internal member 93 from moving in the proximal direction relative to the protector cover 92. Also, in this condition, when the internal member 93 is moved in the proximal direction relative to the protector cover 92, the internal member 93 and the protector cover 92 are moved as one body in the proximal direction. In addition, the internal member 93 can be prevented from slipping off (becoming disengaged) from the protector cover 92.

Further, a lock member 933 is rotatably disposed between the arrangement position (distal portion) of the shutter member 94, at a side section on the upper side in FIG. 7, and the projected portions 932 of the internal member 93.

When the inner needle 4 is located at the position of the lock member 933, i.e., when the inner needle 4 is inserted entirely within (passed through) the inner-needle passage 931, as shown in FIG. 7, the inner needle 4 makes contact with a bottom portion (proximal portion) 935 of the lock member 933, and the lock member 933 is held in a posture such that the tip portion 934 thereof is directed away from the inner needle 4 (directed toward the upper side in FIG. 7) (rotation of the lock member 933 is inhibited). When the lock member 933 assumes this posture, the tip portion 934 thereof can abut on (be engaged with) a proximal-side edge portion 928 of the slot 924 and a distal-side edge portion 927 of the slot 925.

Figure 9:
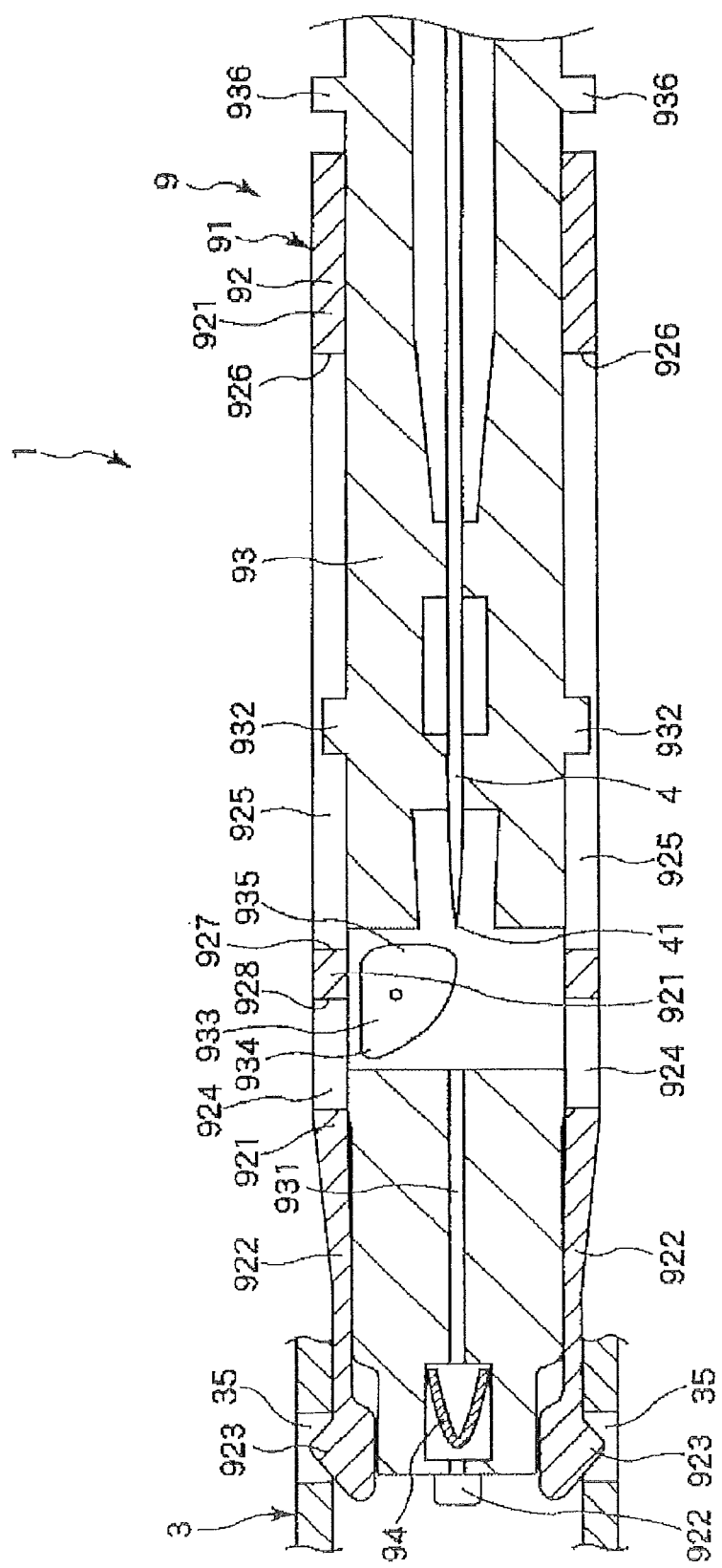
FIG. 9 is a sectional view taken along line B-B of FIG. 3.

In addition, when the inner needle 4 is located on the proximal side relative to the portion of the lock member 933 (is not located at the portion of the lock member 933), as shown in FIG. 9, rotation of the lock member 933 is allowed. Thus, the lock member 933 can assume a posture in which no part thereof makes contact with the edge portion 927 or 928.

Further, the internal member 93 is formed, on both lateral sides at a proximal portion thereof, with ribs (flanges) 936, which are capable of abutting on a proximal end surface of the cover body section 921 of the protector cover 92.

In the assembled condition, as shown in FIGS. 3 and 7, the internal member 93 is inserted into the protector cover 92, and a distal portion of the internal member 93 is located at portions of the projections 923 of the projected sections 922 of the protector cover 92. As mentioned above, this ensures that the catch of the projections 923 on the edge portions confronting on the holes 35 is maintained, and thus the connected condition between the protector 9 and the outer-needle hub 3 is held securely.

In addition, by abutment of the ribs 936 of the internal member 93 on the proximal end of the cover body section 921 of the protector cover 92, the internal member 93 is inhibited from moving in the distal direction relative to the protector cover 92.

On the other hand, the inner needle 4 is inserted entirely into the inner-needle passage 931, and the lock member 933 is held in a posture so that the tip portion 934 thereof is directed away from the inner needle 4 (directed toward the upper side in FIG. 7), as mentioned above. With the tip portion 934 of the lock member 933 located inside the slot 924 and abutting on the proximal-side edge portion 928 of the slot 924, the internal member 93 is inhibited from moving in the proximal direction relative to the protector cover 92.

This ensures that the internal member 93 and the protector cover 92 are moved together as one body, whereby the protector 9 and the outer-needle hub 3 are moved integrally.

According to the protector 9 described above, after use, the point 41 of the inner needle 4 can be covered speedily and safely through a simple operation. In addition, by action of the shutter member 94, once the point 41 is covered, it is prevented from protruding from the distal end of the protector body 91 (the internal member 93) of the protector 9. Therefore, when the inner needle 4 is disposed of, or in similar situations, an accident in which the operator or the like mistakenly punctures his or her hand or finger with the point 41 is prevented from occurring, and thus high safety is secured.

In addition, as shown in FIG. 12, the indwelling needle assembly 1 has the link member 20, which functions as an anti-slipping means, for preventing the protector 9 from slipping off from the point 41 of the inner needle 4 when the protector 9 covers the point 41, and also functions as a linking means for linking the protector 9 and the inner-needle hub 5 to each other.

The link member 20 is configured to link the internal member 93 of the protector 9 and the inner-needle hub 5 to each other. This ensures that when the inner-needle hub 5 is moved in the proximal direction, the internal member 93 (the protector 9) is pulled (moved) in the proximal direction through the link member 20.

Moreover, the link member 20 is bellows-like in form, and can therefore be extended and contracted. The link member 20 has a length such that when the link member 20 is extended maximally (is fully extended), the point 41 of the inner needle 4 is located on the proximal side relative to the lock member 933, yet at the same time, the point 41 is accommodated inside the internal member 93 (i.e., will not slip off from the internal member 93).

Thus, the link member 20 links the internal member 93 and the inner-needle hub 5 to each other, and has a length such that the point 41 is accommodated in the internal member 93 in a condition where the link member 20 is extended maximally. This ensures that the protector 9 is securely prevented from slipping off from the inner-needle hub 5 or the point 41. Also, the condition whereby the point 41 is covered by the protector 9 can be maintained assuredly. Consequently, when the inner needle 4 is disposed of, or in similar situations, an accident in which the operator or the like mistakenly punctures his or her hand or finger with the point 41 is prevented from occurring, and high safety is secured.

In addition, the link member 20 is contracted, or folded, in the assembled condition, whereas the link member 20 is extended, or spread, in the condition where the inner needle 4 is pulled out of the outer needle 2 and the point 41 is covered by the protector 9.

The aforementioned link member 20 is contracted in the assembled condition, and in the contracted state, the link member 20 is accommodated in the inner-needle hub 5. This ensures that the link member 20 will not present an obstacle when a puncturing operation is performed, so that operability of the indwelling needle assembly 1 is enhanced. Further, the indwelling needle assembly 1 can be reduced in size.

In addition, in the condition where the link member 20 is contracted, as well as in the condition where the link member 20 is extended, the inner needle 4 penetrates the link member 20. This ensures that the inner needle 4 functions as a guide for the link member 20 when the link member 20 is extended and contracted. Therefore, for example, when the indwelling needle assembly 1 is placed in an assembled condition (i.e., is manufactured), it is possible to securely prevent the link member 20 from becoming contracted in an unintended state. More specifically, the link member 20 is prevented from becoming contracted without being accommodated in the inner-needle hub 5.

Further, the link member 20 has a self-restoring property (restoring property) for returning to its natural state. More specifically, in a state when the link member 20 is contracted and is shorter than its natural state, the link member 20 functions as a biasing means and is biased in the extending direction by the restoring force thereof. On the other hand, when in an extended state longer than its natural state, the link member 20 functions as a biasing means and is biased in the contracting direction by its restoring force. The term "natural state" implies a state in which no external force is exerted on the link member 20.

Meanwhile, in the indwelling needle assembly 1, as shown in FIGS. 3 to 5, the finger hold (tab) 6, which is pressed by a finger so as to move the outer needle 2 in the distal direction relative to the inner needle 4, is formed (provided) so as to project on the protector cover 92 of the protector 9. The protector cover 92 and the finger hold 6 are formed as a unitary body. In addition, the finger hold 6 projects in an upward direction.

Incidentally, a structure may be adopted in which the protector cover 92 and the finger hold 6 are formed as separate members, which are joined respectively to each other. In this case, the material constituting the finger hold 6 is not particularly limited. For example, the same materials as those mentioned above as materials for the outer-needle hub 22 and the inner-needle hub 32 can be used for the finger hold 6. Further, the finger hold 6 may project in a direction other than the illustrated direction (for instance, sideways).

Herein, during use of the indwelling needle assembly 1, the term "upward direction" refers to the direction in which the skin (body skin), in the vicinity of the part of the patient (the person on whom the assembly is used) to be punctured by the outer needle 2 (the inner needle 4), is oriented. Namely, the "upward direction" refers to the direction from the skin side toward the side of the indwelling needle assembly 1. In other words, the "upward direction" is the direction in which a cutting edge surface (not shown) formed at the point 41 of the inner needle 4 is oriented.

The finger hold 6 is provided on the proximal side thereof with a finger hold surface 64, on which to place the finger. The finger hold 6 has a shape such that, when the outer needle 2 is moved in the distal direction relative to the inner needle 4, a force in an upward direction (vertically upward direction) relative to the center axis (axis) $O_1$ of the outer needle 2, i.e., a force in the direction in which the finger hold 6 projects (projecting direction) (the upward direction in FIG. 4), is capable of acting on the finger hold 6.

This ensures that when the outer needle 2 is moved in the distal direction relative to the inner needle 4 during a puncturing operation, the finger hold 6 can be pressed by the finger in the distal direction, while lifting up (in the manner of lifting up) the finger hold 6 in the projecting direction thereof (the upward direction in FIG. 4). This, in turn, ensures that the outer needle 2 can be moved straightly along its center axis $O_1$, namely, along the direction of the center axis $O_1$, without becoming bent. Consequently, the outer needle 2 can be moved (advanced) smoothly, and excellent operability is secured.

In the present embodiment, the finger hold 6 is formed at a distal portion of the cover body section 921 of the protector cover 92, wherein the finger hold 6 has a shape obtained by bending a plate member, as shown in FIG. 4. Specifically, the finger hold 6 is composed of an inclined portion (inclined plate) 61, which is disposed on the distal side relative to the cover body section 921 and is inclined toward the proximal side, a base portion 63 fixed to a distal portion of the cover body section 921, and a connecting portion (connecting plate) 62 connecting the inclined portion 61 and the base portion 63 to each other. A proximal-side surface of the inclined portion 61 constitutes the finger hold surface 64. In the case of such a finger hold 6, the finger is inserted into a space between the finger hold surface 64 (the inclined portion 61) and the connecting portion 62, whereby the finger becomes caught on the finger hold surface 64, and in this condition, the finger hold 6 can be pressed by the finger in the distal direction, while being lifted up in the projecting direction thereof.

In addition, the positional relationship between the finger hold 6 and the center axis $O_1$ of the outer needle 2 is not particularly limited. Preferably, however, the finger hold 6 is located on the center axis $O_1$ of the outer needle 2 in plan view (as viewed from the upper side in FIG. 4), as shown in FIG. 1. This enables the outer needle 2 to be moved along the direction of the center axis $O_1$ more smoothly and assuredly.

Further, the positional relationship between the base portion 63 as a fixed point (fixed part) of the finger hold 6 and the finger hold surface 64 is not particularly limited. Preferably, however, the base portion 63 is located on the proximal side relative to a tip 641 of the finger hold surface 64. In the illustrated configuration, the base portion 63 is located on the proximal side relative to a base end 642 of the finger hold surface 64. However, configurations other than the illustrated configuration shown may be provided, in which the base portion 63 preferably is located, for example, between the tip 641 and the base end 642 of the finger hold surface 64.

In addition, the finger hold surface 64 of the finger hold 6 is formed with a rugged pattern (for example, a plurality of ribs arrayed in an up-down direction on the finger hold surface 64), which functions as an anti-slipping means for the finger. This ensures that when the finger hold 6 is pressed by the finger so as to move the outer needle 2 in the distal direction, the finger can be prevented from slipping out of position.

Further, the finger hold 6 has a reinforcement section for suppressing bending of the finger hold 6 when the finger hold 6 is pressed by the finger. The reinforcement section is composed of a rib 611, which is formed at the inclined portion 61 on an opposite side from the finger hold surface 64, and a rib 631 formed at the base portion 63.

In addition, the dimensions of the finger hold 6 are not particularly limited. Preferably, however, the width (w) of the finger hold surface 64 of the finger hold 6 is about 2 to 50 mm, and more preferably, about 2 to 30 mm.

If the width (w) is less than the lower limit, the finger may slip off from the finger hold surface 64, thus making the puncturing operation difficult to carry out. On the other hand, if the width (w) is more than the upper limit, the finger hold 6 may present an obstacle.

Further, the height (h) of the finger hold 6 from the outer surface of the protector cover 92 (the protector 9) is preferably about 1 to 50 mm, and more preferably, about 2 to 20 mm.

If the height (h) is less than the lower limit, it may become impossible to locate a finger on the lower side of the finger hold surface 64 and allow the finger to be caught on the finger hold surface 64. If the height (h) is more than the upper limit, on the other hand, the finger hold 6 may become an obstacle.

Herein, preferably, the finger hold 6 satisfies the following condition (1) or (2).

(Condition 1)

The finger hold surface 64 of the finger hold 6, in a condition where the rugged pattern (anti-slipping means) is omitted, or in a condition before the rugged pattern is provided, has a portion to which the normal 11 extending toward the proximal side is directed, toward the side of the center axis $O_1$ of the outer needle 2. Incidentally, in the illustrated configuration, over substantially the entirety of the finger hold surface 64, the normal 11 that extends toward the proximal side is directed toward the side of the center axis $O_1$ of the outer needle 2.

This ensures that, when the outer needle 2 is moved in the distal direction relative to the inner needle 4 during a puncturing operation, the finger hold 6 can more easily and assuredly be pressed by a finger in the distal direction, while being lifted up in the projecting direction thereof, whereby enhanced operability is secured.

(Condition 2)

The finger hold surface 64 of the finger hold 6, in the condition where the rugged pattern (anti-slipping means) is omitted, or in the condition prior to providing the rugged pattern, has a surface (portion) thereof, in which an angle θ with respect to the center axis $O_1$ of the outer needle 2 is less than 90° (inclusive of 0°). When the finger hold surface 64 is a plane (planar surface), the aforementioned surface forms the plane. When the finger hold surface 64 is a curved surface, the aforementioned surface is a plane (a tangent line in side view) which is tangential to the curved surface. Incidentally, in the illustrated configuration, over the entirety of the finger hold surface 64, the angle θ with respect to the center axis $O_1$ of the outer needle 2 is less than 90°.

This ensures that when the outer needle 2 is moved in the distal direction relative to the inner needle 4 during a puncturing operation, the finger hold 6 can more easily and assuredly be pressed by the finger in the distal direction, while being lifted up in the projecting direction thereof, whereby enhanced operability is secured.

In addition, the angle θ to the center axis $O_1$ of the outer needle 2 preferably is not more than 85°, more preferably is about 30° to 80°, and even more preferably, is about 45° to 75°.

Further, the shape of the finger hold 6 is not limited to the shape shown in the figures. Specifically, it is sufficient if the finger hold 6 has a shape such that, when the outer needle 2 is moved in the distal direction relative to the inner needle 4, a force in the projecting direction (upward direction) relative to the center axis $O_1$ of the outer needle 2 can act on the finger hold 6. Other configuration examples, apart from the aforementioned example, include the configurations shown in (a) to (h) of FIG. 6.

Each of the finger holds 6, shown respectively in (a) to (h) of FIG. 6, satisfies the aforementioned conditions (1) and (2).

An example of the method of using the indwelling needle assembly 1 (in the case of puncturing a blood vessel) (an operation of the assembly) will be described in detail below.

[1] The indwelling needle assembly 1 is placed in an assembled condition (see FIGS. 1, 3 and 7), and the connector 72 is preliminarily connected with another connector, which is mounted on an end portion of an infusion line, thereby enabling an infusion to be supplied from the infusion line.

Incidentally, in this instance, a predetermined part of the tube 7 or the infusion line is preliminarily pinched, for example, by a clamp (an example of a channel-opening/closing means) in order to close the inner cavity.

[2] Next, the closure of the tube 7 or the infusion line by the clamp or the like is released, whereby an infusion from the infusion line is introduced through the tube 7 into the outer-needle hub 3.

The infusion, which is introduced into the outer-needle hub 3, fills the channel 32, the channel 82, and a space on the distal side relative to the seal member 8, of the inner cavity 31 of the outer-needle hub 3, and is introduced into the inner cavity 21 of the outer needle 2, thereby priming the inner cavity 21 of the outer needle 2 with the infusion. In this instance, a portion of the infusion flows out via the distal opening 22 of the outer needle 2.

[3] After priming is completed, the tube 7 or the infusion line is again preliminarily closed by a clamp or the like, and the wings 12a and 12b are closed by pinching them with the fingers. Using the wings 12a and 12b as a grip portion (operating portion), a blood vessel (a vein or an artery) of a patient is punctured with the outer needle 2 and the inner needle 4 united together.

When a puncturing operation on the blood vessel is conducted by gripping the wings 12a and 12b in this manner, the puncturing angle is reduced. Namely, the outer needle 2 and the inner needle 4 are set closely in parallel in relation to the blood vessel, as compared to conducting the puncturing operation by directly gripping the outer-needle hub 3. Consequently, the puncturing operation is facilitated, and the burden on the patient's blood vessel is lessened.

When the blood vessel is securely punctured with the outer needle 2, internal pressure in the blood vessel (blood pressure) causes blood to flow back in the proximal direction through the groove 44 in the inner needle 4, and through the inner cavity 21 of the outer needle 2. Therefore, backflow of the blood can be confirmed at least at one of the outer needle 2, the outer-needle hub 3, the inner-needle hub 5, and the tube 7, the inside of which is visible.

After backflow of the blood has been confirmed, the outer needle 2 is advanced a tiny distance in the distal direction along the inner needle 4, with the inner needle 4 acting as a guide.

In this instance, the finger hold 6 is pressed by the index finger in a distal direction, while lifting up (in the manner of lifting up) the finger hold 6 in the projecting direction thereof (in the upward direction in FIG. 3), whereby the outer needle 2 is moved in the distal direction. This enables the outer needle 2 to be moved straightly along the center axis $O_1$, or to be moved along the direction of the center axis $O_1$, without becoming bent. Consequently, the outer needle 2 can be advanced smoothly.

Further, when the blood vessel is punctured, erroneous penetration of a bubble or bubbles into the blood is securely prevented, since the inner cavity 21 of the outer needle 2 has been primed with the infusion. Thus, extremely high safety is ensured.

In addition, in the assembled condition in which the tube 7 is connected to a proximal portion of the outer-needle hub 3, the center axis $O_1$ of the outer needle 2 and the center axis $O_2$ at a distal portion of the tube 7 are substantially parallel to each other. Therefore, during puncturing of the blood vessel with the outer needle 2 and the inner needle 4, the tube 7 will not obstruct operations and excellent operability is ensured.

[4] After the blood vessel has been securely punctured by the outer needle 2 (after the outer needle 2 is moved to a desired position), the outer needle 2 or the outer-needle hub 3 is fixed with one hand, while the inner-needle hub 5 is gripped with the other hand and pulled in the proximal direction. This ensures that all of the operations, ranging from an operation of pulling the inner needle 4 out of the outer needle 2 to disengagement of the protector 9 from the outer-needle hub 3, are sequentially carried out in a continuous manner. More specifically, the inner needle 4 is first moved in the proximal direction, and then is pulled out of the outer needle 2.

[5] After the inner needle 4 has been moved further in the proximal direction and the point 41 passes through the slit 8, the seal member 8, which exhibits a self-closing property, closes the slit 81 under its own elastic force.

As a result, leakage of liquid through the slit 81 is prevented, and sterility in the outer-needle hub 3 and the infusion line is secured.

[6] After the inner needle 4 has been moved further in the proximal direction and the point 41 reaches the proximal side of the shutter member 94, as shown in FIG. 8, the shutter member 94 opens under its own elastic force, so as to attain the second posture, which cuts off the inner-needle passage 931. When the shutter member 94 has come into the second posture, any attempt to move the point 41 of the inner needle 4 back in the distal direction simply results in the point 41 coming into abutment on the shutter member 94, and hence the inner needle 4 cannot return in the distal direction.

[7] After the inner needle 4 has been moved further in the proximal direction and the inner needle 4 reaches the proximal side of the lock member 933, as shown in FIG. 9, rotation of the lock member 933 is allowed, and the internal member 93 of the protector 9 can be moved in the proximal direction relative to the protector cover 92.

On the other hand, when the inner-needle hub 5 is pulled in the proximal direction, the internal member 93 is pulled and moved in the proximal direction through the link member 20. After the distal portion of the internal member 93 reaches the proximal side of the projections 923 of the protector cover 92, as shown in FIG. 10, the projections 923 are made capable of moving toward the center axis of the inner needle 4. Consequently, it becomes possible for the protector 9 to be moved in the proximal direction relative to the outer-needle hub 3.

[8] After the internal member 93 has been moved further in the proximal direction, and the projected portions 932 of the internal member 93 abut on the proximal-side edge portions 926 of the slots 925 in the protector cover 92, as shown in FIG. 10, the internal member 93 and the protector cover 92 are moved as a unitary body in the proximal direction, whereupon the protector 9 becomes separated (disengaged) from the outer-needle hub 3.

Figure 11:
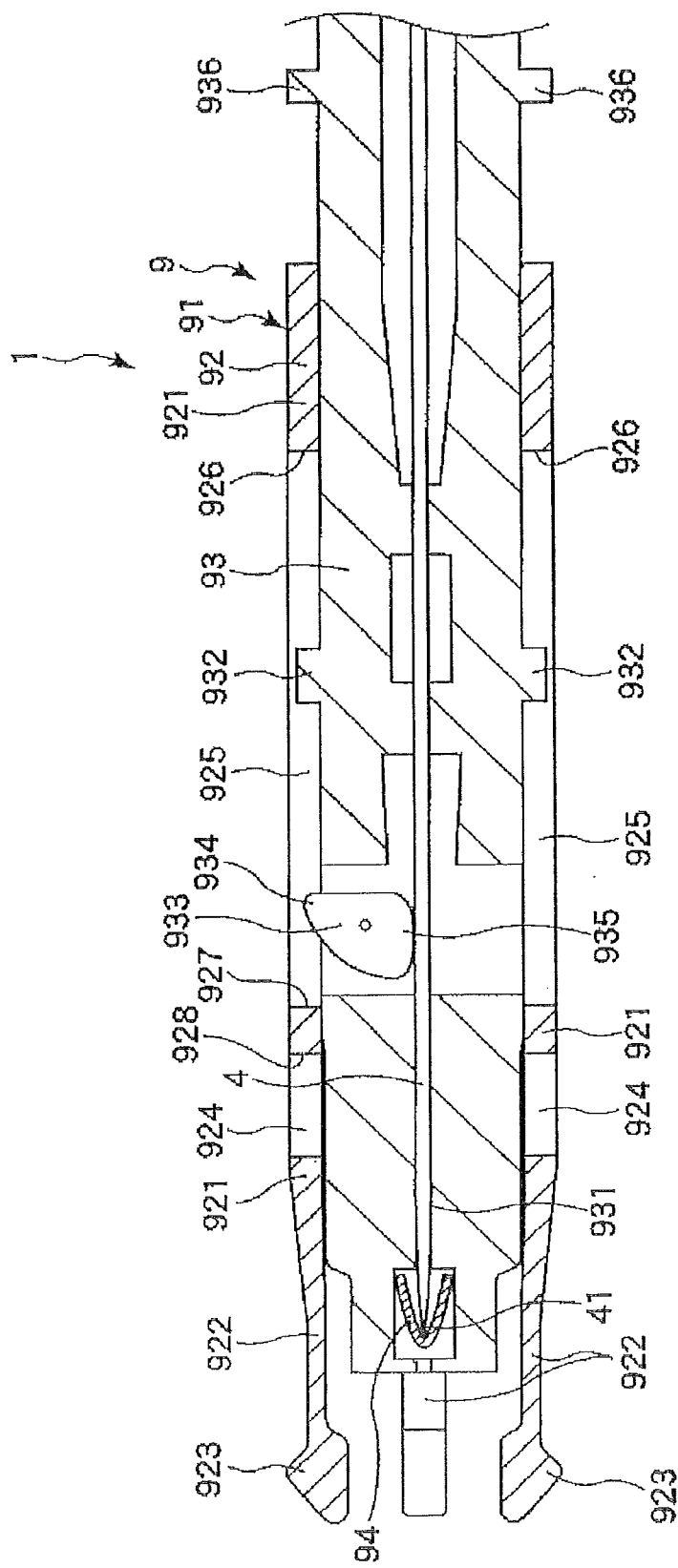
FIG. 11 is a sectional view taken along line B-B of FIG. 3.
Figure 12:
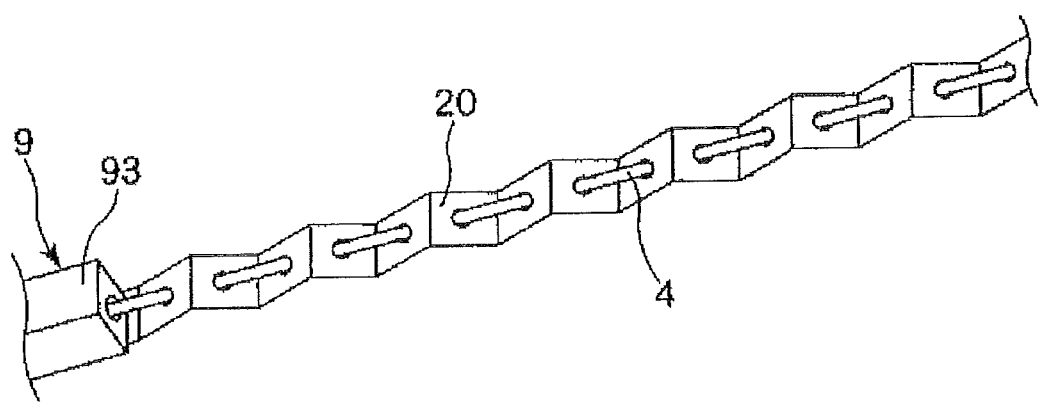
FIG. 12 is a perspective view of a link member of the indwelling needle assembly shown in FIG. 1.

[9] In addition, due to the restoring force of the link member 20, the internal member 93 is pulled and moved in the proximal direction relative to the inner needle 4, and the point 41 presses the bottom portion 935 of the lock, member 933, as shown in FIG. 11, whereby the lock member 933 is placed in a posture in which the tip portion 934 thereof is directed away from the inner needle 4 (directed toward the upper side in FIG. 11). In addition, the inner needle 4 makes contact with the bottom portion 935 of the lock member 933, thereby maintaining this posture.

[10] By the restoring force of the link member 20, the internal member 93 is further moved in the proximal direction relative to the inner needle 4, resulting in the point 41 of the inner needle 4 coming into contact with the shutter member 94, as shown in FIG. 11.

Further, in the condition where the point 41 is in contact with the shutter member 94, the internal member 93 is biased in the proximal direction by the restoring force of the link member 20, whereby this condition can be maintained.

In addition, the link member 20 has a given length so that the point 41 is accommodated in the internal member 93, in a condition where the link member 20 is maximally extended. Therefore, the protector 9 can securely be prevented from slipping off the point 41. Accordingly, the condition in which the point 41 is covered by the protector 9 can be held assuredly.

[11] Next, the tube 7, which is inserted in the tube accommodating section 52 of the inner-needle hub 5, is removed through the groove 521.

After the inner needle 4 has been pulled out from the outer needle 2 in this manner, the inner needle 4 and the inner-needle hub 5 are rendered useless and therefore are discarded.

The point 41 of the inner needle 4 is covered with the protector 9. In particular, the point 41 is prevented from moving toward the distal side beyond the shutter member 94 and to protrude from the distal end of the protector 9. Accordingly, an accident in which the person in charge of disposing of the inner needle 4 mistakenly punctures his or her hand or finger with the point 41, can be prevented from occurring.

[12] Subsequently, the wings 12*a* and 12*b* are opened and are fixed to a skin by a pressure sensitive adhesive tape or the like. In addition, closure of the tube 7 or the infusion line by the clamp is released, whereby supply of the infusion is started.

The infusion supplied from the infusion line is injected into the patient's blood vessel through the inner cavities of the connector 72, the tube 7, the outer-needle hub 3, and the outer needle 2.

As has been described above, according to the present indwelling needle assembly 1, when the outer needle 2 is moved in the distal direction relative to the inner needle 4 during a puncturing operation, the finger hold 6 can be pressed by a finger in the distal direction, while lifting up (in the manner of lifting up) the finger hold 6 in a projecting direction thereof. This enables the outer needle 2 to be moved straightly along its center axis O$_1$, or to be moved along the direction of the center axis O$_1$, without becoming bent. This, in turn, enables the outer needle 2 to be moved (advanced) smoothly. Consequently, excellent operability is ensured, whereby an infusion line or the like can be secured easily and reliably.

Incidentally, although the finger hold is provided on the protector 9 in the present embodiment, the invention is not limited to this configuration. Alternatively, the finger hold may be formed (provided) so as to project on another part (member), for example, on the outer-needle hub, as in the second embodiment, which shall be described below (see FIG. 13).

<Second Embodiment>

Figure 13:
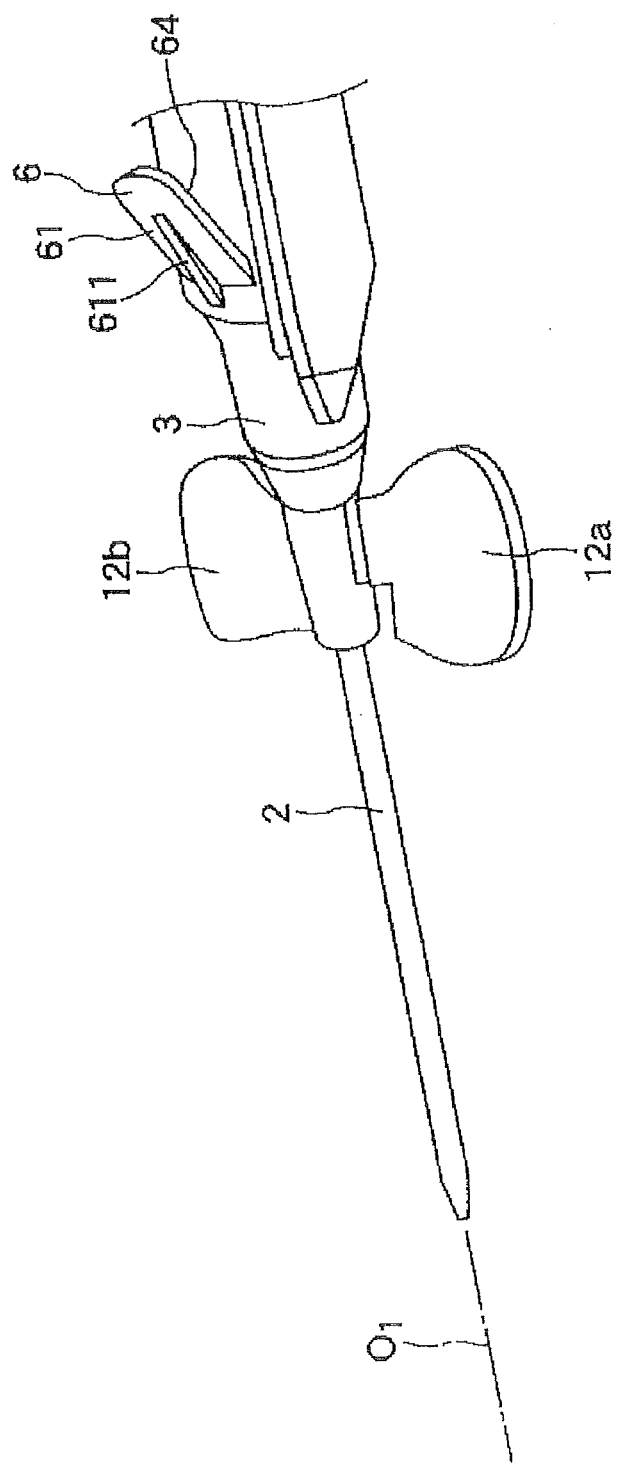
FIG. 13 shows an outer needle and an outer-needle hub, in a second embodiment of the indwelling needle assembly according to the present invention.

FIG. 13 is a perspective view showing an outer needle and an outer-needle hub, in a second embodiment of the indwelling needle assembly according to the present invention.

The indwelling needle assembly 1 in the second embodiment will be described below, the description being centered on differences from the above-described first embodiment. As for the same items as those in the first embodiment, descriptions thereof shall be omitted.

As shown in FIG. 13, in the indwelling needle assembly 1 according to the second embodiment, the protector is omitted, and a finger hold 6 is formed (provided) so as to project on an outer-needle hub 3.

Incidentally, the shape of the finger hold 6 is not limited to the shape shown. The finger hold 6, for example, may have the shapes shown in FIGS. 4 and 6 and described in the first embodiment.

According to the indwelling needle assembly 1, the same effects as those of the indwelling needle assembly 1 according to the first embodiment above can be obtained.

<Third Embodiment>

In the indwelling needle assembly according to the present invention, either one or both of the protector and the outer-needle hub are formed with the supported section, which is supported by the support section of the inner-needle hub. In the present embodiment, a case where the protector is formed with the supported section (i.e., the support section of the inner-needle hub supports the protector) will be described representatively.

Figure 14:
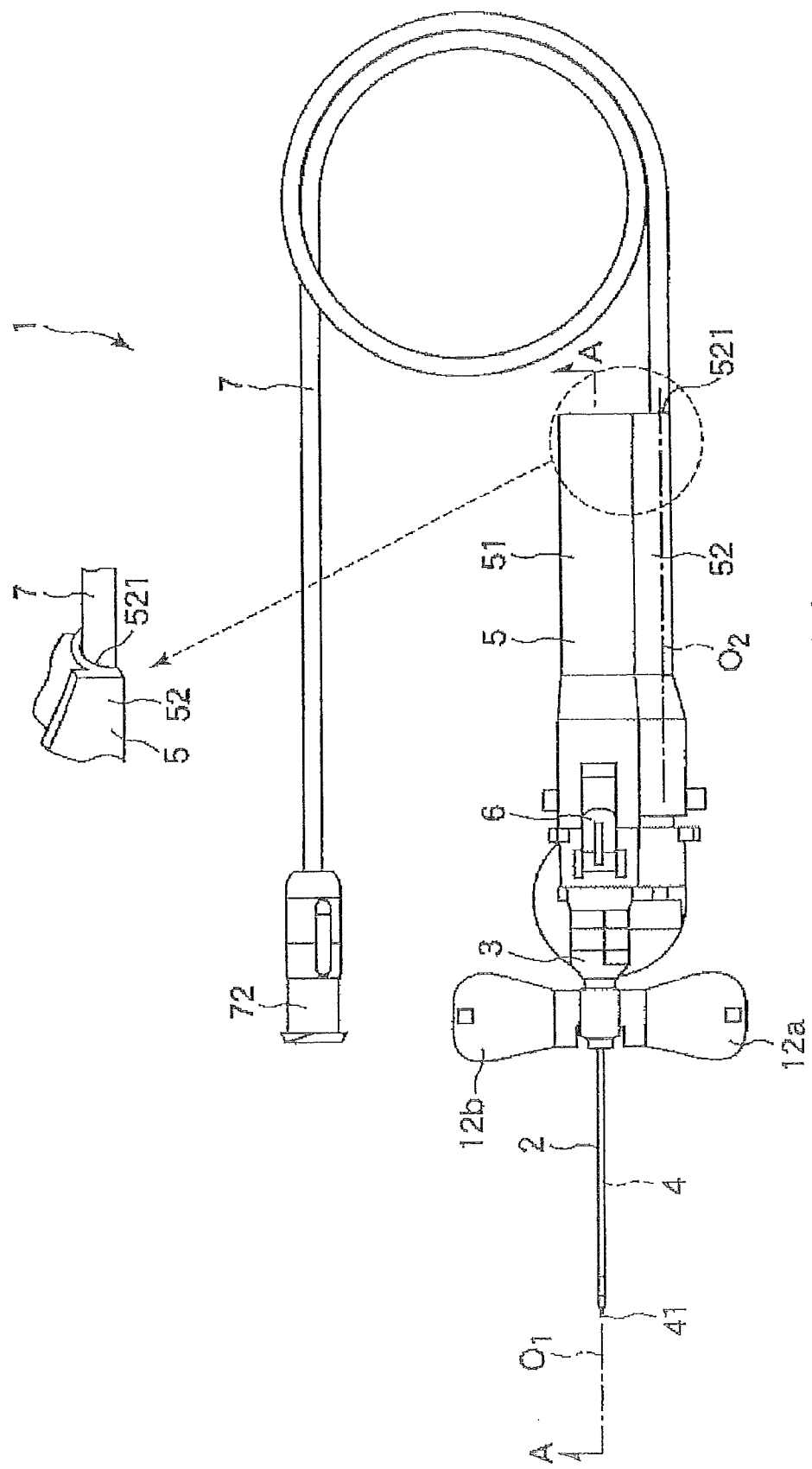
FIG. 14 is a perspective view showing a third embodiment of the indwelling needle assembly according to the present invention.
Figure 15:
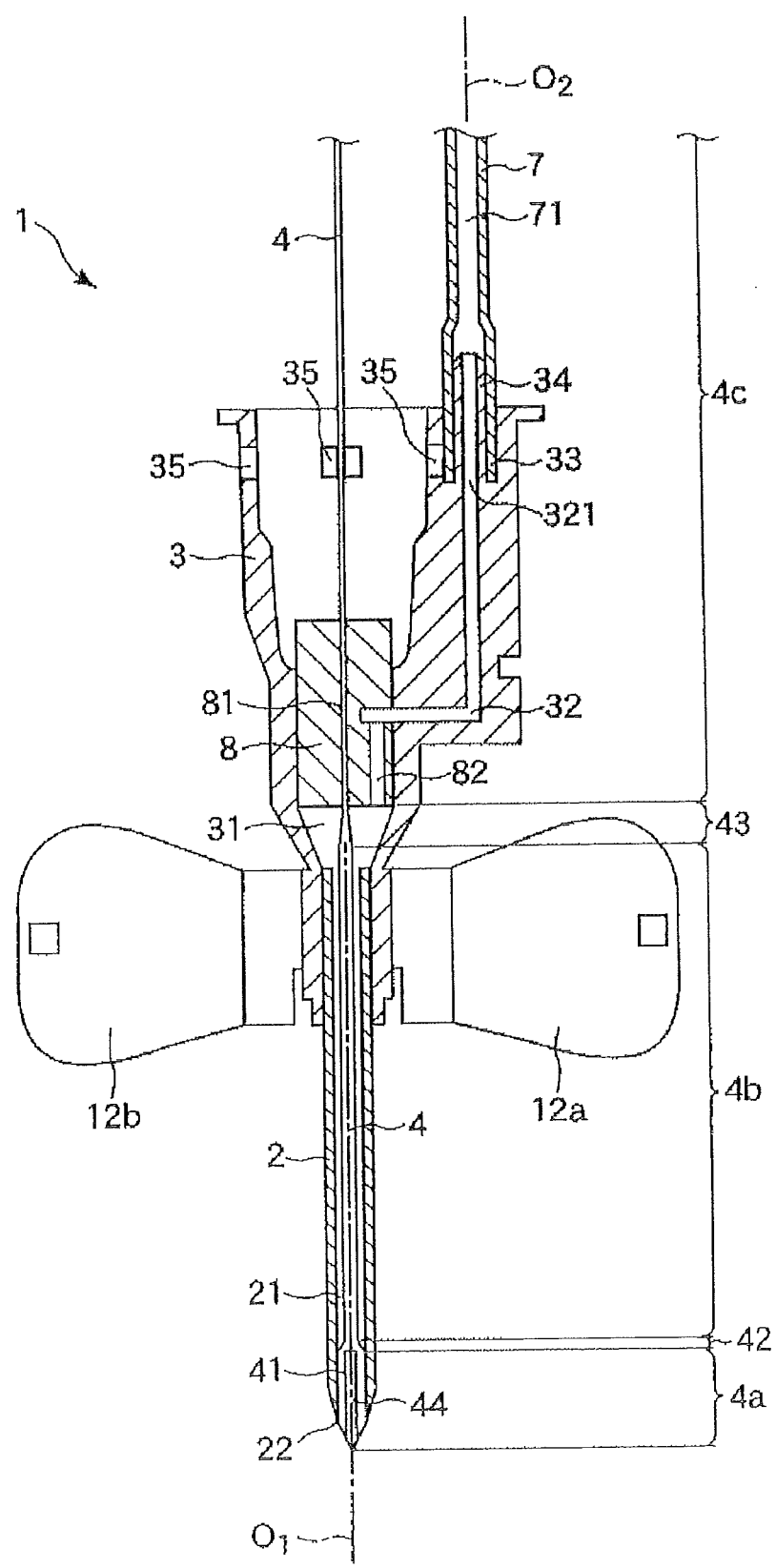
FIG. 15 is a sectional view showing an outer needle, an outer-needle hub, an inner needle, and a tube in the indwelling needle assembly shown in FIG. 14.
Figure 16:
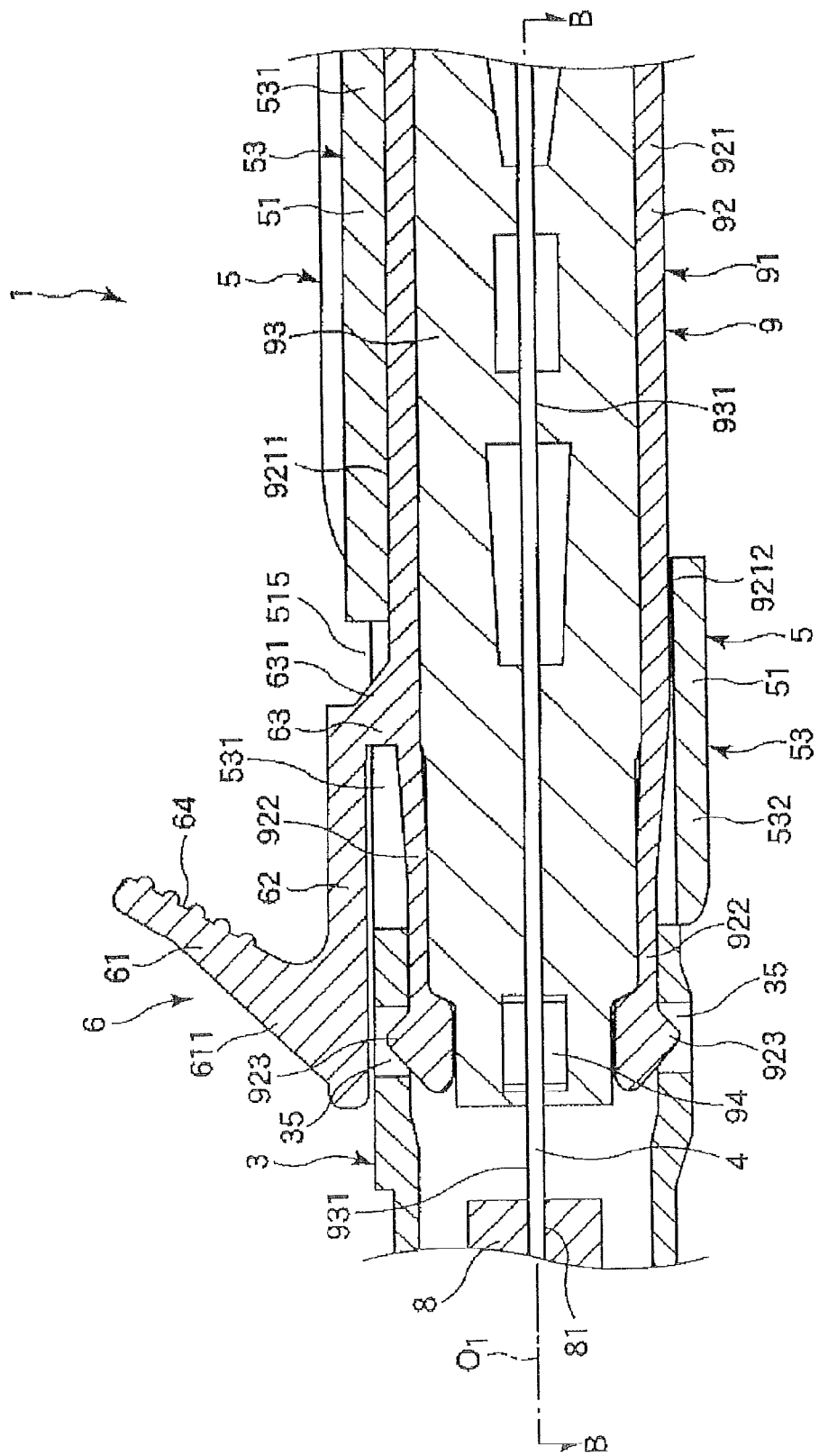
FIG. 16 is a sectional view taken along line A-A of FIG. 14.
Figure 17:
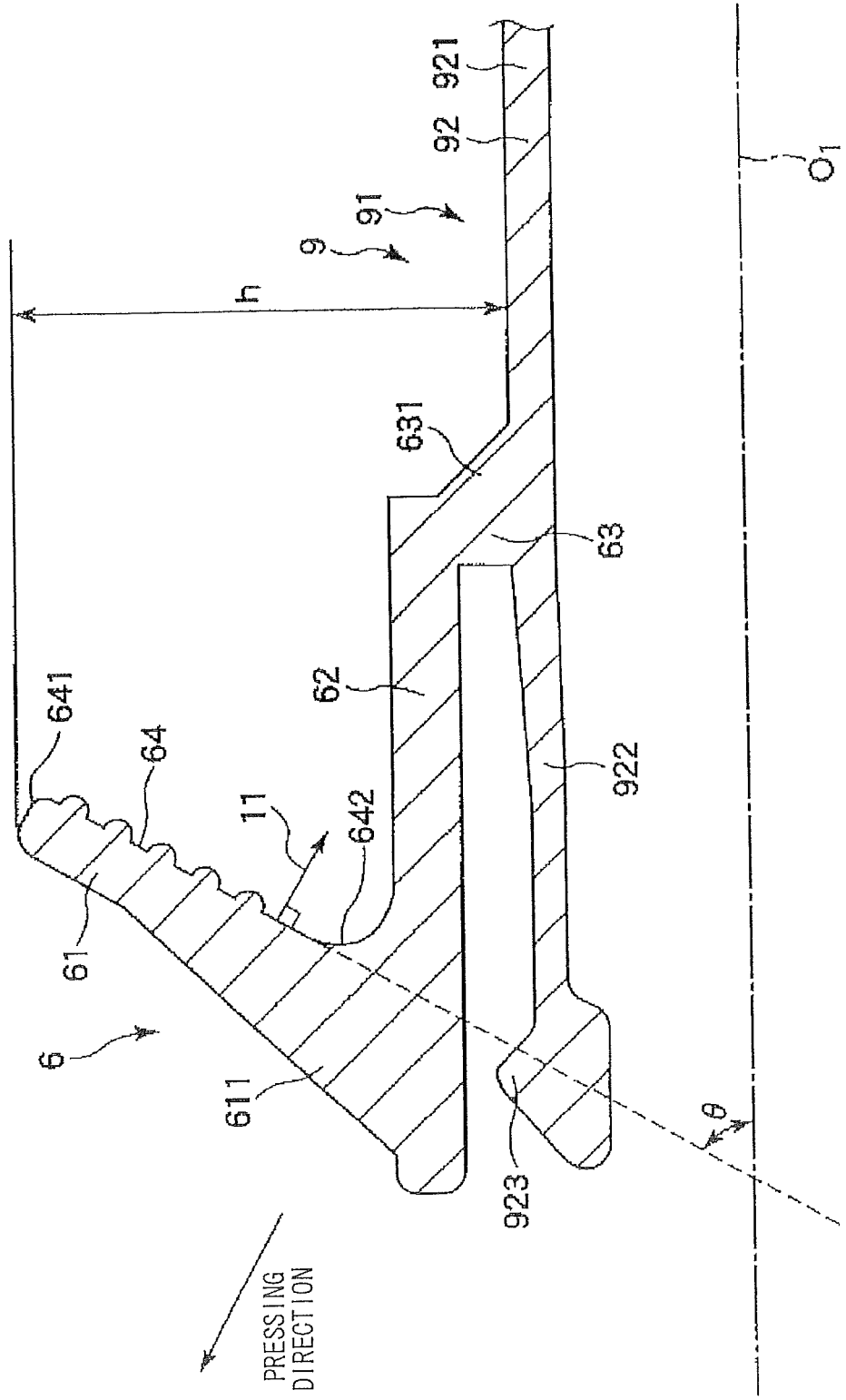
FIG. 17 is a sectional view (i.e., a sectional view taken along line A-A) of a finger hold of the indwelling needle assembly shown in FIG. 14.
Figure 18:
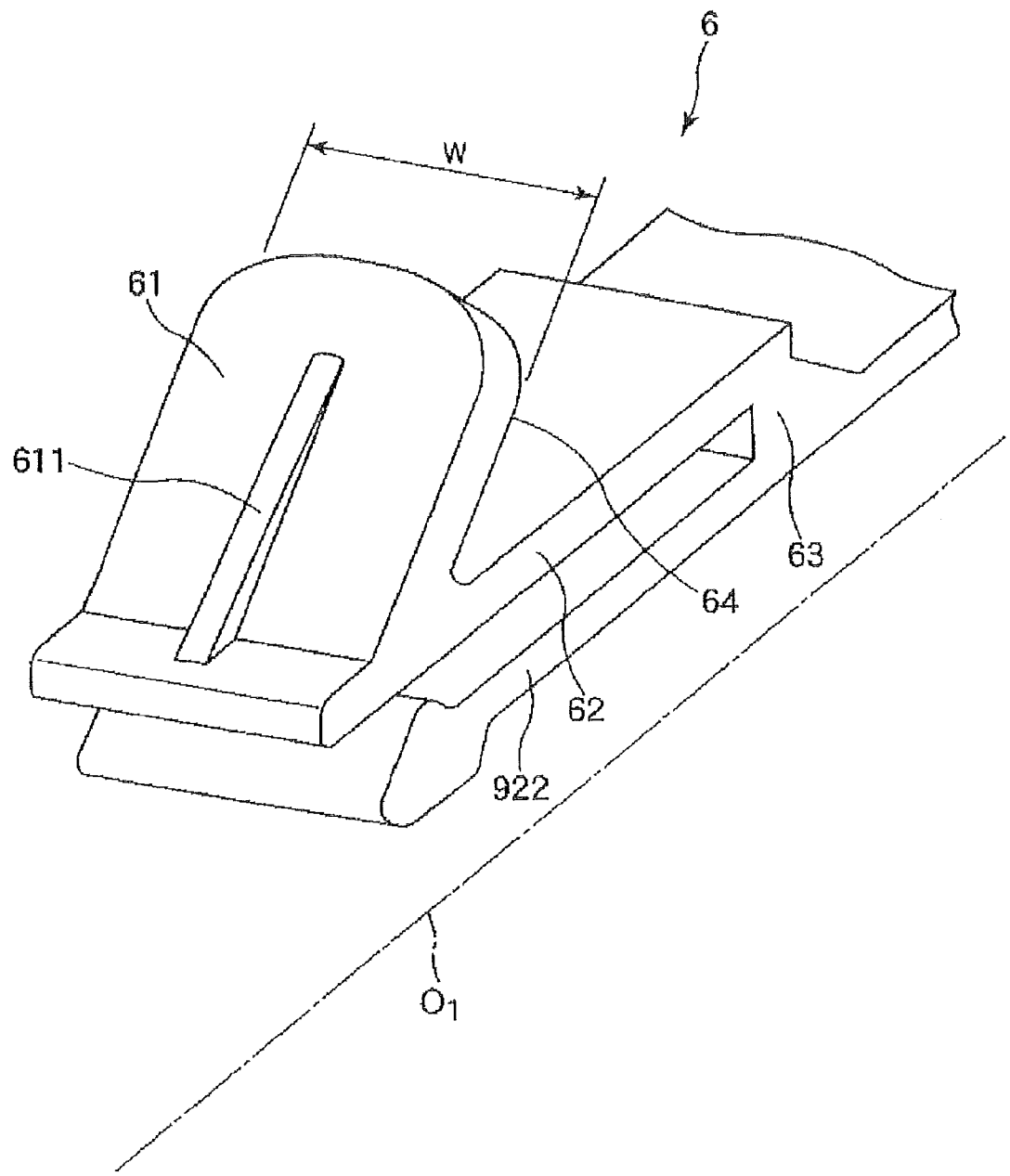
FIG. 18 is a perspective view of the finger hold of the indwelling needle assembly shown in FIG. 14.
Figure 19:
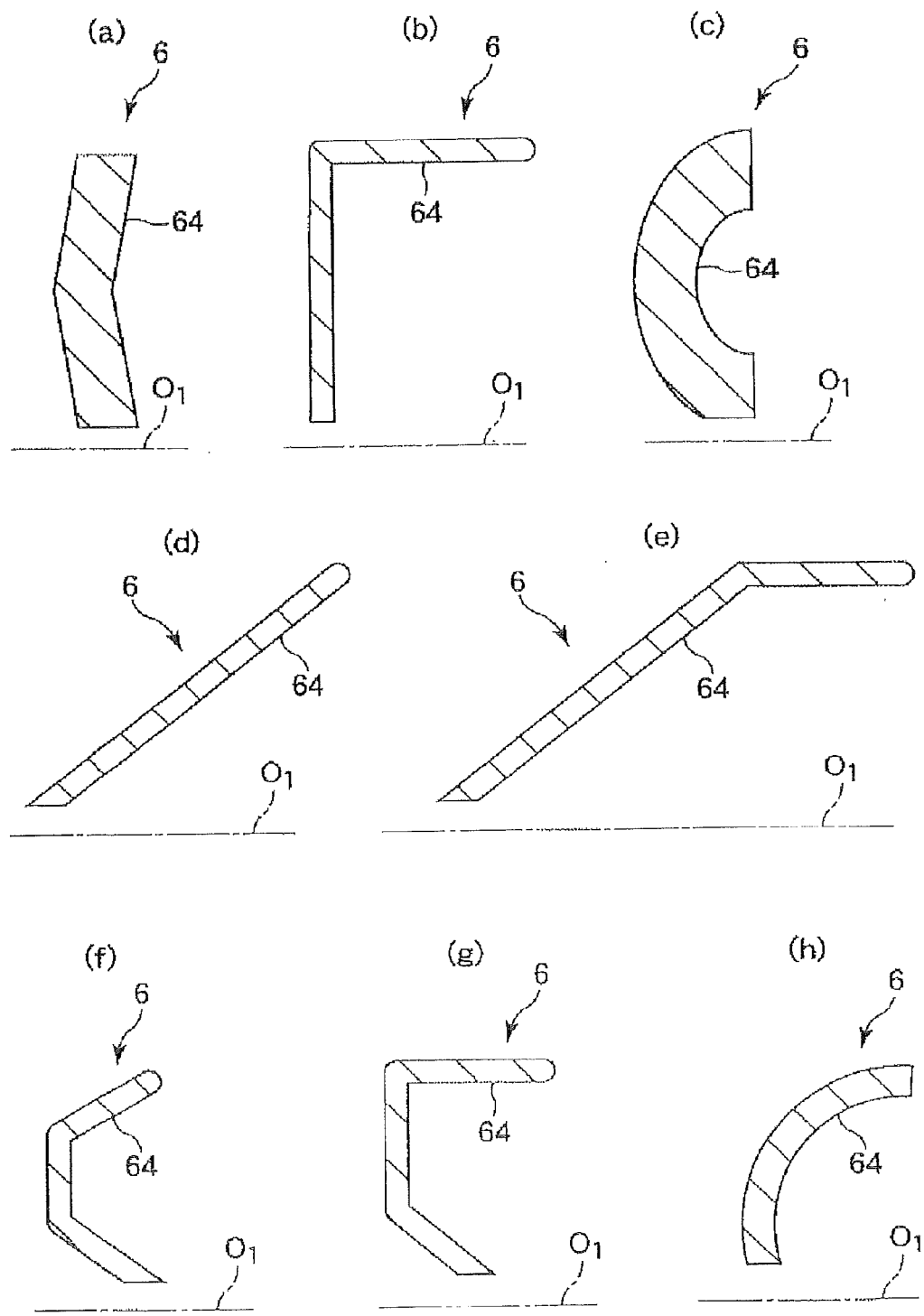
FIG. 19 shows sectional views illustrating other configuration examples of the finger hold of the indwelling needle assembly shown in FIG. 14.
Figure 20:
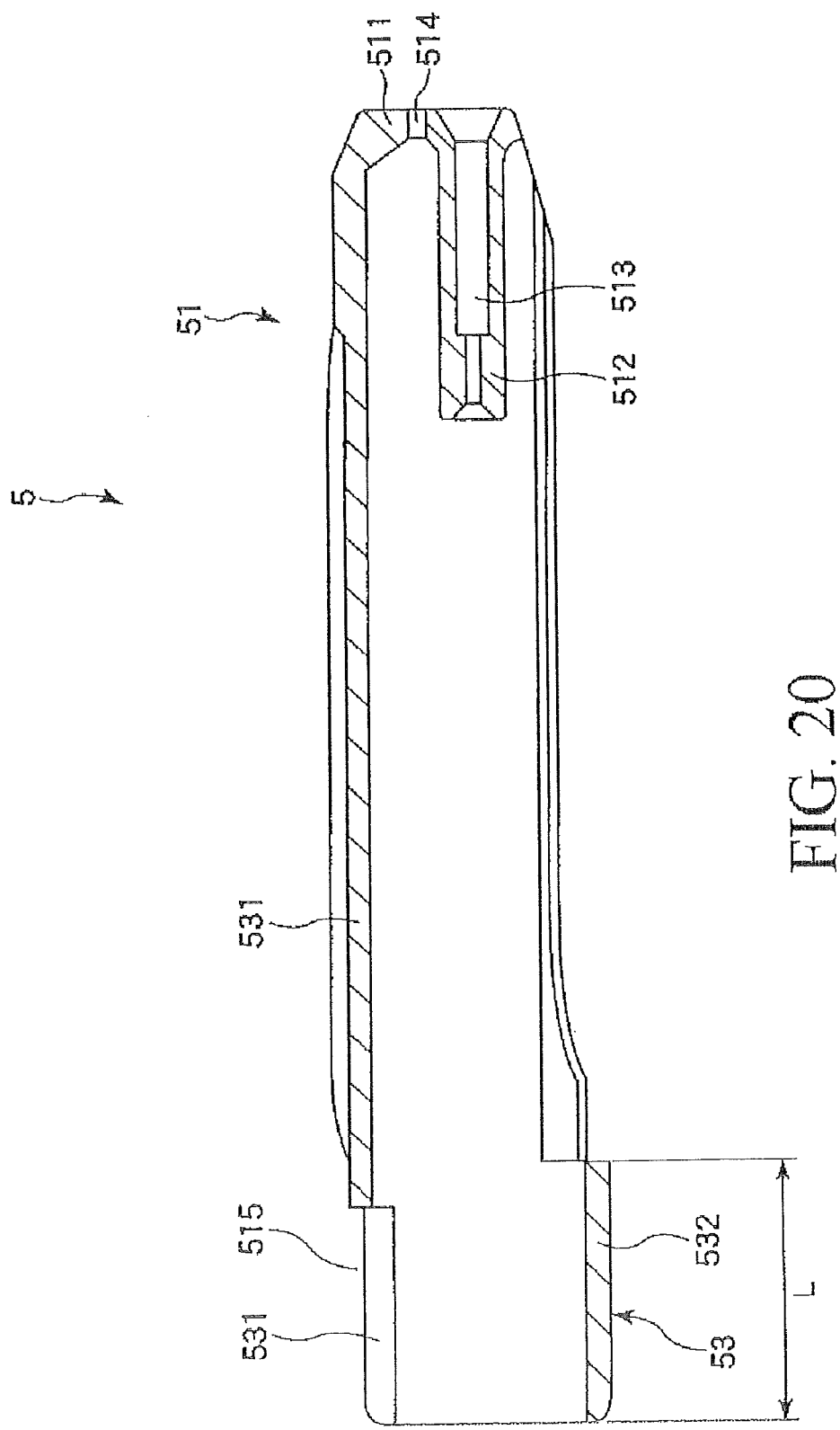
FIG. 20 is a sectional view (i.e., a sectional view taken along line A-A) of an inner-needle hub of the indwelling needle assembly shown in FIG. 14.
Figure 21:
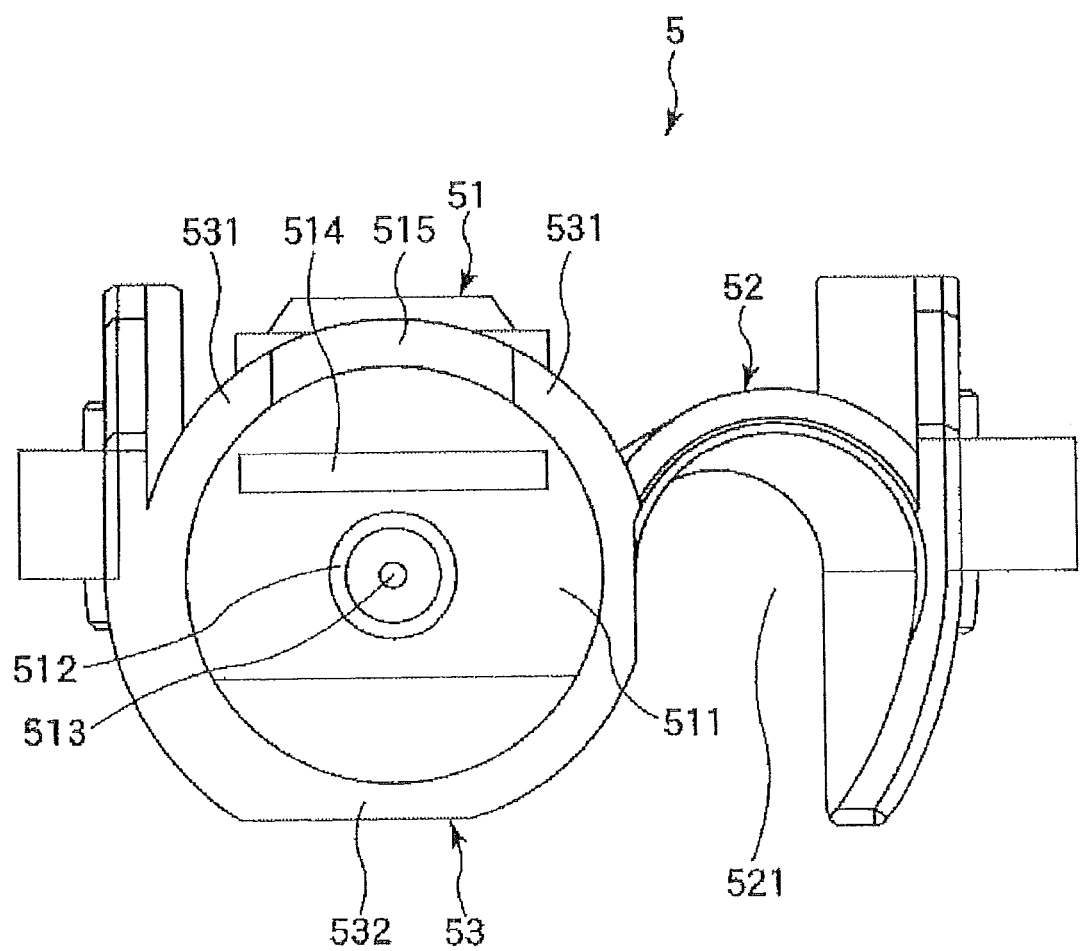
FIG. 21 is a front view of the inner-needle hub of the indwelling needle assembly shown in FIG. 14.
Figure 22:
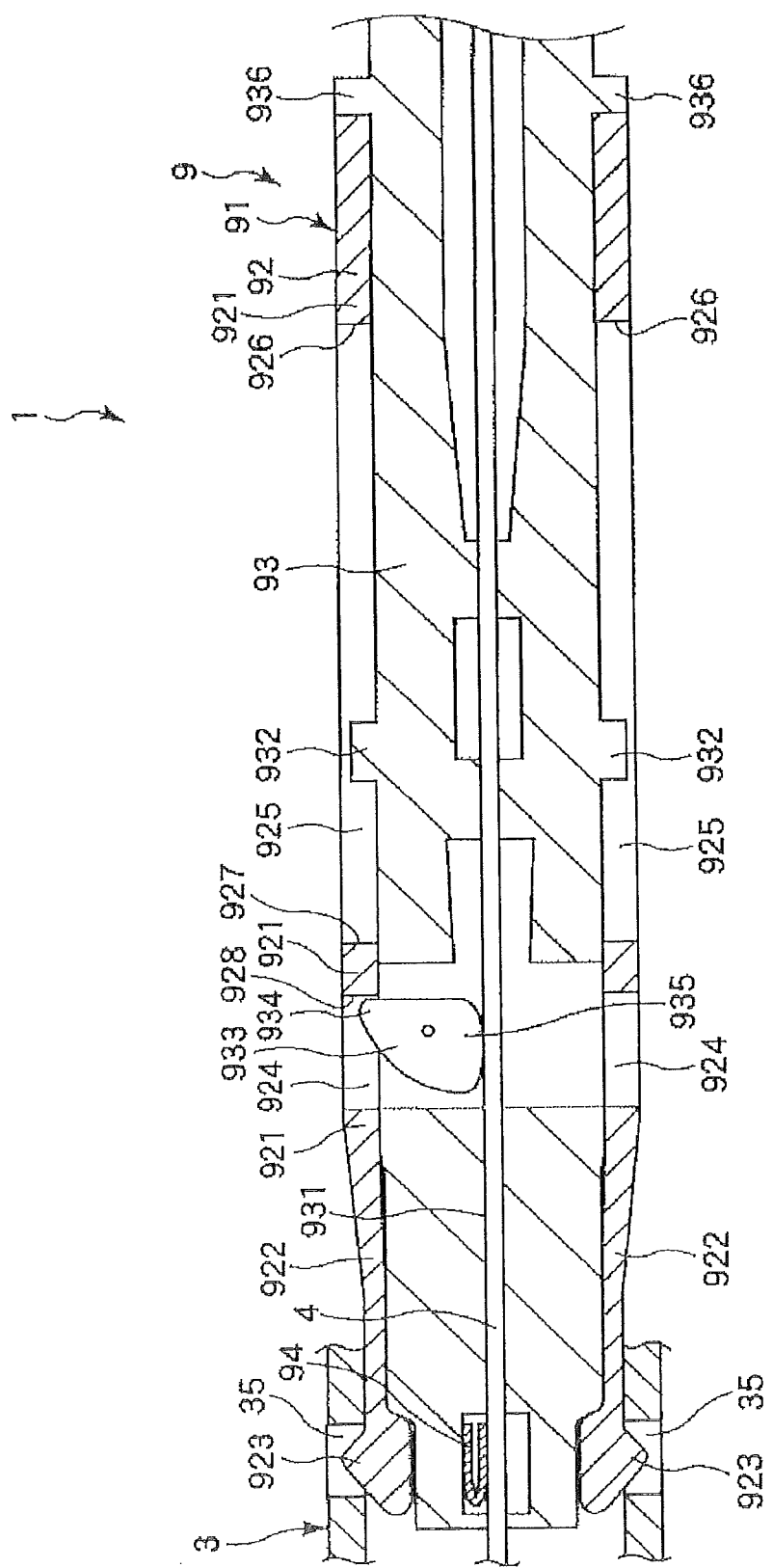
FIG. 22 is a sectional view taken along line B-B of FIG. 16.
Figure 23:
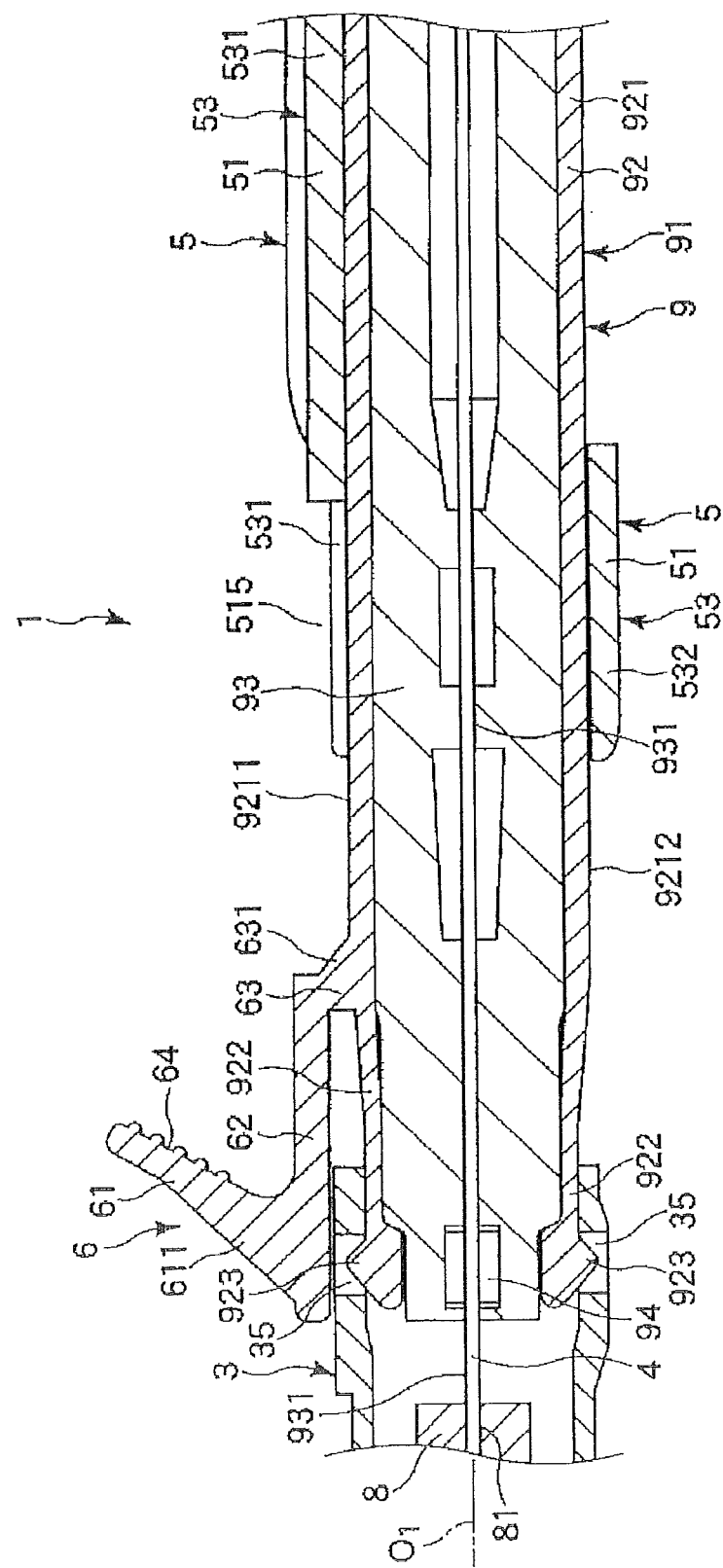
FIG. 23 is a sectional view taken along line A-A of FIG. 14.
Figure 24:
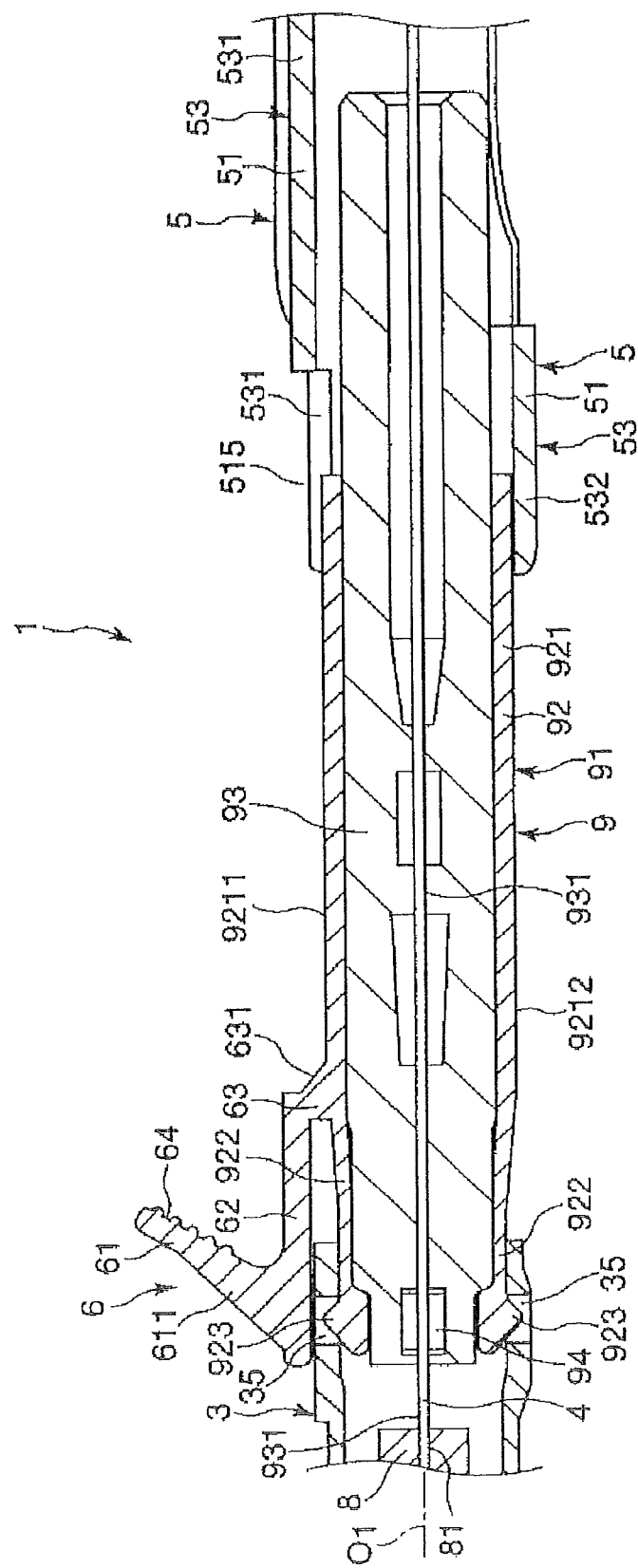
FIG. 24 is a sectional view taken along line A-A of FIG. 14.
Figure 29:
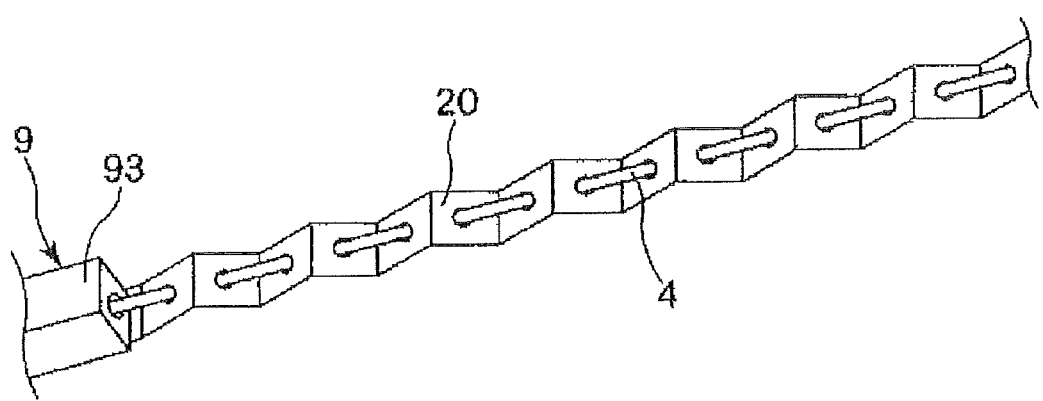
FIG. 29 is a perspective view of a link member of the indwelling needle assembly shown in FIG. 14.
Figure 30:
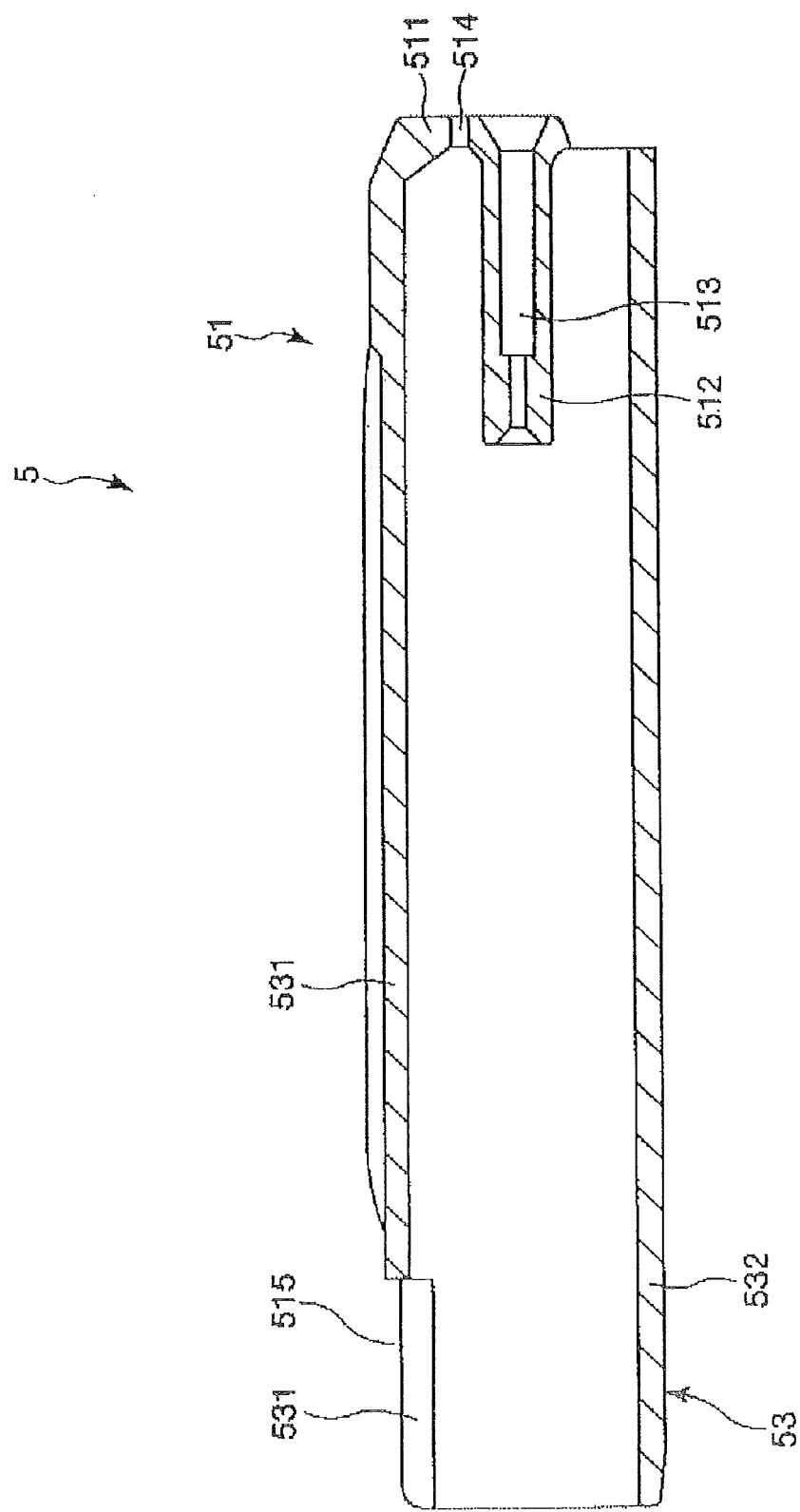
FIG. 30 is a sectional view showing another configuration example of the inner-needle hub in the present invention.
Figure 31:
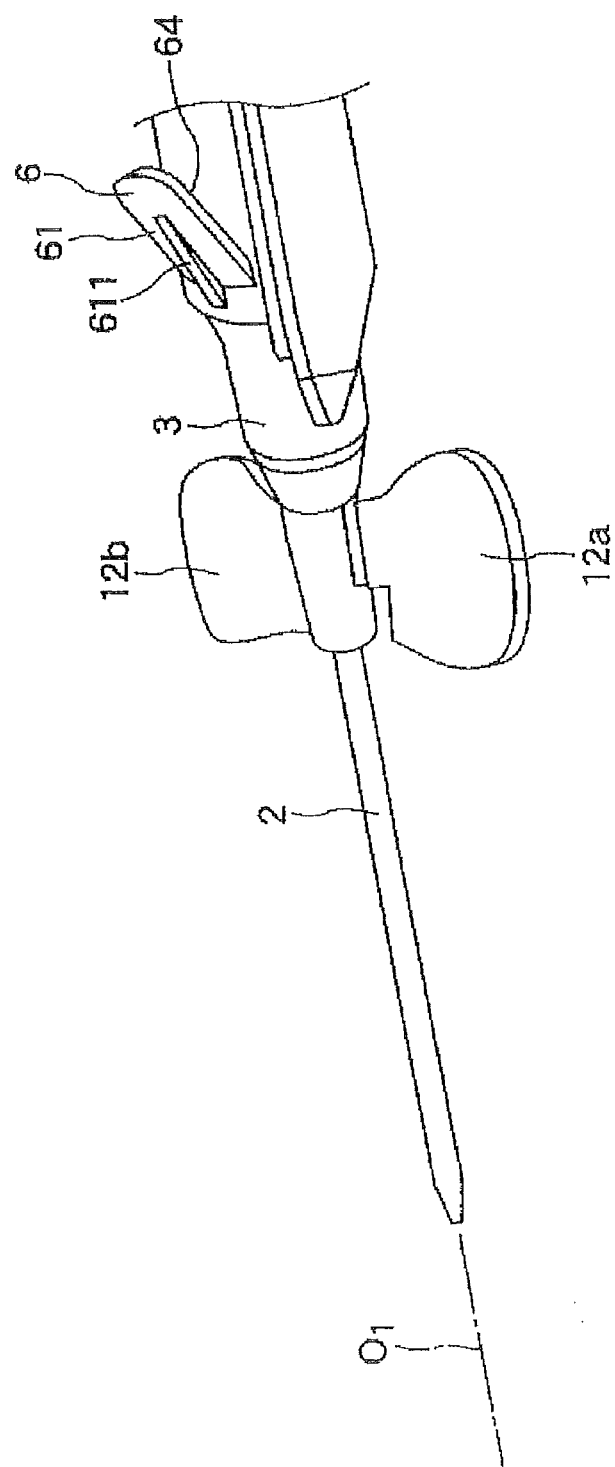
FIG. 31 is a perspective view showing another configuration example of the outer-needle hub in the present invention.

FIG. 14 is a plan view showing a third embodiment of the indwelling needle assembly according to the present invention; FIG. 15 is a sectional view showing an outer needle, an outer-needle hub, an inner needle, and a tube in the indwelling needle assembly shown in FIG. 14; FIG. 16 is a sectional view taken along line A-A of FIG. 14; FIG. 17 is a sectional view (sectional view taken along line A-A) of a finger hold of the indwelling needle assembly shown in FIG. 14; FIG. 18 is a perspective view of the finger hold of the indwelling needle assembly shown in FIG. 14; FIG. 19 shows sectional views illustrating other configuration examples of the finger hold of the indwelling needle assembly shown in FIG. 14; FIG. 20 is a sectional view (sectional view taken along line A-A) of the inner-needle hub of the indwelling needle assembly shown in FIG. 14; FIG. 21 is a plan view of the inner-needle hub of the indwelling needle assembly shown in FIG. 14; FIG. 22 is a sectional view taken along line B-B of FIG. 16; FIGS. 23 and 24 are each sectional views taken along line A-A of FIG. 14; FIGS. 25 to 28 are each sectional views taken along line B-B of FIG. 16; FIG. 29 is a perspective view of a link member of the indwelling needle assembly shown in FIG. 14; FIG. 30 is a sectional view showing another configuration example of the inner-needle hub in the present invention; and FIG. 31 is a perspective view showing another configuration example of the outer-needle hub in the present invention.

Incidentally, hereinafter, descriptions shall be made while referring to the right side in FIGS. 14 and 16 to 31 as "proximal," the left side as "distal," the upper side in FIG. 15 as "proximal," the lower side as "distal," the depth side of the sheet of FIG. 21 as "proximal," and the viewer's side of the sheet as "distal." In addition, in FIGS. 22 and 25 to 28, the inner-needle hub is omitted from the drawings. Further, the inner needle also is shown to be constant in outside diameter, in figures other than FIG. 15.

The indwelling needle assembly 1 shown in each of the figures composes a hollow outer needle 2, an outer-needle hub 3 fixed to a proximal portion of the outer needle 2, an inner needle 4, which is inserted into the outer needle 2, an inner-needle hub 5 fixed to a proximal portion of the inner needle 4, and a tube 7 connected to a proximal portion (or a side section) of the outer-needle hub 3, so that an inner cavity 71 thereof communicates with an inner cavity 21 of the outer needle 2. Configurations of each of these components will be described in detail below.

As the outer needle 2, a needle that has a certain degree of bendability preferably is used. The material constituting the outer needle 2 is preferably a resin material, particularly a soft resin material. Examples of such soft resin materials include fluororesins such as PTFE, ETFE, PFA, etc., olefin reins such as polyethylene, polypropylene, etc., mixtures of olefin resins, polyurethane, polyesters, polyamides, polyether nylon resins, mixtures of olefin resins with ethylene-vinyl acetate copolymer, etc.

A portion or the entirety of the outer needle 2 may enable the inside thereof to be visible. Further, the material constituting the outer needle 2 may have blended therein a radiopaque agent such as, for example, barium sulfate, barium carbonate, bismuth carbonate or tungstic acid, so as to impart a radiopaque property.

To a proximal portion of the outer needle 2, the outer-needle hub 3 is firmly attached (fixed) in a liquid-tight fashion, for example, by a method such as caulking, fusing (heat fusing, ultrasonic fusing, or the like), adhesion with an adhesive, etc.

The outer-needle hub 3 is composed of a substantially tubular member, the interior 31 of which communicates with the inner cavity 21 of the outer needle 2.

The outer-needle hub 3 is formed, in a portion on the right side in FIG. 15, with a channel 32, which opens at one end thereof into the interior 31 of the outer-needle hub 3.

The channel 32 is substantially L-shaped, and the other end thereof opens into a recess 33, which is formed in a hollow or recessed fashion at the proximal end of the outer-needle hub 3, thereby forming an opening 321. In addition, at a distal surface (bottom surface) of the recess 33, a ring-shaped projected portion (connecting portion) 34 is formed, so as to surround the opening 321 and project in the proximal direction.

The projected portion 34 is inserted into the inner cavity 71 of a distal portion of the tube 7, and one end portion (distal portion) of the tube 7 is connected to the outer-needle hub 3. This makes it possible to supply the outer needle 2 (outer-needle hub 3) with a liquid such as a liquid drug, via the tube 7.

In addition, on the left and right sides of the outer-needle hub 3, as shown in FIG. 15, a pair of wings 12a and 12b are formed integrally with the outer-needle hub 3. The wings 12a and 12b are each bendable, and can be opened and closed through bending or curving of the portions near the joints of the wings 12a and 12b with the outer-needle hub 3.

When the outer needle 2 and the inner needle 4 are made to puncture a blood vessel or the like, the wings 12a and 12b are pinched by the fingers into a closed state, whereby the puncturing operation can be performed. Alternatively, a method can be adopted in which puncturing is conducted by pinching the inner-needle hub 5 by a thumb and a middle finger, instead of pinching the wings 12a and 12b, and after the distal end of the outer needle 2 enters the blood vessel, a finger hold 6 (described later) is pressed by an index finger so as to push the outer-needle hub 3 forward, thereby advancing only the outer needle 2 into the blood vessel. When the outer needle 2 is left to indwell, the wings 12a and 12b are set in an opened state, and the wings 12a and 12b in the opened state are fixed to the skin by a pressure sensitive adhesive tape or the like.

In addition, in a proximal portion of the outer-needle hub 3, four holes (recesses) 35 are formed at regular angular intervals, into which projections 923 of four projected sections 922 of a protector cover 92 of a protector 9 (to be described later) may be inserted.

The inner needle 4, which is provided with a sharp point 41 at its distal end, is inserted into the outer needle 2. The indwelling needle assembly 1 is used in a condition whereby the inner needle 4 is inserted into the outer needle 2, and where the inner-needle hub 5 (described later) and the outer-needle hub 3 are maintained in contact with each other (i.e., a condition where the point 41 protrudes from the distal opening 22 of the outer needle 2), namely, the condition shown in FIGS. 14 and 15. Hereinafter, such a condition will be referred to as an "assembled condition."

The length of the inner needle 4 is set to a given length, so that at least the point 41 thereof protrudes from the distal opening 22 of the outer needle 2 in the assembled condition.

The inner needle 4 may be a hollow needle or a solid needle. When the inner needle 4 is a solid needle, sufficient strength can be secured while keeping the outside diameter of the needle small. Further, if the inner needle 4 is a solid needle, when the inner needle 4 is disposed of after completion of an operation, there is no danger of blood remaining inside the inner needle 4, or that blood might flow out therefrom, and high safety is therefore secured.

When the inner needle 4 is a hollow needle, puncturing of a blood vessel by the inner needle 4 results in blood flowing into the hollow section of the inner needle 4, whereby flashback of the blood can be confirmed. In this connection, when the inner needle 4 is a solid needle, blood flows into a gap formed between the inner needle 4 and the outer needle 2, which enables flashback of the blood to be confirmed earlier.

Incidentally, the inner needle 4 may have a configuration in which the inner needle 4 has both a hollow section and a solid section (for example, a configuration in which the needle is hollow on the distal side and solid on the proximal side, the configuration being obtained by filling a portion of the inner cavity of a hollow needle). In this connection, when the inner needle 4 is entirely composed of a single member, the inner needle 4 can be reduced in cost.

In addition, although the inner needle 4 may have a constant outside diameter, in the configuration shown in the figures, the inner needle 4 has a plurality of (in this embodiment, three) sections, which differ in outside diameter. More specifically, the inner needle 4 has a maximum outside diameter section 4a having a maximum outside diameter provided on the distal side (distal-portion side), a minimum outside diameter section 4c having a minimum outside diameter provided on the proximal side, and an intermediate outside diameter section 4b having an intermediate outside diameter, between the maximum diameter and the minimum diameter, provided between the maximum diameter section 4a and the minimum outside diameter 4c.

Further, the inner needle 4 has a first varying outside diameter section 42, provided at a joint between the maximum outside diameter section 4a and the intermediate outside diameter section 4b, and having a continuously varying outside diameter. The inner needle 4 also has a second varying outside diameter section 43, provided between the intermediate outside diameter section 4b and the minimum outside diameter section 4c, and having a continuously varying outside diameter.

At each of the varying outside diameter sections 42 and 43, the outside diameter of the inner needle 4 may vary in a stepwise manner. However, preferably, the outside diameter varies continuously (in a tapered fashion). The latter configuration ensures that when the inner needle 4 is pulled out of the outer needle 2, each of the varying outside diameter sections 42 and 43 can be prevented from becoming caught on a distal edge portion of a slit 81 in a seal member 8 (described later), or on a protector 9 (described later) or the like. Therefore, the operation of pulling the inner needle 4 out of the outer needle 2 can be carried out more smoothly and assuredly.

Incidentally, the varying outside diameter sections 42 and 43 each may be formed simultaneously with manufacturing of the inner needle 4. Alternatively, each may be formed by utilizing a step, which necessarily is carried out at the time of forming a groove 44 (described later).

In addition, the maximum outside diameter section 4a has an outside diameter set nearly equal to the inside diameter of the outer needle 2, so that the maximum outside diameter section 4a makes close contact with an inner surface of the outer needle 2 in a condition where the inner needle 4 is inserted into the outer needle 2. The maximum outside diameter section 4a (distal portion) is provided on an outer peripheral portion thereof with the groove (channel) 44, in a recessed or hollowed form, provided along the longitudinal direction of the inner needle 4. The groove 44 ensures that the distal opening 22 of the outer needle 2 and the inner cavity 31 of the outer-needle hub 3 communicate with each other in a condition where the inner needle 4 is inserted into the outer needle 2. The groove 44 functions as a channel (flow passage) for blood (body fluid) upon puncturing of a blood vessel, for example. Consequently, flashback of the blood can be confirmed assuredly.

Examples of the material constituting the inner needle 4, as described above, include metallic materials such as stainless steel, aluminum, aluminum alloys, titanium, titanium alloys, etc.

The inner-needle hub 5 is firmly attached (fixed) to a proximal portion of the inner needle 4. The inner-needle hub 5 has a protector accommodating section (link member accommodating section) 51, in which the inner needle 4 is inserted, and in which the protector 9 and a link member 20, to be described later, are accommodated (disposed) in the assembled condition, and a tube accommodating section 52 which is provided on a lateral side (the lower side in FIG. 14) of the protector accommodating section 51, and in which the distal side of the tube 7 is accommodated (disposed) in the assembled condition.

The protector accommodating section 51 is formed with a proximal end wall 511 at the proximal end thereof. The proximal end wall 511 is formed with a projected portion (fixing portion) 512, which projects in the distal direction. The projected portion 512 is formed therein with a hole 513, in which to insert a proximal portion of the inner needle 4 (see FIGS. 20 and 21). The proximal portion of the inner needle 4 is inserted into the hole 513, and thereby is firmly attached (fixed) to the projected portion 512.

In addition, the proximal end wall 511 of the protector accommodating section 51 is formed with a hole 514, in which to insert a proximal portion of the link member 20 (see FIGS. 20 and 21). The proximal portion of the link member 20 is inserted into the hole 514, and thereby is firmly attached (fixed) to a proximal portion of the protector accommodating section 51.

Further, the protector 9 and the link member 20 are each located in the protector accommodating section 51 in the assembled condition, and can each be moved relative to the protector accommodating section 51.

In addition, in the assembled condition, the tube 7 is inserted into the inner-needle hub 5, whereby the tube 7 can be prevented from obstructing operations of the indwelling needle assembly 1.

The tube accommodating section 52 is formed with a groove 521, and the tube 7 is disposed in the groove 521. The portion (part) defining (constituting) the groove 521 functions as a guide means for guiding the tube 7. The guide means, or the portion defining the groove 521, guides the tube 7 so that the center axis (axis) $O_2$ thereof at a distal portion of the tube 7 will be substantially parallel to the longitudinal direction of the inner-needle hub 5 (the center axis $O_1$ of the outer needle 2).

Thus, the tube 7 is connected to a proximal portion of the outer-needle hub 3 so that, in the assembled condition, the center axis $O_1$ of the outer needle 2 and the center axis $O_2$ at the proximal portion of the tube 7 are substantially parallel to each other. In other words, the tube 7 protrudes in the proximal direction from the proximal end of the outer-needle hub 3.

In addition, in the case of removing the tube 7 from the inner-needle hub 5 when the inner needle 4 is pulled out from the outer needle 2, the tube 7 can be removed easily and speedily due to the presence of the groove 521 (through the groove 521).

Examples of methods for fixing the inner needle 4 to the inner-needle hub 5 include methods such as fitting, caulking, fusing, adhesion with an adhesive, etc., and combinations thereof. Further, when the inner needle 4 is a hollow needle, it is necessary to provide a sealing means, so that blood flowing backward upon puncturing a blood vessel, for example, is prevented from flying out from the proximal end of the inner needle 4.

While a simple description of the inner-needle hub 5 has been made above, the subsequent part of the description will be given after first generally describing the indwelling needle assembly, including elements such as the protector 9, in order to facilitate understanding.

Each of the inner-needle hub 5 and the outer-needle hub 3 as described above preferably is formed from a transparent (colorless transparent), colored transparent, or semi-transparent resin, whereby visibility of the interiors thereof is secured. This ensures that upon securely puncturing a blood vessel by the outer needle 2, flashback of blood flowing in through the groove 44 in the aforementioned inner needle 4 can be visually confirmed. Further, when the inner needle 4 is solid, flashback of blood due to pressure inside the blood vessel, for example, flows backward through the groove 44, which enables better visibility of flashback.

The materials constituting the outer-needle hub 3, the inner-needle hub 5, and the wings 12a and 12b are not particularly limited. Examples of such materials include various resin materials such as polyolefins such as polyethylene, polypropylene, ethylene-vinyl acetate copolymer, etc., polyurethane, polyamides, polyesters, polycarbonate, polybutadiene, polyvinyl chloride, and polyacetal.

The tube 7 is bendable, and is connected at one end portion thereof to a proximal portion of the outer-needle hub 3, as mentioned above. The other end portion (proximal portion) of the tube 7 is connected to a connector 72. The connector 72 is connected, for example, to another connector provided at an end portion of an infusion line for supplying an infusion (liquid drug) to be administered, or to a mouth portion (distal portion) of a syringe filled with a liquid drug, or the like.

Incidentally, the materials constituting the tube 7 are not particularly limited. Examples of such materials include polyolefins such as polyethylene, polypropylene, ethylene-vinyl acetate copolymer, etc., polyvinyl chloride, polybutadiene, polyamides, and polyesters, among which particularly preferred is polybutadiene. When polybutadiene is used as the material constituting the tube 7, appropriate bendability and chemical resistance can be obtained, together with excellent anti-adsorption effects on chemicals.

Further, the indwelling needle assembly 1 has a cylindrical (block-like) seal member 8 provided at the inside 31 of the outer-needle hub 3. The seal member 8 is formed with a hole or slit through which the inner needle 4 can be passed, and which becomes closed when the thus passed inner needle 4 is pulled out. In the present embodiment, the seal member 8 is formed substantially in its center with a slit 81, which pierces the seal member 8 along the longitudinal direction of the seal member 8.

The slit 81 is formed as a straight line in shape. This permits the slit 81 to remain in a closed state and to be easily placed in an open state. Therefore, the inner needle 4 can be passed smoothly through the seal member 8 (the slit 81). In other words, as will be described later, when the outer needle 2 is advanced using the inner needle 4 as a guide, frictional resistance between the outer surface of the inner needle 4 (the minimum outside diameter section 4*c*) and the inner surface of the slit 81 can be reduced. Consequently, operability of the indwelling needle assembly 1 when performing a puncturing operation can be enhanced.

The seal member 8 has a self-closing property, such that the inner needle 4 passes through the slit 81 in the assembled condition, and further, upon pulling out of the inner needle 4 thus passed, the slit 81 becomes closed by the elastic force (restoring force) of the seal member 8. This ensures that, upon pulling out of the inner needle 4, leakage of liquid from the proximal end of the outer-needle hub 3 can be prevented, and sterility inside of the outer-needle hub 3 can be maintained.

Further, as shown in FIG. 15, in the assembled condition, the minimum outside diameter section 4*c* of the inner needle 4 is located within the slit 81. This ensures a reduced area of contact between the outer surface of the minimum outside diameter section 4*c* and the inner surface of the slit 81, whereby frictional resistance therebetween can be reduced. In addition, it is possible to prevent the seal member 8 (slit 81) from acquiring a certain (deformed) shape, which tends to lower the sealing performance.

Examples of the materials constituting the seal member 8 include a variety of elastic materials, such as various rubber materials (particularly those which have undergone a vulcanizing treatment) such as natural rubber, isoprene rubber, butyl rubber, butadiene rubber, styrene-butadiene rubber, urethane rubber, nitrile rubber, acrylic rubber, fluoro-rubber, silicone rubber, etc., various thermoplastic elastomers based on urethane, polyester, polyamide, olefin, styrene or the like, and mixtures thereof.

In addition, the seal member 8 is formed with a channel 82 therein, at a location different from that of the slit 81. The channel 82 is substantially L-shaped, and opens at a distal surface and a side surface of the seal member 8.

When the seal member 8 is inserted into the outer-needle hub 3 and the opening of the channel 82, which opens on the side surface of the seal member 8, is matched with the opening of the aforementioned channel 32, which opens on the inside 31 of the outer-needle hub 3, a crank-shaped relay channel is formed (completed). The inner cavity 21 of the outer needle 2 and the inner cavity 71 of the tube 7 communicate with each other through the relay channel. This configuration makes it possible for the length of the relay channel to be comparatively small, and prevents the outer-needle hub 3 from becoming enlarged in size.

Incidentally, in the present invention, a configuration may be adopted in which the seal member 8 is not formed with the channel 82, but instead, wherein the opening of the channel 32, which opens at the inside 31 of the outer-needle hub 3, is located on the distal side relative to the seal member 8.

In addition, the indwelling needle assembly 1 is preferably subjected to a friction-reducing treatment, for thereby reducing frictional resistance between the inner surface of the slit 81 and the outer surface of the inner needle 4.

Examples of such a friction-reducing treatment include a treatment in which a lubricant is applied to at least one of the inner surface of the slit 81 and the outer surface (outer peripheral surface) of the inner needle 4, and a treatment in which a layer of a low-friction material (low-friction layer) is formed on the inner surface of the slit 81.

Such a friction-reducing treatment enables a reduction in frictional resistance between the inner needle 4 and the seal member 8, when the outer needle 2 is advanced using the inner needle 4 as a guide. Consequently, the outer needle 2 can be moved smoothly, and the indwelling needle assembly 1 is rendered excellent in operability when a puncturing operation is carried out.

Further, the indwelling needle assembly 1 includes the protector 9, which covers at least the point 41 of the inner needle 4 when the inner needle 4 is pulled out of the outer needle 2. The protector 9 will be described below.

The protector 9 is detachably connected to the outer-needle hub 3. As shown in FIGS. 16 and 22, the protector 9 includes a protector body 91, and a shutter member (shutter means) 94 provided inside the protector body 91.

The protector body 91 has a protector cover 92, and an internal member 93 inserted in the protector cover 92. The protector cover 92 and the internal member 93 are configured so that they can be moved relative to each other and can assume an unmovable state (a state in which they are inhibited from moving relative to each other) as well as a movable state.

The protector cover 92 has a tubular (hollow cylindrical) cover body section 921, and four projected sections 922 which are formed at a distal portion of the cover body section 921 and which project in the distal direction. On the distal sides thereof, the projected sections 922 are inserted into a proximal portion of the outer-needle hub 3. Each of the projected sections 922 is formed at the distal portion thereof with a projection 923, which is inserted into a hole 35 formed in the proximal portion of the outer-needle hub 3, and which becomes caught on an edge portion confronting the hole 35.

When the internal member 93 is inserted in the protector cover 92 so that a distal portion of the internal member 93 is located at a portion (position) of the projections 923 of the projected sections 922 of the protector cover 92, as shown in FIGS. 16 and 22, the internal member 93 inhibits the projections 923 from moving (deforming) toward the center axis (axis) of the inner needle 4, whereby the projections 923 on the edge portions confronting on the holes 35 (a condition in which the projections 923 are caught on the edge portions confronting on the holes 35) is held (maintained). As a result, the connected condition between the protector 9 and the outer-needle hub 3 is maintained.

Figure 27:
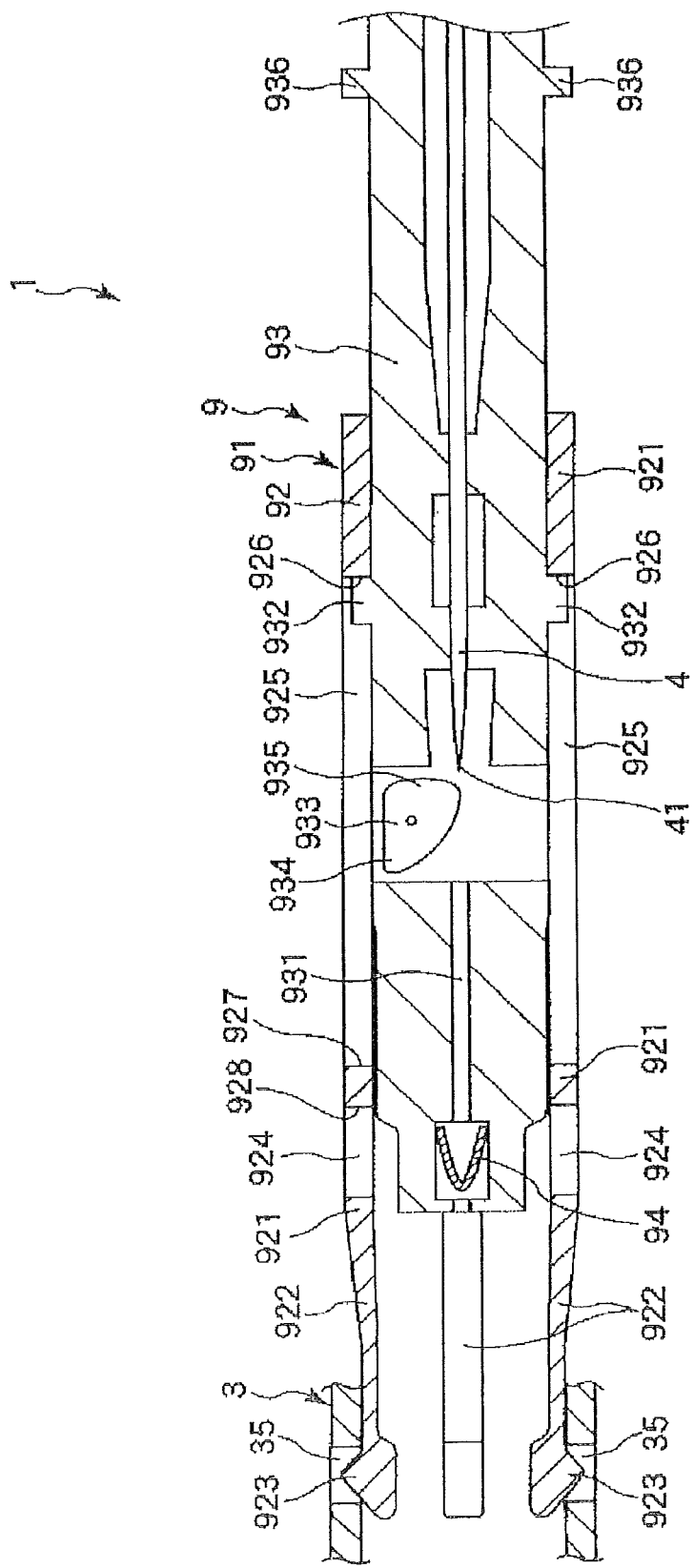
FIG. 27 is a sectional view taken along line B-B of FIG. 16.

Starting from this condition, when the internal member 93 is moved in the proximal direction relative to the protector cover 92, and a distal portion of the internal member 93 reaches the proximal side of the projections 923 of the protector cover 92, the projections 923 are able to move toward the center axis of the inner needle 4, as shown in FIG. 27. In this condition, when the protector cover 92 is moved in the proximal direction relative to the outer-needle hub 3, the projected sections 922 become deformed (deflected) toward the center axis of the inner needle 4, whereby latching of the projections 923 on the edge portions confronting on the holes 35 is released, and the protector 9 becomes disengaged from the outer-needle hub 3.

In addition, the cover body section 921 is formed on both lateral sides thereof with slots 924 and 925 formed along the longitudinal direction (the longitudinal direction of the inner needle 4). The slots 924 are formed in a distal portion of the cover body section 921. The slots 925 are formed on the proximal side relative to the slots 924, and the length of the slots 925 in the longitudinal direction is greater than the length of the slots 924 in the longitudinal direction.

The material constituting the protector cover 92 is not particularly limited. For example, the same materials as mentioned above for the outer-needle hub 3 and the inner-needle hub 5 can be used as the material for the protector cover 92.

The internal member 93 is inserted into the protector cover 92, and is tubular (hollow cylindrical) in shape. Specifically, the internal member 93 is formed in a central portion thereof with an inner-needle passage 931 through which the inner needle 4 is passed, and which pierces the internal member 93 from the proximal end to the distal end of the internal member 93. The shutter member 94 is accommodated in a distal portion of the internal member 93, at an intermediate position of the inner-needle passage 931.

The material constituting the internal member 93 is not particularly limited. For example, the same materials as those mentioned above for the outer-needle hub 3 and the inner-needle hub 5 can be used as the material for the internal member 93.

Figure 25:
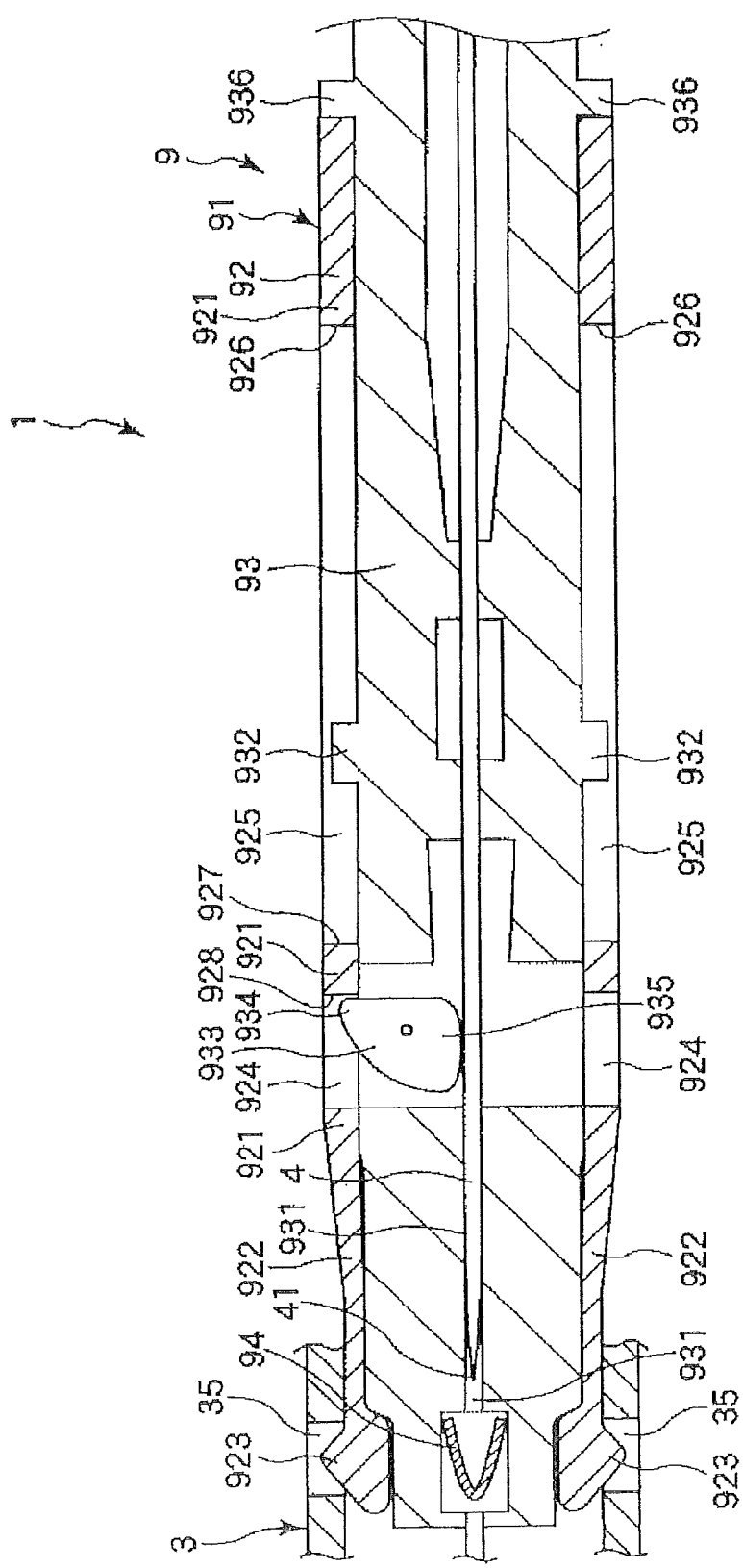
FIG. 25 is a sectional view taken along line B-B of FIG. 16.

The shutter member 94 is formed by bending an elastic (elastically deformable) belt-like plate member into a substantially V-shaped form, the opening angle of which can be varied (opened and closed), thus permitting the shutter member 94 to assume (be deformed into) a first posture, in which the inner needle 4 can be inserted in (passed through) the inner-needle passage 931 (i.e., the posture shown in FIGS. 16 and 22), and a second posture in which the passage of the point 41 of the inner needle 4 is inhibited (i.e., the posture shown in FIG. 25).

When the inner needle 4 is inserted entirely into (passed through) the inner-needle passage 931, as shown in FIGS. 16 and 22, the shutter member 94 is accommodated in a folded state, so that the opening angle is reduced, and hence the shutter member 94 is in the first posture. In this condition, the protector 9 can be moved in the longitudinal direction of the inner needle 4 (along the direction of the center axis $O_1$ of the outer needle 2) relative to the inner needle 4 and the inner-needle hub 5.

When the inner-needle hub 5 is moved in the proximal direction relative to the protector 9, starting from this condition, and as shown in FIG. 25, the point 41 of the inner needle 4 reaches the proximal side of the shutter member 94, and the shutter member 94 opens under its own elastic force (restoring force) into the second posture, thereby cutting off the inner-needle passage 931. In this condition, the shutter member 94 inhibits the point 41 from moving (passing) in the distal direction beyond the shutter member 94.

The material constituting the shutter member 94 is not particularly limited, insofar as it can inhibit the passage of the point 41 therethrough. Examples of such a material include the same various resin materials as those mentioned above for the outer-needle hub 3 and the inner-needle hub 5, as well as various metallic materials such as stainless steel, aluminum alloys, copper, titanium, etc.

In addition, the thickness of the shutter member 94 is not particularly limited. For instance, the thickness is preferably about 0.04 to 0.2 mm, and more preferably, about 0.04 to 0.1 mm.

Further, a lubricant preferably is applied to a surface of the shutter member 94. This reduces frictional resistance (sliding resistance) between the outer peripheral surface of the inner needle 4 and the shutter member 94, in a condition where the shutter member 94 is in the first posture, thus enabling smoother movement of the inner needle 4 relative to the protector 9.

Incidentally, part of the shutter member 94 may be fixed to the internal member 93 by methods, for example, such as embedding, fusing, adhesion with an adhesive, etc. Further, in the present invention, the shutter member 94 is not limited to the configuration shown in the figures, and the shutter member 94 may be formed in any shape or configuration.

In addition, the internal member 93 is formed, on both lateral sides at a central portion thereof, with projected portions 932, which are inserted into corresponding slots 925 in the protector cover 92.

As a result, the internal member 93 can be prevented from rotating (turning) relative to the protector cover 92.

Further, when the internal member 93 is moved in the proximal direction relative to the protector cover 92, as shown in FIG. 27, the projected portions 932 of the internal member 93 abut on proximal-side edge portions 926 of the slots 925 in the protector cover 92. This inhibits the internal member 93 from moving in the proximal direction relative to the protector cover 92. Also, in this condition, when the internal member 93 is moved in the proximal direction relative to the protector cover 92, the internal member 93 and the protector cover 92 are moved as one body in the proximal direction. In addition, the internal member 93 can be prevented from slipping off (becoming disengaged) from the protector cover 92.

Further, a lock member 933 is rotatably disposed between the arrangement position (distal portion) of the shutter member 94, at a side section on the upper side in FIG. 22, and the projected portions 932 of the internal member 93.

When the inner needle 4 is located at the position of the lock member 933, i.e., when the inner needle 4 is inserted entirely within (passed through) the inner-needle passage 931, as shown in FIG. 22, the inner needle 4 makes contact with a bottom portion (proximal portion) 935 of the lock member 933, and the lock member 933 is held in a posture such that the tip portion 934 thereof is directed away from the inner needle 4 (directed toward the upper side in FIG. 22) (rotation of the lock member 933 is inhibited). When the lock member 933 assumes this posture, the tip portion 934 thereof can abut on (be engaged with) a proximal-side edge portion 928 of the slot 924 and a distal-side edge portion 927 of the slot 925.

Figure 26:
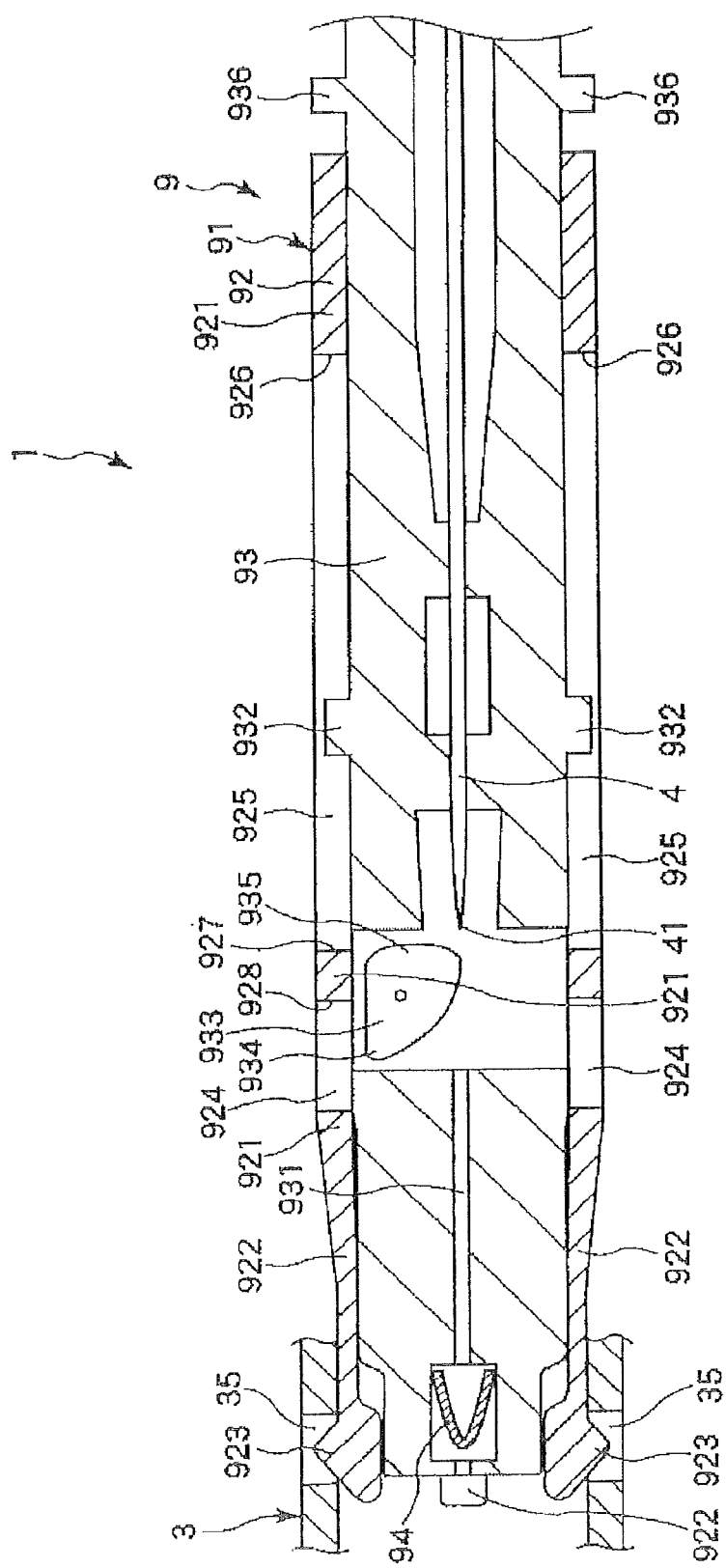
FIG. 26 is a sectional view taken along line B-B of FIG. 16.

In addition, when the inner needle 4 is located on the proximal side relative to the portion of the lock member 933 (is not located at the portion of the lock member 933), as shown in FIG. 26, rotation of the lock member 933 is allowed. Thus, the lock member 933 can assume a posture in which no part thereof makes contact with the edge portion 927 or 928.

Further, the internal member 93 is formed, on both lateral sides at a proximal portion thereof, with ribs (flanges) 936, which are capable of abutting on a proximal surface of the cover body section 921 of the protector cover 92.

In the assembled condition, as shown in FIGS. 16 and 22, the internal member 93 is inserted into the protector cover 92, and a distal portion of the internal member 93 is located at portions of the projections 923 of the projected sections 922 of the protector cover 92. As mentioned above, this ensures that the catch of the projections 923 on the edge portions confronting on the holes 35 is maintained, and thus the connected condition between the protector 9 and the outer-needle hub 3 is held securely.

In addition, by abutment of the ribs 936 of the internal member 93 on the proximal end of the cover body section 921 of the protector cover 92, the internal member 93 is inhibited from moving in the distal direction relative to the protector cover 92.

On the other hand, the inner needle 4 is inserted entirely into the inner-needle passage 931, and the lock member 933 is held in a posture so that the tip portion 934 thereof is directed away from the inner needle 4 (directed toward the upper side in FIG. 22), as mentioned above. With the tip portion 934 of the lock member 933 located inside the slot 924 and abutting on the proximal-side edge portion 928 of the slot 924, the internal member 93 is inhibited from moving in the proximal direction relative to the protector cover 92.

This ensures that the internal member 93 and the protector cover 92 are moved together as one body, whereby the protector 9 and the outer-needle hub 3 are moved integrally.

According to the protector 9 described above, after use, the point 41 of the inner needle 4 can be covered speedily and safely through a simple operation. In addition, by action of the shutter member 94, once the point 41 is covered, it is prevented from protruding from the distal end of the protector body 91 (the internal member 93) of the protector 9. Therefore, when the inner needle 4 is disposed of, or in similar situations, an accident in which the operator or the like mistakenly punctures his or her hand or finger with the point 41 is prevented from occurring, and thus high safety is secured.

In addition, as shown in FIG. 29, the indwelling needle assembly 1 has the link member 20, which functions as an anti-slipping means, for preventing the protector 9 from slipping off from the point 41 of the inner needle 4 when the protector 9 covers the point 41, and also functions as a linking means for linking the protector 9 and the inner-needle hub 5 to each other.

The link member 20 is configured to link the internal member 93 of the protector 9 and the inner-needle hub 5 to each other. This ensures that when the inner-needle hub 5 is moved in the proximal direction, the internal member 93 (the protector 9) is pulled (moved) in the proximal direction through the link member 20.

Moreover, the link member 20 is bellows-like in form, and can therefore be extended and contracted. The link member 20 has a length such that when the link member 20 is extended maximally (is fully extended), the point 41 of the inner needle 4 is located on the proximal side relative to the lock member 933, yet at the same time, the point 41 is accommodated inside the internal member 93 (i.e., will not slip off from the internal member 93).

Thus, the link member 20 links the internal member 93 and the inner-needle hub 5 to each other, and has a length such that the point 41 is accommodated in the internal member 93 in a condition where the link member 20 is extended maximally. This ensures that the protector 9 is securely prevented from slipping off from the inner-needle hub 5 or the point 41. Also, the condition whereby the point 41 is covered by the protector 9 can be maintained assuredly. Consequently, when the inner needle 4 is disposed of, or in similar situations, an accident in which the operator or the like mistakenly punctures his or her hand or finger with the point 41 is prevented from occurring, and high safety is secured.

In addition, the link member 20 is contracted, or folded, in the assembled condition, whereas the link member 20 is extended, or spread, in the condition where the inner needle 4 is pulled out of the outer needle 2 and the point 41 is covered by the protector 9.

The aforementioned link member 20 is contracted in the assembled condition, and in the contracted state, the link member 20 is accommodated in the inner-needle hub 5. This ensures that the link member 20 will not present an obstacle when a puncturing operation is performed, so that operability of the indwelling needle assembly 1 is enhanced. Further, the indwelling needle assembly 1 can be reduced in size.

In addition, in a condition where the link member 20 is contracted, as well as a condition where the link member 20 is extended, the inner needle 4 penetrates through the link member 20. This ensures that the inner needle 4 functions as a guide for the link member 20 when the link member 20 is extended and contracted. Therefore, for example, when the indwelling needle assembly 1 is placed in an assembled condition (i.e., is manufactured), it is possible to securely prevent the link member 20 from becoming contracted in an unintended state. More specifically, the link member 20 is prevented from becoming contracted without being accommodated in the inner-needle hub 5.

Further, the link member 20 has a self-restoring property (restoring property) for returning to its natural state. More specifically, in a state where the link member 20 is contracted and is shorter than its natural state, the link member 20 functions as a biasing means and is biased in the extending direction by the restoring force thereof. On the other hand, when in an extended state longer than its natural state, the link member 20 functions as a biasing means and is biased in the contracting direction by its restoring force. The term "natural state" implies a state in which no external force is exerted on the link member 20.

In addition, as shown in FIGS. 16 to 18, the finger hold (tab) 6, which is pressed by a finger so as to move the outer needle 2 in the distal direction relative to the inner needle 4, is formed (provided) so as to project on the protector cover 92 of the protector 9. The protector cover 92 and the finger hold 6 are formed as a unitary body. In addition, the finger hold 6 projects in an upward direction.

Incidentally, a structure may be adopted in which the protector cover 92 and the finger hold 6 are formed as separate members, which are joined respectively to each other. In this case, the material constituting the finger hold 6 is not particularly limited. For example, the same materials as those mentioned above as materials for the outer-needle hub 22 and the inner-needle hub 32 can be used for the finger hold 6. Further, the finger hold 6 may project in a direction other than the illustrated direction (for instance, sideways).

Herein, during use of the indwelling needle assembly 1, the term "upward direction" refers to the direction in which the skin (body skin), in the vicinity of the part of the patient (the person on whom the assembly is used) to be punctured by the outer needle 2 (the inner needle 4), is oriented. Namely, the "upward direction" refers to the direction from the skin side toward the side of the indwelling needle assembly 1. In other words, the "upward direction" is the direction in which a cutting edge surface (not shown) formed at the point 41 of the inner needle 4 is oriented.

The finger hold 6 is provided on the proximal side thereof with a finger hold surface 64, on which to place a finger. The finger hold 6 has a shape such that, when the outer needle 2 is moved in the distal direction relative to the inner needle 4, a force in an upward direction (vertically upward direction) relative to the center axis (axis) $O_1$ of the outer needle 2, i.e., a force in the direction in which the finger hold 6 projects (projecting direction) (the upward direction in FIG. 17), is capable of acting on the finger hold 6.

This ensures that when the outer needle 2 is moved in the distal direction relative to the inner needle 4 during a puncturing operation, the finger hold 6 can be pressed by the finger in the distal direction, while lifting up (in the manner of lifting up) the finger hold 6 in the projecting direction thereof (the upward direction in FIG. 17). This, by a synergistic effect with a support section 53 (described later), ensures that the center axis $O_1$ of the outer needle 2 can be inhibited from becoming inclined relative to the center axis $O_1$ of the outer needle 2, in a condition before the finger hold 6 is pressed, while also ensuring that the outer needle 2 can be moved straightly along its center axis $O_1$, namely, along the direction of the center axis $O_1$, without becoming bent. Consequently, the outer needle 2 can be moved (advanced) smoothly, and excellent operability is secured.

In the present embodiment, the finger hold 6 is formed at a distal portion of the cover body section 921 of the protector cover 92, wherein the finger hold 6 has a shape obtained by bending a plate member, as shown in FIG. 17.

Specifically, the finger hold 6 is composed of an inclined portion (inclined plate) 61, which is disposed on the distal side relative to the cover body section 921 and is inclined toward the proximal side, a base portion 63 fixed to a distal portion of the cover body section 921, and a connecting portion (connecting plate) 62 connecting the inclined portion 61 and the base portion 63 to each other. A proximal-side surface of the inclined portion 61 constitutes the finger hold surface 64. In the case of such a finger hold 6, the finger is inserted into a space between the finger hold surface 64 (the inclined portion 61) and the connecting portion 62, whereby the finger becomes caught on the finger hold surface 64, and in this condition, the finger hold 6 can be pressed by the finger in the distal direction, while being lifted up in the projecting direction thereof.

In addition, the positional relationship between the finger hold 6 and the center axis $O_1$ of the outer needle 2 is not particularly limited. Preferably, however, the finger hold 6 is located on the center axis $O_1$ of the outer needle 2 in plan view (as viewed from the upper side in FIG. 17), as shown in FIG. 14. This enables the outer needle 2 to be moved along the direction of the center axis $O_1$ more smoothly and assuredly.

Further, the positional relationship between the base portion 63 as a fixed point (fixed part) of the finger hold 6 and the finger hold surface 64 is not particularly limited. Preferably, however, the base portion 63 is located on the proximal side relative to a tip 641 of the finger hold surface 64. In the illustrated configuration, the base portion 63 is located on the proximal side relative to a base end 642 of the finger hold surface 64. However, configurations other than the configuration shown may be provided, in which the base portion 63 preferably is located, for example, between the tip 641 and the base end 642 of the finger hold surface 64.

In addition, the finger hold surface 64 of the finger hold 6 is formed with a rugged pattern (for example, a plurality of ribs arrayed in an up-down direction on the finger hold surface 64), which functions as an anti-slipping means for the finger. This ensures that when the finger hold 6 is pressed by the finger so as to move the outer needle 2 in the distal direction, the finger can be prevented from slipping out of position.

Further, the finger hold 6 has a reinforcement section for suppressing ending of the finger hold 6 when the finger hold 6 is pressed by the finger. The reinforcement section is composed of a rib 611, which is formed at the inclined portion 61 on an opposite side from the finger hold surface 64, and a rib 631 formed at the base portion 63.

In addition, the dimensions of the finger hold 6 are not particularly limited. Preferably, however, the width (w) of the finger hold surface 64 of the finger hold 6 is about 2 to 50 mm, and more preferably, about 2 to 30 mm.

If the width (w) is less than the lower limit, the finger may slip off from the finger hold surface 64, thus making the puncturing operation difficult to carry out. On the other hand, if the width (w) is more than the upper limit, the finger hold 6 may present an obstacle.

Further, the height (h) of the finger hold 6 from the outer surface of the protector cover 92 (the protector 9) is preferably about 1 to 50 mm, and more preferably, about 2 to 20 mm.

If the height (h) is less than the lower limit, it may become impossible to locate a finger on the lower side of the finger hold surface 64 and allow the finger to be caught on the finger hold surface 64. If the height (h) is more than the upper limit, on the other hand, the finger hold 6 may become an obstacle.

The finger hold 6, preferably, satisfies the following conditions (1) or (2).

(Condition 1)

The finger hold surface 64 of the finger hold 6, in a condition where the rugged pattern (anti-slipping means) is omitted, or in a condition prior to providing the rugged pattern, has a portion to which the normal 11 extending toward the proximal side is directed, toward the side of the center axis $O_1$ of the outer needle 2. Incidentally, in the illustrated configuration, over substantially the entirety of the finger hold surface 64, the normal 11 that extends toward the proximal side is directed toward the side of the center axis $O_1$ of the outer needle 2.

This ensures that, when the outer needle 2 is moved in the distal direction relative to the inner needle 4 during a puncturing operation, the finger hold 6 can more easily and assuredly be pressed by the finger in the distal direction, while being lifted up in the projecting direction thereof, whereby enhanced operability is secured.

(Condition 2)

The finger hold surface 64 of the finger hold 6, in a condition where the rugged pattern (anti-slipping means) has been omitted, or in a condition before the rugged pattern is provided, has a surface (portion), of which the angle θ to the center axis $O_1$ of the outer needle 2 is less than 90° (inclusive of 0°). When the finger hold surface 64 is a plane (planar surface), the aforementioned surface is defined by the plane. When the finger hold surface 64 is a curved surface, the aforementioned surface is defined by a plane (a tangent line in side view), which is tangential to the curved surface. Incidentally, in the illustrated configuration, over the entirety of the finger hold surface 64, the angle θ with respect to the center axis $O_1$ of the outer needle 2 is less than 90°.

This ensures that, when the outer needle 2 is moved in the distal direction relative to the inner needle 4 during a puncturing operation, the finger hold 6 can more easily and assuredly be pressed by the finger in the distal direction, while being lifted up in the projecting direction thereof, whereby enhanced operability is secured.

In addition, the angle θ to the center axis $O_1$ of the outer needle 2 preferably is not more than 85°, more preferably is about 30° to 80°, and even more preferably, is about 45° to 75°.

Further, the shape of the finger hold 6 is not limited to the shape shown in the figures. Specifically, it is sufficient if the finger hold 6 has a shape such that, when the outer needle 2 is moved in the distal direction relative to the inner needle 4, a force in the projecting direction (upward direction) relative to the center axis $O_1$ of the outer needle 2 can act on the finger hold 6. Other configuration examples, apart from the aforementioned example, include the configurations shown in (a) to (h) of FIG. 19.

Each of the finger holds 6, shown respectively in (a) to (h) of FIG. 19, satisfies the aforementioned conditions (1) and (2).

Meanwhile, in the indwelling needle assembly 1, as shown in FIGS. 16, 20 and 21, the inner-needle hub 5 includes the support section (support means) 53 for supporting the cover body section 921 of the protector cover 92, which makes up a supported section formed in the protector 9.

The support section 53 is formed in the protector accommodating section 51 of the inner-needle hub 5. The support section 53 is configured such that, when the outer needle 2 is moved in the distal direction relative to the inner needle 4, the support section 53 supports the cover body section 921, so as to inhibit the center axis (axis) $O_1$ of the outer needle 2 from becoming inclined relative to the center axis $O_1$ of the outer needle 2 in a condition prior to the finger hold 6 being pressed (in a condition before distal movement of the outer needle 2 is initiated). More particularly, the support section 53 functions to inhibit the distal side of the center axis $O_1$ of the outer needle 2 from becoming inclined toward the opposite side from the finger hold 6, relative to the center axis $O_1$ of the outer needle 2, in a condition before the finger hold 6 is pressed.

This ensures that, even if the finger hold 6 is absent, when the outer needle 2 is moved in the distal direction relative to the inner needle 4, such as when the outer needle 2 is moved in the distal direction relative to the inner needle 4 during a puncturing operation, the outer needle 2 can be moved straightly along its center axis $O_1$, or moved along the direction of the center axis $O_1$, without becoming bent. Consequently, the outer needle 2 can be moved smoothly.

Further, in the illustrated configuration, as shown in FIGS. 16, 20 and 21, the overall shape of the support section 53 is a shape obtained by removing a portion from a substantially hollow cylindrical (tubular) shape. More specifically, the support section 53 has a first wall portion (upper-side wall portion) 531 in contact with an outer surface 9211 on the finger hold 6 side (on the upper side in FIG. 16) of the cover body section 921, and a second wall portion (lower-side wall portion) 532 in contact with an outer surface 9212 on the opposite side from the finger hold 6 (on the lower side in FIG. 16) of the cover body section 921.

In the assembled condition (a condition in which the inner needle 4 is inserted into the outer needle 2 and where the point 41 protrudes from the distal opening 22 of the outer needle 2), each of the first wall portion 531 and the second wall portion 532 abuts against (is in contact with) the cover body section 921.

In addition, in the assembled condition, the first wall portion 531 is provided over a range from a distal portion to a proximal portion (a part corresponding to a proximal portion of the cover body section 921) of the protector accommodating section 51 (the inner-needle hub 5). In other words, the first wall portion 531 is provided over substantially the entire length of the protector accommodating section 51 (the inner-needle hub 5). This ensures that the proximal portion of the cover body section 921 remains in abutment with (in contact with) the first wall portion 531, from the assembled condition and until the cover body section 921 becomes disengaged from the protector accommodating section 51.

Further, the second wall portion 532 is provided at a distal portion of the protector accommodating section 51 (the inner-needle hub 5). This ensures that the proximal portion, or a portion on the distal side relative to the proximal portion of the cover body section 921, remains in abutment with (in contact with) the second wall portion 532, from the assembled condition and until the cover body section 921 becomes disengaged from the protector accommodating section 51.

As a result, from the assembled condition and until the cover body section 921 becomes disengaged from the protector accommodating section 51, the cover body section 921 is supported by the first wall portion 531 and the second wall portion 532, whereby the center axis $O_1$ of the outer needle 2 can be prevented from becoming inclined.

The length L of the second wall portion 532 along the direction of the center axis $O_1$ is not particularly limited. Preferably, however, the length L is not less than 1 mm, and more specifically, is in a range from about 1 mm to the entire length of the protector accommodating section 51 (the inner-needle hub 5), and more preferably, in a range from about 3 mm to the entire length of the protector accommodating section 51.

When the length L of the second wall portion 532 is less than the lower limit, the portion may lack sufficient strength.

A configuration example of the inner-needle hub 5, in a case where the second wall portion 532 is provided substantially over the entire length of the protector accommodating section 51 (the inner-needle hub 5), is shown in FIG. 30.

In addition, the support section 53 and the cover body section 921 preferably are configured such that the support section 53 supports the cover body section 921 until the outer needle 2 has been moved by a given distance of at least half the length of the outer needle 2 from the assembled condition. More specifically, the lengths of the cover body section 921, the first wall portion 531 and the second wall portion 532 along the direction of the center axis $O_1$ preferably are set so that the cover body section 921 remains in abutment with the first wall portion 531 and the second wall portion 532, without becoming disengaged from the protector accommodating section 51, until the outer needle 2 has been moved by a distance of at least half the length of the outer needle 2 from the assembled condition.

This ensures that, when the outer needle 2 is moved in the distal direction relative to the inner needle 4, the center axis $O_1$ of the outer needle 2 can be prevented more securely from becoming inclined.

Further, the length of the cover body section (supported section) 921 of the protector 9 preferably is set to be shorter than the length of the outer needle 2. Further, the length of the protector 9, in a condition where the protector 9 is connected to the outer-needle hub 3 (the assembled condition), namely, in a condition where the internal member 93 is inserted into the protector cover 92 and where the distal portion of the internal member 93 is located at a portion of the protector cover 92 corresponding to the projections 923 of the projected sections 922 (see FIGS. 16 and 22), preferably is set to be shorter than the length of the outer needle 2.

In addition, a configuration is adopted in which the support section 53 ultimately does not support the cover body section 921 of the protector 9 during use of the indwelling needle assembly 1. More particularly, it is preferable to adopt a configuration in which the support section 53 does not support the cover body section 921 of the protector 9, before the point 41 of the inner needle 4 is covered by the shutter member 94 of the protector 9. The latter configuration can be realized by setting the length of the cover body section 921, and more particularly, the length of the protector 9 in the aforementioned condition, so as to be shorter than the length of the outer needle 2 by a predetermined length value.

If the length of the protector 9 in the aforementioned condition is longer than the length of the outer needle 2, when the outer needle 2 is moved in the distal direction relative to the inner needle 4, the support section 53 continues to support the cover body section 921 of the protector 9, so that the inner-needle hub 5 can only be pulled straight. This makes the operation (use thereof) difficult to carry out, in the event that the operator has small hands (or short fingers).

When the length of the protector 9 in the aforementioned condition is set to be shorter than the length of the outer needle 2 by a predetermined length value, it is possible nevertheless, at the time of advancing the outer needle 2 into a blood vessel, to support the cover body section 921 by the support section 53, and thereby to move the outer needle 2 without inclining the outer needle 2 from the center axis $O_1$. Thereafter, the support section 53 does not support the cover body section 921, whereby the support section 53 enables the inner-needle hub 5 to be moved also in an inclined direction. Hence, it is advantageous in that an operator having small hands can easily operate the indwelling needle assembly having the illustrated configuration.

Incidentally, in the configuration shown, the support section 53 supports the cover body section 921 until the outer needle 2 is moved by a distance of about ⅔ times the length thereof from the assembled condition. More specifically, the cover body section 921 remains in contact with the first wall portion 531 and the second wall portion 532, without becoming disengaged from the protector accommodating section 51, until the outer needle 2 is moved by a distance of about ⅔ times the length thereof from the assembled condition.

In addition, the shape of the support section 53 is not limited, insofar as the shape thereof permits the support section 53 to support the cover body section 921. Preferably, however, the shape of an inner surface of the support section 53 corresponds to (is the same as) the shape of an outer surface (outer peripheral surface) of the cover body section 921. In the illustrated configuration, the outer surface of the cover body section 921 and the inner surface of the support section 53 each includes an arcuate portion.

This ensures that the cover body section 921 can be supported by the support section 53 more assuredly, and that the center axis $O_1$ of the outer needle 2 can be more securely prevented from becoming inclined when the outer needle 2 is moved in the distal direction relative to the inner needle 4.

Further, the first wall portion 531 is formed with a cutout 515 in a distal portion thereof, whereas the aforementioned finger hold 6 is disposed at the cutout 515.

Next, an example of a method for using the indwelling needle assembly 1 (in the case of puncturing a blood vessel) (operation of the assembly) will be described in detail below.

[1] The indwelling needle assembly 1 is placed in the assembled condition (see FIGS. 14, 16 and 22), and the connector 72 is preliminarily connected with a connector mounted to an end portion of an infusion line, thereby enabling an infusion to be supplied from the infusion line.

In this instance, incidentally, a predetermined portion of the tube 7 or the infusion line is pinched, for example, by a clamp (an example of a channel-opening/closing means) in order to close the inner cavity.

[2] Next, closure of the tube 7 or the infusion line by the clamp is released, whereby the infusion from the infusion line is introduced through the tube 7 into the outer-needle hub 3.

The infusion, which is introduced into the outer-needle hub 3, fills the channel 32, the channel 82, and a space on the distal side relative to the seal member 8, on the inside 31 of the outer-needle hub 3, and the infusion is introduced into the inner cavity 21 of the outer needle 2, thereby priming the inner cavity 21 of the outer needle 2 with the infusion. In this instance, a portion of the infusion flows out via the distal opening 22 of the outer needle 2.

[3] After priming is completed, the tube 7 or the infusion line once again is preliminarily closed by a clamp or the like, and the wings 12*a* and 12*b* are closed by pinching them with the fingers. Using the wings 12*a* and 12*b* as a grip portion (operating portion), a blood vessel (a vein or an artery) of the patient is punctured with the outer needle 2 and the inner needle 4 in a united fashion.

When a puncturing operation on the blood vessel is conducted by gripping the wings 12*a* and 12*b* in this manner, the puncturing angle is reduced. More specifically, the outer needle 2 and the inner needle 4 are set more closely in parallel in relation to the blood vessel, as compared to a case of conducting a puncturing operation by directly gripping the outer-needle hub 3. Consequently, the puncturing operation is facilitated, and the burden on the patient's blood vessel is lessened.

When the blood vessel is securely punctured with the outer needle 2, an internal pressure in the blood vessel (blood pressure) causes blood to flow back in the proximal direction through the groove 44 in the inner needle 4, and through the inner cavity 21 of the outer needle 2. Therefore, backflow of the blood can be confirmed at least at one of the outer needle 2, the outer-needle hub 3, the inner-needle hub 5, and the tube 7, the inside of which is visible.

After confirmation of backflow of the blood, the outer needle 2 is advanced a tiny distance in the distal direction along the inner needle 4, using the inner needle 4 as a guide.

When the finger hold 6 is pressed by an index finger in the distal direction (pressing operation), the outer needle 2, the outer-needle hub 3, and the protector 9 are moved as one body in the distal direction relative to the inner needle 4 and the inner-needle hub 5, as shown in FIG. 23.

In this case, the cover body section 921 of the protector 9 is supported by the first wall portion 531 and the second wall portion 532 (the support section 53), whereby the center axis $O_1$ of the outer needle 2 is inhibited from becoming inclined relative to the center axis $O_1$ of the outer needle 2, in the condition prior to the finger hold 6 being pressed. In particular, the distal side of the center axis $O_1$ of the outer needle 2 is inhibited from becoming inclined toward the opposite side from the finger hold 6 relative to the center axis $O_1$ of the outer needle 2, in the condition prior to the finger hold 6 being pressed.

Further, even if the outer needle 2 is moved by a greater distance, as shown in FIG. 24, the cover body section 921 remains supported by the first wall portion 531 and the second wall portion 532, without becoming disengaged from the protector accommodating section 51 of the inner-needle hub 5.

In this manner, the cover body section 921 remains supported by the first wall portion 531 and the second wall portion 532 until the outer needle 2 is moved a predetermined distance from the assembled condition. As a result, the center axis $O_1$ of the outer needle 2 is inhibited from becoming inclined. This enables the outer needle 2 to be moved straightly along its center axis $O_1$, or to be moved along the direction of the center axis $O_1$, without becoming bent. Consequently, the outer needle 2 can be advanced smoothly.

In addition, when the outer needle 2 is advanced in the distal direction, it is preferable to press the finger hold 6 in the distal direction with an index finger, while lifting up (in the manner of lifting up) the finger hold 6 in the projecting direction thereof (in an upward direction as shown in FIG. 16), thereby to move the outer needle 2 in the distal direction. This makes it possible to more securely prevent the center axis $O_1$ of the outer needle 2 from becoming inclined.

Further, when the blood vessel is punctured, erroneous penetration of bubbles into the blood vessel can be securely prevented, since the inner cavity 21 of the outer needle 2 has been primed with the infusion. Thus, extremely high safety is ensured.

In addition, in the assembled condition where the tube 7 is connected to a proximal portion of the outer-needle hub 3, the center axis $O_1$ of the outer needle 2 and the center axis $O_2$ at the distal portion of the tube 7 are substantially parallel to each other. Therefore, when puncturing the blood vessel with the outer needle 2 and the inner needle 4, the tube 7 will not obstruct the operation, and excellent operability can be ensured.

[4] After the blood vessel has been securely punctured with the outer needle 2 (after the outer needle 2 is moved to a desired position), the outer needle 2 or the outer-needle hub 3 is fixed with one hand, while the inner-needle hub 5 is gripped by the other hand and pulled in the proximal direction. This ensures that all the operations, ranging from the operation of pulling the inner needle 4 out of the outer needle 2 to disengagement of the protector 9 from the outer-needle hub 3, are sequentially carried out in a continuous manner. More specifically, the inner needle 4 initially is moved in the proximal direction, and then is pulled out from the outer needle 2.

[5] After the inner needle 4 has been moved further in the proximal direction and the point 41 passes through the slit 81, the seal member 8, which exhibits a self-closing property, closes the slit 81 under its own elastic force. As a result, leakage of liquid through the slit 81 is prevented, and sterility in the outer-needle hub 3 and the infusion line is secured.

[6] After the inner needle 4 has been moved further in the proximal direction and the point 41 reaches the proximal side of the shutter member 94, as shown in FIG. 25, the shutter member 94 opens under its own elastic force, so as to attain the second posture, which cuts off the inner-needle passage 931. When the shutter member 94 has come into the second posture, any attempt to move the point 41 of the inner needle 4 back in the distal direction simply results in the point 41 coming into abutment on the shutter member 94, and hence the inner needle 4 cannot return in the distal direction.

[7] After the inner needle 4 has been moved further in the proximal direction and the inner needle 4 reaches the proximal side of the lock member 933, as shown in FIG. 26, rotation of the lock member 933 is allowed, and the internal member 93 of the protector 9 can be moved in the proximal direction relative to the protector cover 92.

On the other hand, when the inner-needle hub 5 is pulled in the proximal direction, the internal member 93 is pulled and moved in the proximal direction through the link member 20. After the distal portion of the internal member 93 reaches the proximal side of the projections 923 of the protector cover 92, as shown in FIG. 27, the projections 923 are made capable of moving toward the center axis of the inner needle 4. Consequently, it becomes possible for the protector 9 to be moved in the proximal direction relative to the outer-needle hub 3.

[8] After the internal member 93 has been moved further in the proximal direction, and the projected portions 932 of the internal member 93 abut on the proximal-side edge portions 926 of the slots 925 in the protector cover 92, as shown in FIG. 27, the internal member 93 and the protector cover 92 are moved as a unitary body in the proximal direction, whereupon the protector 9 becomes separated (disengaged) from the outer-needle hub 3.

Figure 28:
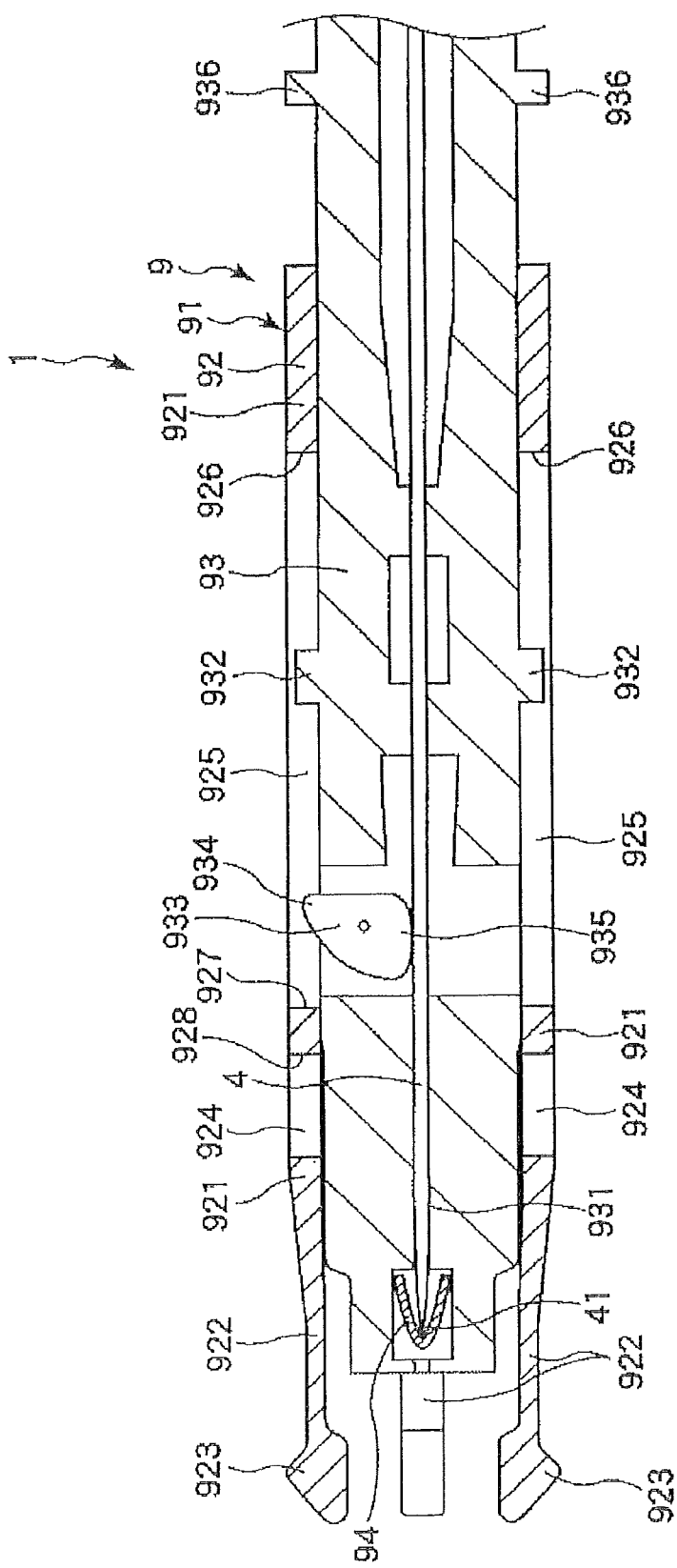
FIG. 28 is a sectional view taken along line B-B of FIG. 16.

[9] In addition, due to the restoring force of the link member 20, the internal member 93 is pulled and moved in the proximal direction relative to the inner needle 4, and the point 41 presses the bottom portion 935 of the lock member 933, as shown in FIG. 28, whereby the lock member 933 is placed in a posture in which the tip portion 934 thereof is directed away from the inner needle 4 (directed toward the upper side in FIG. 28). In addition, the inner needle 4 makes contact with the bottom portion 935 of the lock member 933, thereby maintaining this posture.

[10] By the restoring force of the link member 20, the internal member 93 is further moved in the proximal direction relative to the inner needle 4, resulting in the point 41 of the inner needle 4 coming into contact with the shutter member 94, as shown in FIG. 28.

Further, in the condition where the point 41 is in contact with the shutter member 94, the internal member 93 is biased in the proximal direction by the restoring force of the link member 20, whereby this condition can be maintained.

In addition, the link member 20 has a given length so that the point 41 is accommodated in the internal member 93, in the condition where the link member 20 is maximally extended. Therefore, the protector 9 can securely be prevented from slipping off the point 41. Accordingly, the condition in which the point 41 is covered by the protector 9 can be maintained assuredly.

[11] Next, the tube 7, which is inserted in the tube accommodating section 52 of the inner-needle hub 5, is removed through the groove 521.

After the inner needle 4 has been pulled out from the outer needle 2 in this manner, the inner needle 4 and the inner-needle hub 5 are rendered useless, and therefore are discarded.

The point 41 of the inner needle 4 is covered with the protector 9. In particular, the point 41 is prevented from moving toward the distal side beyond the shutter member 94 and to protrude from the distal end of the protector 9.

Accordingly, an accident, in which the person in charge of disposing of the inner needle 4 mistakenly punctures his or her hand or finger with the point 41, can be prevented from occurring.

[12] Subsequently, the wings 12a and 12b are opened and are fixed to a skin by a pressure sensitive adhesive tape or the like. In addition, closure of the tube 7 or the infusion line by the clamp is released, whereby supply of the infusion is started.

The infusion supplied from the infusion line is injected into the patient's blood vessel through the inner cavities of the connector 72, the tube 7, the outer-needle hub 3, and the outer needle 2.

As has been described above, according to the present indwelling needle assembly 1, when the outer needle 2 is moved in the distal direction relative to the inner needle 4 during a puncturing operation, the cover body section (the supported section) 921 is supported by the support section 53, while the center axis $O_1$ of the outer needle 2 is inhibited from becoming inclined (being deviated).

Specifically, the distal side of the center axis $O_1$ of the outer needle 2 is inhibited from becoming inclined toward the opposite side from the finger hold 6 relative to the center axis $O_1$ of the outer needle 2, in a condition before the finger hold 6 actually is pressed. This enables the outer needle 2 to be moved straightly along the center axis $O_1$, or to be moved along the direction of the center axis $O_1$, without becoming bent. This, in turn, enables the outer needle 2 to be moved (advanced) smoothly. Consequently, excellent operability is ensured, whereby an infusion line or the like can be secured easily and reliably.

Incidentally, although the supported section is formed in the protector 9 in the present embodiment, the present invention is not limited to this configuration. Alternatively, the supported section may be formed in the outer-needle hub 3, for example, or may be formed in both the protector 9 and the outer-needle hub 3. In other words, the support section may be configured so as to support the outer-needle hub 3, or may be configured to support both the protector 9 and the outer-needle hub 3.

In the case that the supported section is formed in both the protector 9 and the outer-needle hub 3, examples of the possible configurations include the following configurations (1) to (4), among which configuration (2) is particularly preferred.

(Configuration 1)

A configuration that can assume a condition in which the support section supports only the outer-needle hub 3, and a condition where the support section supports only the protector 9.

(Configuration 2)

A configuration that can assume a condition in which the support section supports the outer-needle hub 3 and the protector 9, and a condition where the support section supports only the protector 9.

(Configuration 3)

A configuration that can assume a condition in which the support section supports the outer-needle hub 3 and the protector 9, and a condition where the support section supports only the outer-needle hub 3.

(Configuration 4)

A configuration that can assume a condition in which the support section supports the outer-needle hub 3 and the protector 9, a condition in which the support section supports only the protector 9, and a condition in which the support section supports only the outer-needle hub 3.

In addition, although the finger hold is provided on the protector 9 in the present embodiment, the present invention is not limited to this configuration. The finger hold may be formed (provided) to project on another part (member), for example, the outer-needle hub 3, as shown in FIG. 31.

Further, in the present invention, the finger hold may have a shape such that, when the outer needle 2 is moved in the distal direction relative to the inner needle 4, a force in a direction of projection of the finger hold 6 (projecting direction) relative to the center axis $O_1$ of the outer needle 2 cannot act on the finger hold 6. For instance, the angle between the finger hold surface 64 and the center axis $O_1$ of the outer needle 2 (i.e., the angle θ shown in FIG. 17) may be 90°, or may be greater than 90°.

In addition, in the present invention, the finger hold need not necessarily be a projecting finger hold. In other words, the finger hold may be constituted by various shapes. For instance, the finger hold may be configured such that an outer surface of the protector 9, or an outer surface of the outer-needle hub 3, constitutes the finger hold surface of the finger hold.

While the indwelling needle assembly according to the present invention has been described above referring to the embodiments shown in the drawings, the invention is not limited to these embodiments. Components of the indwelling needle assembly may be replaced by any configurations that can exhibit functions equivalent to those mentioned above. In addition, other structures may be added to the above-described indwelling needle assembly.

In addition, the present invention may comprise a combination of any two or more configurations (features) chosen from among the aforementioned embodiments.

Further, the indwelling needle assembly according to the present invention is not limited to being used in a state of insertion in a blood vessel. For instance, the indwelling needle assembly of the invention also is applicable to indwelling needle assemblies, which are used in a state of being inserted in an abdominal cavity, thoracic cavity, lymph vessel, vertebral canal, or the like.

Further, in the present invention, the shape of the slit in the seal member is not limited to the shape of a straight line. For example, the shape may be a cross shape, Y-shape, T-shape, H-shape, or the like.

In addition, in the present invention, a cap may be provided, which is mounted on a proximal portion of the outer-needle hub after the inner needle has been pulled out of the outer needle. This enables more secure prevention of leakage of liquid from the proximal end of the outer-needle hub. The cap may be formed as a single body with the outer-needle hub, or may be a separate body from the outer-needle hub. Further, any of various methods for fixing the cap to the outer-needle hub may be used. For example, a method by means of friction, hooking or the like may be adopted.

Further, in the present invention, the protector is not limited to being configured as shown in the drawings, insofar as the protector is detachably connected to the outer-needle hub. Especially, use can be made of protectors of various configurations, which are designed to cover at least the point of the inner needle, upon the inner needle being pulled out from the outer needle.

In addition, in the present invention, the connector provided at the end portion of the tube is not particularly limited. Examples of connectors usable herein include the needleless connector described in Japanese Patent Laid-Open Patent Publication No. 2005-261931, a three-way cock, etc.

Further, in the present invention, the component to be provided at the end portion of the tube is not limited to the aforementioned connector, but may be a cap, an air filter or the like, for example.

Further, in the indwelling needle assembly according to the present invention, the aforementioned connector, cap and air filter may be exchangeably attached to the end portion of the tube, as required.

INDUSTRIAL APPLICABILITY

According to the present invention, the finger hold has a shape such that, when the outer needle is moved in the distal direction relative to the inner needle, a force in an upward direction (vertically upward direction), or a force in the direction of projection of the finger hold (projecting direction) relative to the axis of the outer needle can act on the finger hold. Therefore, when the outer needle is moved in the distal direction relative to the inner needle during a puncturing operation, the finger hold can be pressed by the finger while lifting up (in the manner of lifting up) the finger hold in the projecting direction thereof. This enables the outer needle to be moved straightly along its axis, or moved along the direction of its own axis, without becoming bent. This, in turn, enables the outer needle to be moved (advanced) smoothly. Consequently, excellent operability is ensured, and an infusion line or the like can be secured easily and reliably.

In addition, according to the present invention, when the outer needle is moved in the distal direction relative to the inner needle, the supported section is supported by the support section, so that the axis of the outer needle is inhibited from being inclined (becoming deviated). This ensures that the outer needle can be moved straight along its axis, or moved along the direction of its own axis, without becoming bent. This, in turn, enables the outer needle to be moved (advanced) smoothly. Consequently, excellent operability is ensured, and an infusion line or the like can be secured easily and assuredly.

Accordingly, the present invention has industrial applicability.

The invention claimed is:

1. An indwelling needle assembly, comprising;
an inner needle having a sharp point at a distal end;
an inner-needle hub fixed to a proximal portion of the inner needle;
a hollow outer needle in which the inner needle is inserted;
an outer-needle hub fixed to a proximal portion of the outer needle, the outer-needle hub possessing an axis;

a protector detachably connected to the outer-needle hub a finger hold connected to the outer-needle hub or the protector at a base end of the finger hold and terminating at a free end remote from the base end, the finger hold being pressable by a finger to move the outer needle in the distal direction relative to the inner needle;

wherein the finger hold projects in an upward direction, the finger hold comprising an inclined plate which is inclined toward a proximal side, the inclined plate possessing: (i) a finger hold surface on which to place a finger, the finger hold surface being on the proximal side of the inclined plate, the finger hold surface possessing a first end adjoining the base end of the finger hold and a second end adjoining the free end of the finger hold; and (ii) a distal surface positioned on an opposite side of the inclined plate than the finger hold surface, the distal surface possessing a first end adjoining the base end of the finger hold and a second end adjoining the free end of the finger hold;

the second end of the finger hold surface being proximal to the first end of the finger hold surface, and the second end of the distal surface being proximal to the first end of the distal surface;

the first end of the finger hold surface being angled at 45° to 75° with respect to the axis of the outer needle;

wherein the free end of the finger hold is positioned proximally of the first end of the finger hold surface; and wherein when the outer needle is moved in the distal direction relative to the inner needle, a force in an upward direction relative to the axis of the outer needle can act on the finger hold.

2. The indwelling needle assembly according to claim 1, wherein upon pulling of the inner needle out of the outer needle, the protector covers at least the point of the inner needle.

3. The indwelling needle assembly according to claim 1, wherein the finger hold surface is provided with an anti-slipping means for the finger.

4. The indwelling needle assembly according to claim 1, wherein the finger hold is inclined at an angle of 45° to 75° with respect to the axis of the outer needle.

5. The indwelling needle assembly according to claim 1, wherein the axis of the outer needle extends straight from its distal portion to its proximal portion thereof.

6. The indwelling needle assembly according to claim 1, wherein the first end of the finger hold surface is a planar surface.

7. The indwelling needle assembly according to claim 1, wherein the base end of the finger hold is connected to the outer-needle hub or the protector by way of a cantilevered connecting portion.

8. The indwelling needle assembly according to claim 1, wherein the outer-needle hub includes a recess, and the protector includes an axially extending projected section from which projects a projection positioned in the recess of the outer-needle hub to prevent relative axial movement of the protector and the outer-needle hub, the projection being disengageable from the recess to permit relative axial movement of the protector and the outer-needle hub.

9. The indwelling needle assembly according to claim 8, wherein the projected section and the finger hold axially overlap one another.

10. The indwelling needle assembly according to claim 1, wherein the outer needle hub includes a plurality of through holes, and the protector includes a plurality of circumferentially spaced apart projected sections, with a projection projecting from an end portion of each projected section, each projection being positioned in a respective one of the through holes in the outer needle hub to prevent relative axial movement of the protector and the outer hub, the projections being disengageable from the respective recesses to permit relative axial movement of the protector and the outer hub.

11. An indwelling needle assembly, comprising:

an inner needle having a sharp point at a distal end;

an inner-needle hub fixed to a proximal portion of the inner needle;

a hollow outer needle in which the inner needle is inserted;

an outer-needle hub fixed to a proximal portion of the outer needle, the outer-needle hub possessing an axis;

a protector detachably connected to the outer-needle hub;

a finger hold connected to the outer-needle hub or the protector at a base end of the finger hold and projecting away from the base end to terminate in a free end at a tip-most end of the finger hold, the finger hold being pressable by a finger to move the outer needle in the distal direction relative to the inner needle;

the finger hold comprising an inclined plate which is inclined toward a proximal side, the inclined plate possessing: (i) a proximally facing planar finger hold surface on which to place a finger, the proximally facing planar finger hold surface possessing a first end adjoining the base end of the finger hold and a second end adjoining the free end of the finger hold; and (ii) a distally facing surface possessing a first end adjoining the base end of the finger hold and a second end adjoining the free end of the finger hold;

the second end of the proximally facing planar finger hold surface being proximal to the first end of the proximally facing planar finger hold surface, and the second end of the distally facing surface being proximal to the first end of the distally facing surface;

the proximally facing planar finger hold surface portion being angled at 45° to 75° with respect to the axis of the outer needle; and when the outer needle is moved in the distal direction relative to the inner needle, a force directed away from the axis of the outer needle acts on the finger hold.

* * * * *